United States Patent
Agbandje-McKenna et al.

(10) Patent No.: US 10,426,844 B2
(45) Date of Patent: Oct. 1, 2019

(54) CAPSID-MUTATED RAAV VECTORS AND METHODS OF USE

(71) Applicant: University of Florida Research Foundation, Inc., Gainesville, FL (US)

(72) Inventors: Mavis Agbandje-McKenna, Gainesville, FL (US); William W. Hauswirth, Gainesville, FL (US); Arun Srivastava, Gainesville, FL (US); Li Zhong, Boxborough, MA (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/246,385

(22) Filed: Aug. 24, 2016

(65) Prior Publication Data

US 2016/0361439 A1    Dec. 15, 2016

Related U.S. Application Data

(63) Continuation of application No. 14/298,553, filed on Jun. 6, 2014, now abandoned, which is a continuation-in-part of application No. 12/993,092, filed as application No. PCT/US2009/044753 on May 20, 2009, now abandoned.

(60) Provisional application No. 61/054,571, filed on May 20, 2008, provisional application No. 61/199,241, filed on Nov. 14, 2008, provisional application No. 61/200,430, filed on Nov. 26, 2008.

(51) Int. Cl.

| | |
|---|---|
| *C12N 15/86* | (2006.01) |
| *A61K 48/00* | (2006.01) |
| *C07K 14/705* | (2006.01) |
| *A61K 45/06* | (2006.01) |
| *C07K 14/72* | (2006.01) |

(52) U.S. Cl.
CPC .......... *A61K 48/0058* (2013.01); *A61K 45/06* (2013.01); *A61K 48/005* (2013.01); *C07K 14/70571* (2013.01); *C07K 14/723* (2013.01); *C12N 15/86* (2013.01); *C12N 2710/10043* (2013.01); *C12N 2799/025* (2013.01); *C12N 2830/008* (2013.01)

(58) Field of Classification Search
CPC .................................................. A61K 48/0058
See application file for complete search history.

(56) References Cited

U.S. PATENT DOCUMENTS

| | | | |
|---|---|---|---|
| 4,522,811 A | 6/1985 | Eppstein et al. | |
| 5,091,309 A | 2/1992 | Schlesinger et al. | |
| 5,217,879 A | 6/1993 | Huang et al. | |
| 5,872,005 A | 2/1999 | Wang et al. | |
| 5,912,122 A | 6/1999 | Daggett et al. | |
| 6,084,084 A | 7/2000 | Stormann et al. | |
| 6,156,303 A | 12/2000 | Russell et al. | |
| 6,204,251 B1 | 3/2001 | Cuthbertson | |
| 6,245,330 B1 | 6/2001 | Horellou et al. | |
| 6,362,316 B1 | 3/2002 | Daggett et al. | |
| 7,052,692 B1 | 5/2006 | Srivastava et al. | |
| 7,094,604 B2 | 8/2006 | Snyder et al. | |
| 7,144,733 B2 | 12/2006 | Miesenbock et al. | |
| 7,342,111 B2 | 3/2008 | Lewin et al. | |
| 7,824,869 B2 | 11/2010 | Hegemann et al. | |
| 8,445,267 B2 | 5/2013 | Zhong et al. | |
| 8,802,440 B2 | 8/2014 | Zhong et al. | |
| 9,157,098 B2 | 10/2015 | Zhong et al. | |
| 9,611,302 B2 | 4/2017 | Srivastava et al. | |
| 9,725,485 B2 | 8/2017 | Srivastava et al. | |
| 9,775,918 B2 | 10/2017 | Zhong et al. | |

(Continued)

FOREIGN PATENT DOCUMENTS

| | | |
|---|---|---|
| CA | 2826273 A1 | 8/2012 |
| CN | 102159713 A | 8/2011 |

(Continued)

OTHER PUBLICATIONS

Rakoczy et al, (Drug Development Research, 46: 277-285, 1999). (Year: 1999).*
U.S. Appl. No. 15/680,668, filed Aug. 18, 2017, Zhong et al.
U.S. Appl. No. 15/444,235, filed Feb. 27, 2017, Srivastava et al.
U.S. Appl. No. 15/672,265, filed Aug. 8, 2017, Zhong et al.
U.S. Appl. No. 13/899,481, filed May 21, 2013, Zhong et al.
U.S. Appl. No. 14/891,241, filed Nov. 13, 2015, Srivastava et al.
U.S. Appl. No. 14/214,011, filed Mar. 14, 2014, Srivastava et al.
U.S. Appl. No. 15/548,728, filed Aug. 3, 2017, Aslanidi et al.
EP 08733161.7, Jan. 27, 2011, EP Examination Report.
EP 08733161.7, Jul. 25, 2011, Response to EP Examination Report.
CA 2,720,097, Oct. 22, 2013, Examination Report.

(Continued)

*Primary Examiner* — Anoop K Singh
*Assistant Examiner* — Magdalene K Sgagias
(74) *Attorney, Agent, or Firm* — Wolf, Greenfield & Sacks, P.C.

(57) ABSTRACT

Disclosed are capsid-mutated rAAV vectors and methods for their use in gene therapy, and particularly for use in delivering therapeutic transgenes to treat a variety of mammalian diseases and disorders, including dysfunctions and abnormal conditions of the human eye. VP3 capsid proteins comprising a modification of one or more of the surface-exposed tyrosine residues are disclosed, and in particular, VP3 capsid protein comprising tyrosine-to-phenylalanine mutations at positions corresponding to Y444F, Y500F, and Y730F of the wild-type AAV2 sequence. Also provided are rAAV virions and viral particles that comprise such a mutated AAV capsid protein and a nucleic acid molecule that expresses one or more selected therapeutic or reporter transgenes in one or more mammalian cells of interest. Advantageously, the capsid-mutated rAAV vectors and virions disclosed herein afford improved transduction efficiency in a variety of cells, tissues and organs of interest, when compared to their unmodified (i.e., wild-type) rAAV vector counterparts.

10 Claims, 13 Drawing Sheets

Specification includes a Sequence Listing.

(56) References Cited

U.S. PATENT DOCUMENTS

| | | |
|---|---|---|
| 9,920,097 B2 | 3/2018 | Zhong et al. |
| 2002/0064870 A1 | 5/2002 | Briand et al. |
| 2003/0138772 A1 | 7/2003 | Gao et al. |
| 2003/0219733 A1 | 11/2003 | Clark et al. |
| 2005/0202398 A1 | 9/2005 | Hegemann et al. |
| 2005/0208022 A1 | 9/2005 | Masland |
| 2006/0292117 A1 | 12/2006 | Loiler et al. |
| 2007/0053996 A1 | 3/2007 | Boyden et al. |
| 2007/0054319 A1 | 3/2007 | Boyden et al. |
| 2007/0259420 A1 | 11/2007 | Greenbaum et al. |
| 2007/0261127 A1 | 11/2007 | Boyden et al. |
| 2007/0276024 A1 | 11/2007 | Bond |
| 2008/0085265 A1 | 4/2008 | Schneider et al. |
| 2008/0125832 A1 | 5/2008 | Horsager et al. |
| 2009/0074723 A1 | 3/2009 | Acland et al. |
| 2009/0088399 A1 | 4/2009 | Balya et al. |
| 2009/0088680 A1 | 4/2009 | Aravanis et al. |
| 2009/0099038 A1 | 4/2009 | Deisseroth et al. |
| 2009/0281163 A1 | 11/2009 | Cepko et al. |
| 2009/0312818 A1 | 12/2009 | Horsager et al. |
| 2010/0006049 A1 | 1/2010 | Jung et al. |
| 2010/0015095 A1 | 1/2010 | Pan et al. |
| 2010/0016783 A1 | 1/2010 | Bomke et al. |
| 2010/0104561 A1 | 4/2010 | Zhong et al. |
| 2010/0190229 A1 | 7/2010 | Zhang et al. |
| 2010/0234273 A1 | 9/2010 | Boyden et al. |
| 2011/0021970 A1 | 1/2011 | Vo-Dinh et al. |
| 2011/0086421 A1 | 4/2011 | Hegemann et al. |
| 2013/0225664 A1 | 5/2013 | Horsager et al. |
| 2013/0203841 A1 | 8/2013 | Zhong et al. |
| 2013/0216501 A1 | 8/2013 | Zhong et al. |
| 2013/0224836 A1 | 8/2013 | Muramatsu |
| 2013/0310443 A1 | 11/2013 | Srivastava et al. |
| 2014/0022766 A1 | 1/2014 | Wright |
| 2014/0050701 A1 | 2/2014 | Zhong et al. |
| 2014/0099284 A1 | 4/2014 | Horsager et al. |
| 2014/0341852 A1 | 11/2014 | Srivastava et al. |
| 2015/0133530 A1 | 5/2015 | Srivastava et al. |
| 2016/0106865 A1 | 4/2016 | Zhong et al. |
| 2016/0333372 A1 | 11/2016 | Srivastava et al. |
| 2017/0275337 A1 | 9/2017 | Srivastava et al. |
| 2018/0030096 A1 | 2/2018 | Aslanidi et al. |
| 2018/0036428 A1 | 2/2018 | Zhong et al. |
| 2018/0105559 A1 | 4/2018 | Zhong et al. |

FOREIGN PATENT DOCUMENTS

| | | |
|---|---|---|
| CN | 102994549 A | 3/2013 |
| CN | 103060331 A | 4/2013 |
| CN | 104470945 A | 3/2015 |
| EP | 1310571 A2 | 5/2003 |
| EP | 1 486 567 A1 | 12/2004 |
| EP | 1891976 A1 | 2/2008 |
| EP | 1492881 B1 | 10/2008 |
| EP | 2 660 325 A2 | 11/2013 |
| WO | WO 1990/011092 | 10/1990 |
| WO | WO 1992/008796 A1 | 5/1992 |
| WO | WO 1994/028143 A1 | 12/1994 |
| WO | WO 1995/007994 | 3/1995 |
| WO | WO 1995/012387 | 5/1995 |
| WO | WO 1995/024929 | 9/1995 |
| WO | WO 1996/029404 A1 | 9/1996 |
| WO | WO 1998/048027 A2 | 10/1998 |
| WO | WO 2000/054813 | 9/2000 |
| WO | WO 2001/083692 | 11/2001 |
| WO | WO 03/006616 A2 | 1/2003 |
| WO | WO 03/052052 A2 | 6/2003 |
| WO | WO 2003/047525 A2 | 6/2003 |
| WO | WO 2004/009022 A2 | 1/2004 |
| WO | WO 2004/027019 A2 | 4/2004 |
| WO | WO 2004/084951 A2 | 10/2004 |
| WO | WO 2004/111248 A2 | 12/2004 |
| WO | WO 2005/080573 A1 | 9/2005 |
| WO | WO 2006/079217 A1 | 8/2006 |
| WO | WO 2006/110689 A2 | 10/2006 |
| WO | WO 2006/119150 A2 | 11/2006 |
| WO | WO 2007/131180 A2 | 11/2007 |
| WO | WO 2008/022772 A1 | 2/2008 |
| WO | WO 2008/086470 A1 | 7/2008 |
| WO | WO 2008/089003 A2 | 7/2008 |
| WO | WO 2008/124724 A1 | 10/2008 |
| WO | WO 2008/145400 A2 | 12/2008 |
| WO | WO 2009/124189 A1 | 10/2009 |
| WO | WO 2009/127705 A1 | 10/2009 |
| WO | WO 2010/006049 A1 | 1/2010 |
| WO | WO 2010/009141 A1 | 1/2010 |
| WO | WO 2010/011404 A2 | 1/2010 |
| WO | WO 2010/123993 A1 | 10/2010 |
| WO | WO 2012/057363 A2 | 5/2012 |

OTHER PUBLICATIONS

PCT/US2008/059647, Sep. 10, 2008, International Search Report and Written Opinion.

PCT/US2008/059647, Oct. 13, 2009, International Preliminary Report on Patentability.

PCT/US2013/041234, Feb. 13, 2014, International Search Report and Written Opinion.

PCT/US2013/041234, Nov. 27, 2014, International Preliminary Report on Patentability.

PCT/US2014/039015, Nov. 24, 2014, International Search Report and Written Opinion.

PCT/US2014/039015, Dec. 3, 2015, International Preliminary Report on Patentability.

PCT/US2016/016422, May 5, 2016, International Search Report and Written Opinion.

PCT/US2016/016422, Aug. 17, 2017, International Preliminary Report on Patentability.

EP Examination Report dated Jan. 27, 2011, issued in EP 08733161.7-2405 (3 pages).

Response to EP Examination Report dated Jul. 25, 2011, issued in EP 08733161.7-2405 (8 pages).

Examination Report dated Oct. 22, 2013, issued in CIPO 2,720,097 (2 pages).

International Preliminary Report on Patentability for Application No. PCT/US2008/059647 dated Oct. 13, 2009.

International Search Report and Written Opinion for Application No. PCT/US2008/059647 dated Sep. 10, 2008.

International Search Report and Written Opinion for Application No. PCT/US2013/041234 dated Feb. 13, 2014.

International Preliminary Report on Patentability for Application No. PCT/US2013/041234 dated Nov. 27, 2014.

International Search Report and Written Opinion for Application No. PCT/US2014/039015 dated Nov. 24, 2014.

International Preliminary Report on Patentability for Application No. PCT/US2014/039015 dated Dec. 3, 2015.

International Search Report and Written Opinion for Application No. PCT/US2016/016422 dated May 5, 2016.

International Preliminary Report on Patentability for Application No. PCT/US2016/016422 dated Aug. 17, 2017.

Aslanidi, George V. et al, High-Efficiency Transduction of Human Monocyte-Derived Dendritic Cells by Capsid-Modified Recombinant AAV2 Vectors, Vaccine 30:3908-3917 (2012), .Copyrgt. 2012 Elsevier Ltd., pp. 3908-3917.

Aslanidi, George V. et al, Optimization of the Capsid of Recombinant Adeno-Associated Virus 2 (AAV2) Vectors: The Final Threshold?, PLoS One 8(3): e59142 (Mar. 2013), 12 pages.

Aslanidi et al., Abstract C240: Modification on the capsid of recombinant adeno-associated virus vectors (rAAV) leads to high-efficiency transduction of human monocyte-derived dendritic cells (moDCs). Mol Cancer Ther. Nov. 10, 2011(11): Abstract C240. 3 Pages.

Bantel-Schaal et al., Human adeno-associated virus type 5 is only distantly related to other known primate helper-dependent parvoviruses. J Virol. Feb. 1999;73(2):939-47.

Cheng, Binbin et al, Development of Optimized AAV3 Serotype Vectors: Mechanism of High-Efficiency Transduction of Human Liver Cancer Cells,Gene Ther. Apr. 2011; 19(4): 375-384, 24 pages.

(56) References Cited

OTHER PUBLICATIONS

Chiorini et al., Capsid Protein [Adeno-associated virus-5] GENBANK Accession No. YP-068409 Dec. 8, 2008.
Dalkara, D., et al., Enhanced Gene Delivery to the Neonatal Retina Through Systemic Administration of Tyrosine-Mutated AAV9,. Copyrgt. 2012 Macmillan Publishers Limited (0969-7128/12), www.nature.com/gt, Gene Therapy (2012) 19, pp. 176-181.
Gabriel et al., Targeted Mutagenesis of Ubiquitin-Binding Lysine Residues on the Adeno-Associated Virus (AAV)2 Capsid Improves Its Transduction Efficiency. Mol Ther. 2012;20(Supp 1):S146.
Horowitz, Eric D., et al., Tyrosine Cross-Linking Reveals Interfacial Dynamics in Adeno-Associated Viral Capsids During Infection, ACS Chemical Biology, pubs.acs.org/acschemicalbiology, ACS Publications, .Copyrgt. American Chemical Society,dx.doi.org/10.1021/cb3000265, Mar. 29, 2012, pp. A-H.
Jayandharan, Giridhara R. et al., Activation of the NF-kB Pathway by Adeno-Associated Virus (AAV) Vectors and its Implications in Immune Response and Gene Therapy, PNAS, Mar. 1, 2011, vol. 108, No. 9, pp. 3743-3748.
Kauss, M. Ariel, et al., Enhanced Long-Term Transduction and Multilineage Engraftment of Human Hematopoietic Stem Cells Transduced With Tyrosine-Modified Recombinant Adeno-Associated Virus Serotype 2, Human Gene Therapy 21:1129-1136 (Sep. 2010),.Copyrgt. Mary Ann Liebert, Inc., doi: 10.1089/hum.2010.016, pp. 1129-1136.
Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.
Kern et al., Identification of a heparin-binding motif on adeno-associated virus type 2 capsids. J Virol. Oct. 2003;77(20):11072-81.
Ku, Cristy A., et al., Gene Therapy Using Self-Complementary T733F Capsid Mutant AAV2/8 Restores Vision in a Model of Early Onset Leber Congenital Amaurosis, .Copyrgt. The Author 2011, Published by Oxford University Press, Human MolecularGenetics, 2011, doi: 10.1093/hmg/ddr391, pp. 1-13.
Le Meur, G. et al., Restoration of vision in RPE65-deficient Briard dogs using an AAV serotype 4 vector that specifically targets the retinal pigmented epithelium, Gene Therapy 14(4):292-303 (Feb. 2007), 12 pages.
Li et al., Site-Directed Mutagenesis of Surface-Exposed Lysine Residues Leads to Improved Transduction by Recombinant Aav2 and Aav8 Vectors in Murine Hepatocytes in Vivo. Mol Ther. 2013;21(Supp 1):S208-9.
Ling et al, Selective in vivo targeting of human liver tumors by optimized AAV3 vectors in a murine xenograft model. Hum Gene Ther. Dec. 2014;25(12):1023-34. doi: 10.1089/hum.2014.099.
Lochrie, Michael A. et al., Mutations on the External Surfaces of Adeno-Associated Virus Type 2 Capsids That Affect Transduction and Neutralization,Journal of Virology 80(2):821-834 (Jan. 2006), 14 pages.
Locke, Michelle, et al., Transduction of Human Adipose-Derived Mesenchymal Stem Cells by Recombinant Adeno-Associated Virus Vectors, Copyrgt. Mary Ann Liebert, Inc., DOI: 10.1089/ten.tec.2011.0153, Tissue Engineering: Part C; vol. 17, No. 9,2011, pp. 949-959.
Markusic, David M. et al., High-Efficiency Transduction and Correction of Murine Hemophelia B Using AAV2 Vectors Devoid of Multiple Surface-Exposed Tyrosines, Molecular Therapy (Dec. 2010), vol. 18, No. 12, pp. 2048-2056.
Opie et al., Identification of amino acid residues in the capsid proteins of adeno-associated virus type 2 that contribute to heparan sulfate proteoglycan binding. J Virol. Jun. 2003;77(12):6995-7006.
Pandya et al., Rationally designed capsid and transgene cassette of AAV6 vectors for dendritic cell-based cancer immunotherapy. Immunol Cell Biol. Feb. 2014;92(2):116-23. doi: 10.1038/icb.2013.74. Epub Nov. 12, 2013.
Pang, Ji-Jing, et al., Long-Term Retinal Function and Structure Rescue Using Capsid Mutant AAV8 Vector in the rd10 Mouse, a Model or Recessive Retinitis Pigmentosa,.Copyrgt. The American Society of Gene & Cell Therapy, Molecular Therapy, pp. 1-9,2010.
Petrs-Silva, Hilda, et al., High-Efficiency Transduction of the Mouse Retina by Tyrosine-Mutant AAV Serotype Vectors .Copyrgt. The American Society of Gene & Cell Therapy, www.moleculartherapy.org, Molecular Therapy, vol. 17, No. 3, pp. 463-471,Mar. 2009.
Petrs-Silva, Hilda, et al., Novel Properties of Tyrosine-Mutant AAV2 Vectors in the Mouse Retina, .Copyrgt. The American Society of Gene & Cell Therapy, Molecular Therapy, www.moleculartherapy.org, pp. 1-9, 2010.
Qi, YanFei, et al., Comparison of Transduction Efficiency of Tyrosine-Mutant AAV Serotype Vectors in Kidney, .Copyrgt. 2012 The Authors Clinical and Experimental Pharmacology and Physiology, .Copyrgt. 2012 Wiley Publishing Asia Pty Ltd., doi:10.1111/1440-1681.12037, 8 pages.
Qiao, Chunping, et al., Adeno-Associated Virus Serotype 6 Capsid Tyrosine-to-Phenylalanine Mutations Improve Gene Transfer to Skeletal Muscle, Human Gene Therapy 21:1343-1348 (Oct. 2010), .Copyrgt. Mary Ann Liebert, Inc., doi:10.1089/hum.2010.003, pp. 1343-1348.
Qiao, Chunping, et al., Single Tyrosine Mutation in AAV8 and AAV9 Capsids Is Insufficient to Enhance Gene Delivery to Skeletal Muscle and Heart, Human Gene Therapy Methods: Part B 23:29-37 (Feb. 2012), .Copyrgt. Mary Ann Liebert, Inc., doi:10.1089/hgtb.2011.229, pp. 29-37.
Ruan, Qing, et al., Development of an Anti-Angiogenic Therapeutic Model Combining scAAV2-delivered siRNAs and Noninvasive Photoacoustic Imaging of Tumor Vasculature Development, Cancer Lett. (2012), http://dx.doi.org/10.1016/j.canlet.2012.11.016,Dec. 4, 2012, 10 pages.
Ryals, Renee C., et al., Quantifying Transduction Efficiencies of Unmodified and Tyrosine Capsid Mutant AAV Vectors in Vitro Using Two Ocular Cell Lines, Molecular Vision 2011; 17:1090-1102 (http://www.molvis.org/molvis/v17/a124), Apr. 29, 2011,pp. 1090-1102.
Schaffer et al., GenBank Submission: ADW24587. Apr. 7, 2005.
Shin, Jin-Hong, et al., A Simplified Immune Suppression Scheme Leads to Persistent Micro-Dystrophin Expression in Duchenne Muscular Dystrophy Dogs, Human Gene Therapy 23:202-209 (Feb. 2012), .Copyrgt. Mary Ann Libert, Inc., doi:10.1089/hum.2011,147, pp. 202-209.
Song et al., High-efficiency transduction of primary human hematopoietic stem cells and erythroid lineage-restricted expression by optimized AAV6 serotype vectors in vitro and in a murine xenograft model in vivo. PLoS One. 2013;8(3):e58757. doi: 10.1371/journal.pone.0058757. Epub Mar. 14, 2013.
Ussher, James E., et al., Optimized Transduction of Human Monocyte-Derived Dendritic Cells by Recombinant Adeno-Associated Virus Serotype 6, Human Gene Therapy 21:1675-1686 (Dec. 2010), .Copyrgt. Mary Ann Liebert, Inc., doi: 10.1089/hum.2010.078,pp. 1675-1686.
Vandenberghe et al., Naturally occurring singleton residues in AAV capsid impact performance and illustrate structural constraints. Submitted 2007. EMBL/GenBank/DDBJ databases. Accession No. B4Y882_9VIRU.
Yan, Ziying et al. Ubiquitination of both Adeno-Associated Virus Type 2 and 5 Capsid Proteins Affects the Transduction Efficiency of Recombinant Vectors, Journal of Virology 76(5):2043-2053 (Mar. 2002), 11 pages.
Zhong, Li et al., Evaluation of Primitive Murine Hematopoietic Stem and Progenitor Cell Transduction in Vitro and in Vivo by Recombinant Adeno-Associated Virus Vector Serotypes 1 Through 5, Human Gene Therapy 17(3):321-333 (Mar. 2006), 13 pages.
3rd party observation dated Oct. 2, 2012 against EP Application No. 9800733 .9.
Acland et al., "Gene Therapy Restores Vision in a Ccanine Model of Childhood Blindness," *Nat. Genet.*, 28:92-95, May 2001.
Acland et al., "Long Term Restoration of Rod and Cone Vision by Single-Dose rAAV-Mediated Gene Transfer to the Retina in a Canine Model of Childhood Blindness," *Molec. Ther.*, 12(6):1072-1082, Dec. 2005.
Aguirre et al., "Canine and Human Visual Cortex Intact and Responsive Despite Early Retinal Blindness From Rpe65 Mutation," *PLoS Med.*, 4(6):1117-1128, Jun. 2007.

(56) References Cited

OTHER PUBLICATIONS

Allocca et al., "Novel-Adeno-Associated Virus Serotypes Efficiently Transduce Murine Photoreceptors," *J. Virol.*, 81 (20):11372-11380, Oct. 2007.
Aronoff et al., "Controlled and Localized Genetic Manipulations in the Brain," *J. Cell. Molec. Med.*, 10(2):333-352, Apr.-Jun. 2006.
Arrenberg et al., "Optical Control of Zebrafish Behavior with Halorhodopsin," *Proc. Nat'l. Acad. Sci. USA*,106(42):17968-17973, Oct. 2009.
Australian Patent Office Examination Report dated Feb. 20, 2015, Australian Patent Appl. 2009274482, 5 pages.
Baccus, "Timing and Computation in Inner Retinal Circuitry," *Annu. Rev. Physiol.*, 69:271-290, Mar. 2007.
Baron, "Mechanisms of Disease: Neuropathic Pain—A Clinical Perspective," *Nat. Clin. Pract. Neurol.*, 2(2):95-106, Feb. 2006.
Batten et al., "Pharmacological and rAAV Gene therapy Rescue of Visual Functions in a Blind Mouse Model of 0Leber Congenital Amaurosis," *PLoS Med.*, 2(11):1177-1189, Nov. 2005.
Berndt et al., "Bi-Stable Neural State Switches," *Nat. Neurosci.*, 12(2):229-234, Dec. 2008.
Beutler et al., "Intrathecal Gene Transfer by Adeno-Associated Vims for Pain," *Curr. Opin. Molec. Ther.*, 7(5):431-439, Oct. 2005.
Beutler et al., "Retrovirus-Mediated Expression of an Artificial Beta-Endorphin Precursor in Primary Fibroblasts," *J. Neurochem.*, 64:475-481, Feb. 1995.
Bi et al., "Ectopic Expression of a Microbial-Type Rhodopsin Restores Visual Responses in Mice with Photoreceptor Degeneration," *Neuron*, 50(1):23-53, Apr. 2006.
Borras, "Recent Developments in Ocular Gene Therapy," *Exp. Eye Res.*, 76(6):643-652, Jun. 2003.
Bowie et al., "Deciphering the Message in Protein Sequences: Tolerance to Amino Add Substitutions," *Science*, 247(4948):1306-1310, Mar. 1990.
Boyden et al., "Millisecond-Timescale, Genetically Targeted Optical Control of Neural Activity," *Nat. Neurosci.*, 8(9):1263-1628, Sep. 2005.
Canadian Intellectual Property Office, Examination Report dated Oct. 9, 2014, Canadian Patent Appl. 2,762,118, 3 pages.
Canadian Intellectual Property Office, Examination Report of Corresponding Canadian Patent Application No. 2,762,118, dated Aug. 25, 2015 (3 pages).
Carlton et al., "Behavioral Manifestations of an Experimental Model for Peripheral Neuropathy Produced by Spinal Nerve Ligation in the Primate," *Pain*, 56(2):155-166, Feb. 1994.
Casini et al., "Developmental Expression of Neurokinin-1 and Neurokinin-3 Receptors in the Rat Retina," *J. Compar. Neurol.*, 421(2):275-287, May 2000.
Cemazar et al., "Electrically-Assisted Nucleic Acids Delivery to Tissues in Vivo: Where Do We Stand?" *Curr. Pharmaceut. Design*, 12(29):3817-3825, Dec. 2006.
Chader, "Animal Models in Research on Retinal Degenerations: Past Progress and Future Hope," *Vis. Res.*, 42(44:393-399, Feb. 2002.
Chow et al., "High-Performance Genetically Targetable Optical Neural Silencing by Light-Driven Proton Pumps," *Nature*, 463(7277):98-102, Jan. 2010.
Christensen et al., "Spinal Neurons Specifically Excited by Noxious or thermal Stimuli: Marginal Zone of the Dorsal Horn," *J. Neurophysiol.*, 33(2):293-307, Mar. 1970.
Chung et al., "Segmental Spinal Nerve Ligation Model of Neuropathic Pain," *Methods Molec. Med.*, 99:35-45, Jan. 2004.
Congdon et al., "Causes and Prevalence of Visual impairment Among Adults in the United States," *Arch. Ophthalmol.*, 122(4):477-485, Apr. 2004.
De Koning et al., "Methods for Producing a Reproducible Crush in the Sciatic and Tibial Nerve of the Rat and Rapid and Precise Testing of Return of Sensory Function Beneficial Effects of Melanocortins,". *Neurol. Sci.*, 74(2-3):237-246, Jul. 1986.

Dhingra et al., "Light Response of Retinal ON Bipolar Cells Requires a Specific Splice Variant of G[Alpha]O," *J. Neurosci.*, 22(12):4878-4884, Jun. 2002.
Dhingra et al., "The Light Response of ON Bipolar Neurons Requires G[Alpha]O," *J. Neurosci.*, 20(24):9053-9058, Dec. 2000.
Dhingra et al., "Probing Neurochemical Structure and Function of Retinal ON Bipolar Cells with a Transgenic Mouse," *J. Comp. Neurol.*, 510(5):484-496, Oct. 2008.
Dinculescu et al., "Adeno-Associated Virus-Vectored Gene Therapy for Retinal Disease," *Hum. Gene Ther.*, 16(6):649-663, Jun. 2005.
Doroudchi et al., "Virally Delivered Channelrhodopsin-2 Safely and Effectively Restores Visual Function in Multiple Mouse Models of Blindness," *Mol. Ther.*, 19(7):1220-1229, Jul. 2011.
Duvoisin et al., "A Novel Metabotropic Glutamate Receptor Expressed in the Retina and Olfactory Bulb," *J. Neurosci.*, 15(4):3075-3083, Apr. 1995.
European Search Report and Written Opinion dated Dec. 6, 2011 for Application No. 9800733.9.
Finegold et al., "A Paracrine Paradigm for in Vivo Gene therapy in the Central Nervous System: Treatment of Chronic Pain," *Hum. Gene Ther.*, 10(7):1251-1257, May 1999.
Flannery and Greenberg, "Looking Within for Vision," *Neuron*, 50(1):1-3, Apr. 2006.
Fong et al., "The Use and Development of Retroviral Vectors to Deliver Cytokine Genes for Cancer therapy," *Crit. Rev. Ther. Drug Carrier Syst.*, 17(1):1-60, Jan. 2000.
Gao et al., "New Recombinant Serotypes of AAV Vectors," *Curr. Gene Ther.*, 5(3):285-297, Jun. 2005.
Gargini et al., "Retinal Organization in the Retinal Degeneration 10 (rd10) Mutant Mouse: A Morphological and ERG Study," *J. Comp. Neurol.*, 500(2):222-238, Jan. 2007.
Gracely et al., "New Methods of Pain Measurement and their Application to Pain Control," *Int. Dent. J.*, 28(1):52-65, Mar. 1978.
Greenberg et al., "In Vivo Transgene Expression in ON-Type Retinal Ganglion Cells: Applications to Retinal Disease," *Invest. Ophthalmol. Vis. Sci.* 48:E-Abstract 1977, May 2007.
Greener et al., "An Efficient Random Mutagenesis Technique Using an *E. coli* Mutator Strain," *Methods Molec. Biol.*, 1996, 57:375-85, 1996.
Hakki-Onen et al., "Effects of Rapid Eye Movement (REM) Sleep Deprivation on Pain Sensitivity in the Rat," *Brain Res.*, 900(2):261-267, May 2001.
Han and Boyden, "Multiple-Color Optical Activation, Silencing, and Desynchronization of Neural Activity, with Single-Spike Temporal Resolution," *PLoS One*, 2(3):e299. doi: 10.1371/journal.pone. 0000299, Mar. 2007.
Han et al., "Millisecond-Timescale Optical Control of Neural Dynamics in the Nonhuman Primate Brain," *Neuron*, 62(2):191-198, Apr. 2009.
Harrison et al., "Neuronal-Specific and Nerve Growth Factor-Inducible Expression Directed by the Preprotachykinin—A Promoter Delivered by an Adeno-Associated Virus Vector," *Neurosci.*, 94(3):997-1003, Oct. 1999.
Harvey et al., "Intravitreal Injection of Adeno-Associated Viral Vectors Results in the Transduction of Different Types of Retinal Neurons in Neonatal and Adult Rats: a Comparison with Lentiviral Vectors," *Mol. Cell Neurosci.*, 21(1):141-157, Sep. 2002.
Hashimoto et al., "The Whole Nucleotide Sequence and Chromosomal Localization of the Gene for Human Metabotropic Glutamate Receptor Subtype 6," *Eur. J. Neurosci.*, 9(8):1226-1235, Jun. 1997.
Hu and Pathak, "Design of Retroviral Vectors and Helper Cells for Gene Therapy," *Pharmacol. Rev.*, 52(4):493-511, Dec. 2000.
Humayun et al., "Pattern Electrical Stimulation of the Human Retina," *Vision Res.*, 39(15):2569-2576, Jul. 1999.
Hungund and Basavarajappa, "Are Anandamide and Cannabinoid Receptors Involved in Ethanol Tolerance? A Review of the Evidence," *Alcohol & Alcoholism*, 35(2):126-133, Mar.-Apr. 2000.
International Search Report and Written Opinion dated Jun. 26, 2012 for PCT Application No. US2011/056475.
International Search Report and Written Opinion dated Jan. 3, 1920 for PCT Application No. US2009/004453.
International Search Report and Written Opinion dated Nov. 25, 2011 for PCT Application No. 2011/031297.

(56) References Cited

OTHER PUBLICATIONS

Kayser et al., "Differential Anti-Neuropathic Pain Effects of Tetrodotoxin in Sciatic Nerve-Versus Infraorbital Nerve-Ligated Rats—Behavioral, Pharmacological and Immunohistochemical Investigations," *Neuropharmacology*, 58(2):474-487, Feb. 2010.

Kiasalari et al., "Identification of Perineal Sensory Neurons Activated by innocuous Heat," *J. Comp. Neurol.*, 518(2):137-162, Jan. 2010.

Kim et al., "A Core Paired-Type and POU Homeodomain-Containing Transcription Factor Program Drives Retinal Bipolar Cell Gene Expression," *J. Neurosci.*, 28(31):7748-7764, Jul. 2008.

Krebs et al., "Gene Replacement in *Halobacterium halobium* and Expression of Bacteriorhodopsin Mutants," *Proc. Nat'l. Acad. Sci. USA*, 90(5):1987-1991, Mar. 1993.

Krebs et al., "Intramembrane Substitutions in Helix D of Bacteriorhodopsin Disrupt the Purple Membrane," *J. Mol. Biol.*, 267(1):172-183, Mar. 1997.

Lagali et al., "Light-Activated Channels Targeted to ON Bipolar Cells Restore Visual Function in Retinal Degeneration," *Nat. Neurosci.*, 11(6):667-675, Jun. 2008.

Lagali et al., "Targeted Reporter Gene Expression for Morphological and Functional Assessment of Inner Retinal Neurons in Wild-Type and Retinal Degeneration Mice," *Invest. Ophthalmol. Vis. Sci.*, 48:E-Abstract 5944; May 2007.

Le Bars et al., "Animal Models of Nociception," *Pharmacol. Rev.*, 53(4):597-652, Dec. 2001.

Li "Electroporation Gene therapy: New Developments In Vivo and In Vitro," *Curr. Gene Ther.*, 4(3):309-316, Sep. 2004.

Lieber et al., "Integrating Adenovirus-Adeno-Associated Virus Hybrid Vectors Devoid of All Viral Genes," *J. Virol.*, 73(11):9314-9324, Nov. 1999.

Lin et al., "Characterization of Engineered Channelrhodopsin Variants with Improved Properties and Kinetics," *Biophys. J.*, 96(5):1803-1814, Mar. 2009.

Linden et al., "TASK-3 Knockout Mice Exhibit Exaggerated Nocturnal Activity, Impairments in Cognitive Functions, and Reduced Sensitivity to Inhalation Anesthetics," *J. Pharmacol. Exp. Ther.*, 323(3):924-934, Dec. 2007.

Lundstrom, "Alphavirus Vectors: Applications for DNA Vaccine Production and Gene Expression," *Intervirology*, 43(4-6):247-257, Jul.-Dec. 2000.

Maclaren et al., "Retinal Repair by Transplantation of Photoreceptor Precursors," *Nature*, 444:203-207, Nov. 2006.

Marc et al., "Neural Reprogramming in Retinal Degeneration," *Invest. Ophthalmol. Vis. Sci.*, 48(7):3364-3371, Jul. 2007.

Masland, "The Many Roles of Starburst Amacrine Cells," *Trends Neurosci.*, 28(8):395-396, Aug. 2005.

Medeiros and Curcio, "Preservation of Ganglion Cell Layer Neurons in Age-Related Macular Degeneration," *Invest. Ophthalmol. Vis. Sci.*, 42(3):795-803, Mar. 2001.

Melzack and Eisenberg, "Skin Sensory Afterglows," *Science*, 158(3813):445-447, Jan. 1968.

Mendell, "Physiological Properties of Unmyelinated Fiber Projection to the Spinal Cord," *Exp. Neurol.*, 16(3):316-332, Nov. 1966.

Mills and Massey, "All Amacrine Cells Limit Scotopic Acuity in Central Macaque Retina: A Confocal Analysis of Calretinin Labeling," *J. Comp. Neurol.*, 411(1):19-34, Aug. 1999.

Miyoshi et al., "Development of a Self-Inactivating Lentivirus Vector," *J. Virol.*, 72(10):8150-8157, Oct. 1998.

Moore et al., "Peripheral Nerve Injury Promotes a Selective Loss of GABAergic inhibition in the Superficial Dorsal Horn of the Spinal Cord," *J. Neurosci.*, 22(15):6724-6731, Aug. 2002.

Morrison et al., "An Activator Element Within the Preprotachykinin—A Promoter," *Mol. Cell. Neurosci.*, 5(2):165-175, Apr. 1994.

Nawy, "The Metabotropic Receptor mGluR6 May Signal Through G(o), but not Phosphodiesterase, in Retinal Bipolar Cells." *J. Neurosci.*, 19(8):2938-2944, Apr. 1999.

Nagel et al., "Channelrhodopsin-1: A Light-Gated Proton Channel in Green Algae," *Science*, 296(5577):2395-2398, Jun. 2002.

Nagel et al., "Channelrhodopsin-2, A Directly Light-Gated Cation-Selective Membrane Channel," *Proc. Natl. Acad. Sci. USA*, 100(24):13940-13945, Nov. 2003.

Nagel et al., "Channelrhodopsins: Directly Light-Gated Cation Channels," *Biochem. Soc. Trans.*, 33(Pt 4):863-866, Aug. 2005.

Natkunarajah et al., "Assessment of Ocular Transduction Using Single-Stranded and Self-Complementary Recombinant Adeno-Associated Virus Serotype 2/8," *Gene Ther.*, 15(6):463-467, Mar. 2008.

Nichols et al., "Enhancement of the Antiallodynic and Antinociceptive Efficacy of Spinal Morphine by Antisera to Dynorphin A (1-13) or MK-801 in a Nerve-Ligation Model of Peripheral Neuropathy," *Pain*, 69(3):317-322, Feb. 1997.

Palecek et al., "Responses of Spinothalamic Tract Neurons to Mechanical and thermal Stimuli in an Experimental Model of Peripheral Neuropathy in Primates." *J. Neurophysiol.*, 68(6):1951-1966, Dec. 1992.

Pawlyk et al., "Gene Replacement Therapy Rescues Photoreceptor Degeneration in a Murine Model of Leber Congenital Amaurosis Lacking RPGRIP," *Invest. Ophthalmol. Vis. Sci.*, 46(9):3039-3045, Sep. 2005.

Perri et al., "Replicon Vectors Derived from Sindbis Virus and Semliki Forest Virus That Establish Persistent Replication in Host Cells." *J. Virol.*, 74(20):9802-9807, Oct. 2000.

Petrs-Silva et al., "High-Efficiency Transduction of the Mouse Retina by Tyrosine—Mutant AAV Serotype Vectors." *Mol. Thor.*, 17(3):463-471, Mar. 2009.

Puhl and Ikeda, "Identification of the Sensory Neuron Specific Regulatory Region for the Mouse Gene Encoding the Voltage Gated Sodium Channel $Na_v1.8$," *J. Neurochem.*, 106(3):1209-1224, Aug. 2008.

Punzo and Cepko, "Cellular Responses to Photoreceptor Death in the Rd1 Mouse Model of Retinal Degeneration," *Invest. Ophthalmol. Vis. Sci.*, 48(2):849-857, Feb. 2007.

Rakoczy et al., "Mouse Models of Age-Related Macular Degeneration," *Experimental Eye Research*, 82(5):741-752, May 2006.

Reutsky et al., "Patterned Optical Activation of Channelrhodopsin II Expressing Retinal Ganglion Cells," Neural Engineering, CNE '07 3$^{rd}$ Intl. IEEE/EMBS Conf. 50:52, May 2007.

Rex et al., "The Distribution, Concentration, and Toxicity of Enhanced Green Fluorescent Protein in Retinal Cells After Genomic or Somatic (Virus-Mediated) Gene Transfer," *Mol. Vis.*, 11:1236-1245, Dec. 2005.

Rizzo et al., "Perceptual Efficacy of Electrical Stimulation of Human Retina With a Microelectrode Array During Short Term Surgical Trials," *Invest. Ophthalmol. Vis. Sci.*, 44(12):5362-5369, Dec. 2003.

Roska and Werblin, "Vertical interactions Across Ten Parallel, Stacked Representations in the Mammalian Retina." *Nature*, 410:583-587, Mar. 2001.

Scholz et al., "Blocking Caspase Activity Prevents Transsynaptic Neuronal Apoptosis and the Loss of inhibition in Lamina II of the Dorsal Horn After Peripheral Nerve Injury," *J. Neurosci.*, 25(32):7317-7323, Aug. 2005.

Shoda et al., "Increased Phosphorylation of Extracellular Signal-Regulated Kinase in Trigeminal Nociceptive Neurons Following Propofol Administration in Rats." *J. Pain*, 10(5):573-585, Jun. 2009.

Sineshchekov et al., "Two Rhodopsins Mediate Phototaxis to Low- and High-intensity Light in *Chlamydomonas reinhardtii*," *Proc. Natl. Acad. Sci. USA*, 99(13):8689-8694, Jun. 2002.

Smith et al., "Tissue-Specific Regulatory Elements in Mammalian Promoters," *Mol. Syst. Biol.*, 3:73, Jan. 2007.

St. Pierre et al., "Differential Effects of TRPV Channel Block on Polymodal Activation of Rat Cutaneous Nociceptors in Vitro," *Exp. Brain Res.*, 196(1):31-44, Jun. 2009.

Stone et al., "Spinal Analgesic Actions of the New Endogenous Opioid Peptides Endomorphin-1 and -2," *NeuroReport*, 8(14):3131-3135, Sep. 1997.

Strettoi and Pignatelli, "Modifications of Retinal Neurons in a Mouse Model of Retinitis Pigmentosa," *Proc. Nat'l. Acad. Sci. USA*, 97(20):11020-11025, Sep. 2000.

(56) References Cited

OTHER PUBLICATIONS

Taylor and Vaney, "New Directions in Retinal Research," *Trends Neurosci.*, 26(7):379-385, Jul. 2003.
Tian and Kammermeier, "G Protein Coupling Profile of Mglur6 and Expression of G Alpha Proteins in Retinal ON Bipolar Cells," *Vis. Neurosci.*, 23(6):909-916, Nov.-Dec. 2006.
Tomita et al., "Restoration of Visual Response in Aged Dystrophic RCS Rats Using AAV-Mediated Channelopsin-2 Gene Transfer," *Invest. Ophthalmol. Vis. Sci.*, 48(8):3821-3826, Aug. 2007.
Ueda et al., "The mG1uR6 5 Upstream Transgene Sequence Directs a Cell-Specific and Developmentally Regulated Expression in Retinal Rod and ON-Type Cone Bipolar Cells." *J. Neurosci.*, 17(9):3014-3023, May 1997.
Vandaele et al., "Purkinje Cell Protein-2 Regulatory Regions and Transgene Expression in Cerebellar Compartments." *Genes Dev.*, 5(7):1136-1148, Jul. 1991.
Veraart et al., "Vision Rehabilitation in the Case of Blindness." *Expert Rev. Med. Devices*, 1(1):139-153, Sep. 2004.
Vigna and Naldini, "Lentiviral Vectors: Excellent Tools for Experimental Gene Transfer and Promising Candidates for Gene Therapy," *J. Gene Med.*, 2(5):308-316, Sep.-Oct. 2000.
Wan et al., "In Vitro Evolution of Horse Heart Myoglobin to Increase Peroxidase Activity," *Proc. Nat'l Acad. Sci. USA*, 96(22):12525-12831, Oct. 1995.
Wang et al., "Molecular Determinants Differentiating Photocurrent Properties of Two Channelrhodopsins from *Chlamydomonas*," *J. Biol. Chem.*, 284(9):5685-5696, Feb. 2009.
Warrington and Herzog, "Treatment of Human Disease by Adeno-Associated Viral Gene Transfer," *Hum. Genet.*, 119(6):571-603, Jul. 2006.
Wassle, "Parallel Processing in the Mammalian Retina," *Nat. Rev. Neurosci.*, 5:747-757, Oct. 2004.
Weiland et al., "Visual Task Performance in Blind Humans with Retinal Prosthetic Implants," *Conf. Proc. IEEE Eng. Med. Biol. Soc.*, 6:4172-4173, Sep. 2004.
Wen et al., "Exploring the Allowed Sequence Space of a Membrane Protein," *Nat. Struct. Biol.*, 3(2):141-148, Feb. 1996.
Whaley et al., "Selection of Peptides with Semiconductor Binding Specificity for Directed Nanocrystal Assembly," *Nature*, 405:665-668, Jun. 2000.
Winter et al., "Retinal Prostheses: Current Challenges and Future Outlook," *J. Biomater. Sci. Polym. Ed.*, 18(3):1031-1055, Aug. 2007.

Wu et al., "Adeno-Associated Virus Serotypes: Vector Toolkit for Human Gene Therapy," *Mol. Ther.*, 14(3):316-327, Sep. 2006.
Wu et al., "Self-Complementary Recombinant Adeno-Associated Viral Vectors: Packaging Capacity and the Role of Rep Proteins in Vector Purity," *Hum. Gene Ther.*, 18(2):171-182, Feb. 2007.
Yanai et al., "Visual Performance Using a Retinal Prosthesis in Three Subjects with Retinitis Pigmentosa," *Am. J. Ophthalmol.*, 143(5):820-827, May 2007.
Zhang et al., "Multimodal Fast Optical Interrogation of Neural Circuitry," *Nature*, 446:633-639, Apr. 2007.
Zhang et al., "Red-Shifted Optogenetic Excitation: a Tool for Fast Neural Control Derived from *Volvox carteri*," *Nat. Neurosci.*, 11(6):631-633, Jun. 2008.
Zhang et al., "Neurokinin-1 Receptor Enhances TRPV 1 Activity in Primary Sensory Neurons Vla Pkcepsilon: A Novel Pathway for Heat Hyperalgesia," *J. Neurosci.*, 27(44):12067-12077, Oct. 2007.
Zhong et al., "A Dual Role of EGFR Protein Tyrosine Kinase Signaling in Ubiquitination of AAV2 Capsids and Viral Second-Strand DNA Synthesis," *Mol. Ther.*, 15(7):1323-1330, Apr. 2007.
Zhong et al., "Next Generation of Adeno-Associated Virus 2 Vectors: Point Mutations in Tyrosines Lead to High-Efficiency Transduction at Lower Doses," *Proc. Nat'l. Acad. Sci. USA*, 105(22):7827-7832, Jun. 2008.
Gabriel et al., Bioengineering of AAV2 capsid at specific serine, threonine, or lysine residues improves its transduction efficiency in vitro and in vivo. Hum Gene Ther Methods. Apr. 2013;24(2):80-93. doi: 10.1089/hgtb.2012.194. Epub Mar. 15, 2013.
Li et al., Site-Directed Mutagenesis of Surface-Exposed Lysine Residues Leads to Improved Transduction by AAV2, But Not AAV8, Vectors in Murine Hepatocytes in Vivo. Hum Gene Ther Methods. Dec. 2015;26(6):211-20. doi: 10.1089/hgtb.2015.115. Epub Oct. 27, 2015.
Radivojac et al., Identification, analysis, and prediction of protein ubiquitination sites. Proteins. Feb. 1, 2010;78(2):365-80. Author manuscript.
Rakoczy et al., Development of Gene Therapy-Based Strategies for the Treatment of Eye Diseases. Drug Development Research. 1999;46:277-285.
Wang et al., Limitations of encapsidation of recombinant self-complementary adeno-associated viral genomes in different serotype capsids and their quantitation. Hum Gene Ther Methods. Aug. 2012;23(4):225-33. doi: 10.1089/hgtb.2012.090.

* cited by examiner

ChR1

```
   1 GCGTTGCTTG ACTACGCTTC GCTGTAATAA TAGCAGCGCC ACAAGTAGTG TCGCCAAACA
  61 ACTCTCACTT TGAGCTTGAG CACACCGCTG AGCCCCGATC TCGCGGAGGC CATGGCTTCT
 121 TGCCCTAGCG CTGGCAGTGG CGCTGGCGGC CGGCAGCGCA GGAGCCTCGA CTGGCAGTGA
 181 CGCGACGGTG CCGGTCGCGA CTCAGGATGG CCCCGACTAC GTTTTCCACC GTGCCCACGA
 241 GCGCATGCTC TTCCAAACCT CATACACTCT TGAGAACAAT GGTTCTGTTA TTTGCATCCC
 301 GAACAACGGC CAGTGCTTCT GCTTGGCTTG GCTTAAATCC AACGGAACAA ATGCCGAGAA
 361 GTTGGCTGCC AACATTCTGC AGTGGATTAC TTTTGCGCTT TCAGCGCTCT GCCTGATGTT
 421 CTACGGCTAC CAGACCTGGA AGTCTACTTG CGGCTGGGAG GAGATTTACG TGGCCACGAT
 481 CGAGATGATC AAGTTCATCA TCGAGTATTT CCATGAGTTT GACGAACCTG CGGTGATCTA
 541 CTCATCCAAC GGCAACAAGA CCGTGTGGCT TCGTTACGCG GAGTGGCTGC TGACCTGCCC
 601 TGTCATTCTT ATCCATCTGA GCAACCTTAC GGGTCTGGCG AACGACTATA ACAAGCGTAC
 661 CATGGGTCTG CTGGTGTCAG ATATCGGCAC GATCGTGTGG GGCACCACGG CCGCGCTGTC
 721 CAAGGGATAC GTCCGTGTCA TTTTCTTCCT GATGGGCCTG TGCTACGGCA TCTACACATT
 781 CTTCAACGCA GCCAAGGTCT ACATTGAGGC GTACCACACC GTGCCCAAGG GCATTTGCCG
 841 CGACCTGGTC CGCTACCTTG CCTGGCTCTA CTTCTGTTCA TGGGCTATGT TCCCGGTGCT
 901 GTTCCTGCTG GGCCCCGAGG GCTTTGGCCA CATCAACCAA TTCAACTCTG CCATCGCCCA
 961 CGCCATCCTG GACCTTGCCT CCAAGAACGC TTGGAGTATG ATGGGTCACT TTCTGCGTGT
1021 CAAGATCCAC GAGCACATCC TGCTGTACGG CGACATCCGC AAGAAGCAGA AGGTCAACGT
1081 GGCTGGCCAG GAGATGGAGG TGGAGACCAT GGTGCACGAG GAGGACGACG AGACGCAGAA
1141 GGTGCCCACG GCAAAGTACG CCAACCGCGA CTCGTTCATC ATCATGCGCG ACCGCCTCAA
1201 GGAGAAGGGC TTCGAGACCC GCGCCTCGCT GGACGGCGAC CCGAACGGCG ACGCCGAGGC
1261 CAACGCTGCA GCCGGCGGCA AGCCCGGAAT GGAGATGGGC AAGATGACCG GCATGGGCAT
1321 GGGCATGGGT GCCGGCATGG GCATGGCGAC CATCGATTCG GGCCGCGTCA TCCTCGCCGT
1381 GCCGGACATC TCCATGGTGG ACTTTTTCCG CGAGCAGTTC GCGCGGCTGC CCGTGCCCTA
1441 CGAACTGGTG CCCGCGCTGG GCGCGGAGAA CACCCTCCAG CTGGTGCAGC AGGCGCAGTC
1501 ACTGGGAGGC TGCGACTTCG TCCTCATGCA CCCCGAGTTC CTGCGCGACC GCAGTCCCAC
1561 GGGTCTGCTG CCCCGCCTCA AGATGGGCGG GCAGCGCGCC GCGGCCTTCG GCTGGGCGGC
1621 AATCGGCCCC ATGCGGGACT TGATCGAGGG TTCGGGCGTT GACGGCTGGC TGGAGGGCCC
1681 CAGCTTTGGC GCCGGCATCA ACCAGCAGGC GCTGGTGGCG CTGATCAACC GCATGCAGCA
1741 GGCCAAGAAG ATGGGCATGA TGGGCGGTAT GGGTATGGGC ATGGGCGGCG GCATGGGTAT
1801 GGGCATGGGT ATGGGCATGG GCATGGCCCC CAGCATGAAC GCCGGCATGA CTGGCGGCAT
1861 GGGCGGCGCC TCCATGGGCG GTGCCGTGAT GGGCATGGGC ATGGGCATGC AGCCCATGCA
1921 GCAGGCTATG CCGGCCATGT CGCCATGAT GACTCAGCAG CCCAGCATGA TGAGTCAGCC
1981 CTCCGCCATG AGCGCCGGCG GCGCCATGCA GGCCATGGGT GGCGTCATGC CAGCCCCGC
2041 CCCCGGCGGC CGCGTGGGCA CCAACCCGCT GTTTGGCTCT GCGCCCTCTC CGCTGAGCTC
2101 GCAGCCCGGC ATCAGCCCTG GCATGGCGAC GCCGCCCGCC GCCACCGCCG CACCCGCCGC
2161 TGGCGGCAGC GAGGCCGAGA TGCTGCAGCA GCTGATGAGC GAGATCAACC GCCTGAAGAA
2221 CGAGCTGGGC GAGTAA
```

(SEQ ID NO:2)

*FIG. 1*

ChR2

```
   1 GCATCTGTCG CCAAGCAAGC ATTAAACATG GATTATGGAG GCGCCCTGAG TGCCGTTGGG
  61 CGCGAGCTGC TATTTGTAAC GAACCCAGTA GTCGTCAATG GCTCTGTACT TGTGCCTGAG
 121 GACCAGTGTT ACTGCGCGGG CTGGATTGAG TCGCGTGGCA CAAACGGTGC CCAAACGGCG
 181 TCGAACGTGC TGCAATGGCT TGCTGCTGGC TTCTCCATCC TACTGCTTAT GTTTTACGCC
 241 TACCAAACAT GGAAGTCAAC CTGCGGCTGG GAGGAGATCT ATGTGTGCGC TATCGAGATG
 301 GTCAAGGTGA TTCTCGAGTT CTTCTTCGAG TTTAAGAACC CGTCCATGCT GTATCTAGCC
 361 ACAGGCCACC GCGTCCAGTG GTTGCGTTAC GCCGAGTGGC TTCTCACCTG CCCGGTCATT
 421 CTCATTCACC TGTCAAACCT GACGGGCTTG TCCAACGACT ACAGCAGGCG CACCATGGGT
 481 CTGCTTGTGT CTGATATTGG CACAATTGTG TGGGGCGCCA CTTCCGCCAT GGCCACCGGA
 541 TACGTCAAGG TCATCTTCTT CTGCCTGGGT CTGTGTTATG GTGCTAACAC GTTCTTTCAC
 601 GCTGCCAAGG CCTACATCGA GGGTTACCAC ACCGTGCCGA AGGGCCGGTG TCGCCAGGTG
 661 GTGACTGGCA TGGCTTGGCT CTTCTTCGTA TCATGGGGTA TGTTCCCCAT CCTGTTCATC
 721 CTCGGCCCCG AGGGCTTCGG CGTCCTGAGC GTGTACGGCT CCACCGTCGG CCACACCATC
 781 ATTGACCTGA TGTCGAAGAA CTGCTGGGGT CTGCTCGGCC ACTACCTGCG CGTGCTGATC
 841 CACGAGCATA TCCTCATCCA CGGCGACATT CGCAAGACCA CCAAATTGAA CATTGGTGGC
 901 ACTGAGATTG AGGTCGAGAC GCTGGTGGAG GACGAGGCCG AGGCTGGCGC GGTCAACAAG
 961 GGCACCGGCA AGTACGCCTC CCGCGAGTCC TTCCTGGTCA TGCGCGACAA GATGAAGGAG
1021 AAGGGCATTG ACGTGCGCGC CTCTCTGGAC AACAGCAAGG AGGTGGAGCA GGAGCAGGCC
1081 GCCAGGGCTG CCATGATGAT GATGAACGGC AATGGCATGG GTATGGGAAT GGGAATGAAC
1141 GGCATGAACG GAATGGGCGG TATGAACGGG ATGGCTGGCG GCGCCAAGCC CGGCCTGGAG
1201 CTCACTCCGC AGCTACAGCC CGGCCGCGTC ATCCTGGCGG TGCCGGACAT CAGCATGGTT
1261 GACTTCTTCC GCGAGCAGTT TGCTCAGCTA TCGGTGACGT ACGAGCTGGT GCCGGCCCTG
1321 GGCGCTGACA ACACACTGGC GCTGGTTACG CAGGCGCAGA ACCTGGGCGG CGTGGACTTT
1381 GTGTTGATTC ACCCCGAGTT CCTGCGCGAC CGCTCTAGCA CCAGCATCCT GAGCCGCCTG
1441 CGCGGCGCGG GCCAGCGTGT GGCTGCGTTC GGCTGGGCGC AGCTGGGGCC CATGCGTGAC
1501 CTGATCGAGT CCGCAAACCT GGACGGCTGG CTGGAGGGCC CCTCGTTCGG ACAGGGCATC
1561 CTGCCGGCCC ACATCGTTGC CCTGGTGGCC AAGATGCAGC AGATCCGCAA GATGCAGCAG
1621 ATGCAGCAGA TTGGCATGAT GACCGGCGGC ATGAACGGCA TGGGCGGCGG TATGGGCGGC
1681 GGCATGAACG GCATGGGCGG CGGCAACGGC ATGAACAACA TGGGCAACGG CATGGGCGGC
1741 GGCATGGGCA ACGGCATGGG CGGCAATGGC ATGAACGGAA TGGGTGGCGG CAACGGCATG
1801 AACAACATGG GCGGCAACGG AATGGCCGGC AACGGAATGG GCGGCGGCAT GGGCGGCAAC
1861 GGTATGGGTG GCTCCATGAA CGGCATGAGC TCCGGCGTGG TGGCCAACGT GACGCCCTCC
1921 GCCGCCGGCG GCATGGGCGG CATGATGAAC GGCGGCATGG CTGCGCCCCA GTCGCCCGGC
1981 ATGAACGGCG GCCGCCTGGG TACCAACCCG CTCTTCAACG CCGCGCCCTC ACCGCTCAGC
2041 TCGCAGCTCG GTGCCGAGGC AGGCATGGGC AGCATGGGAG GCATGGGCGG AATGAGCGGA
2101 ATGGGAGGCA TGGGTGGAAT GGGGGGCATG GGCGGCGCCG GCGCCGCCAC GACGCAGGCT
2161 GCGGGCGGCA ACGCGGAGGC GGAGATGCTG CAGAATCTCA TGAACGAGAT CAATCGCCTG
2221 AAGCGCGAGC TTGGCGAGTA A
```

(SEQ ID NO:3)

*FIG. 2*

Halorhodopsin (NpHR)

```
  1 ATGACTGAGA CCCTCCCACC CGTGACTGAA AGCGCCGTCG CTCTGCAAGC AGAGGTTACC
 61 CAGCGGGAGC TGTTCGAGTT CGTCCTCAAC GACCCCCTCC TGGCTTCTAG CCTCTACATC
121 AACATGCTCT GGCAGGCCTG TCTATACTGC TGTTCGTCTT CATGACCAGG GGACTCGATG
181 ACCCTAGGGC TAAACTGATT GCAGTGAGCA CAATTCTGGT TCCCGTGGTC TCTATCGCTT
241 CCTACACTGG CTGGCATCTG GTCTCACAAT CAGTGTCCTG GAAATGCCAG CTGGCCACTT
301 TGCCGAAGGG AGTTCTGTCA TGCTGGGAGG CGAAGAGGTC GATGGGGTTG TCACAATGTG
361 GGGTCGCTAC CCACCTGGGC TCTCAGTACC CCATGATCC TGCTGGCACT CGGACTCCTG
421 GCCGGAAGTA ACGCCACCAA ACTCTTCACT GCTATTACAT TCGATATCGC CATGTGCGTG
481 ACCGGGCTCG CAGCTCCCTC ACCACCAGCA GCCATCTGAT GAGATGGTTT TGGTATGCCA
541 TCTCTTGTGC CTGCTTTCTG GTGGTGCTGT ATATCCTGCT GGTGGAGTGG GCTCAGGATG
601 CCAAGGCTGC AGGGACAGCG ACATGTTTAA TACACTGAAG CTGCTCACTG TGGTGATGTG
661 GCTGGGTTAC CCTATCGTTT GGGCACTCGG CGTGGAGGGA ATCGCAGTTC TGCCTGTTGG
721 TGTGACAAGC TGGGGCTACT CCTCCTGGAC ATTGTGGCCA AGTATATTTT TGCCTTTCTG
781 CTGCTGAATT ATCTGACTTC CAATGAGTCC GTGGTGTCCG GCTCCATACT GGACGTGCCA
841 TCCGCCAGCG GCACACCTGC CGATGCTGA
```

(SEQ ID NO:4)

*FIG. 3*

Melanopsin

```
   1 GAGGATCCGC CACCATGAAC CCTCCTTCGG GCCCTAGAGT CCTGCCCAGC CAACCCAAG
  61 AGCCCAGCTG CATGGCCACC CCAGCACCAC CCAGCTGGTG GACAGCTCC CAGAGCAGCA
 121 TCTCCAGCCT GGGCCGGCTT CCATCCATCA GTCCCACAGC ACCTGGGACT TGGGCTGCTG
 181 CCTGGGTCCC CCTCCCCACG GTTGATGTTC CAGACCATGC CCACTATACC CTGGGCACAG
 241 TGATCTTGCT GGTGGGACTC ACGGGCATGC TTGGCAACCT GACGGTCATC TATACCTTCT
 301 GCAGGAGCAG AAGCCTCCGG ACACCTGCCA ACATGTTCAT TATCAACCTC GCGGTCAGCG
 361 ACTTCCTCAT GAGTTTCACC CAGGCCCCTG TCTTCTTCAC CAGTAGCCTC TATAAGCAGT
 421 GGCTCTTTGG GGAGACAGGC TGCGAGTTCT ATGCCTTCTG TGGAGCTCTC TTTGGCATTT
 481 CCTCCATGAT CACCCTGACG GCCATCGCCC TGGACCGCTA CCTGGTAATC ACACGCCCGC
 541 TGGCCACCTT TGGTGTGGCG TCCAAGAGGC GTGCGGCATT TGTCCTGCTG GGCGTTTGGC
 601 TCTATGCGCT AGCTTGGAGT CTGCCACCCT TCTTCGGCTG GAGCGCCTAC GTGCCCGAGG
 661 GGTTGCTGAC ATCCTGCTCC TGGGACTACA TGAGCTTCAC GCCGGCCGTG CGTGCCTACA
 721 CCATGCTTCT CTGCTGCTTC GTGTTCTTCC TCCCTTTATT AATTATCATC TACTGCTACA
 781 TCTTCATCTT CAGGGCCATC CGGGAGACAG GACGGGCTCT CCAGACCTTC GGGGCCTGCA
 841 AGGGCAATGG CGAGTCCCTG TGGCAGCGGC AGCGGCTGCA GAGCGAGTGC AAGATGGCCA
 901 AGATCATGCT GCTGGTCATC CTCCTCTTCG TGCTCTCCTG GGCTCCCTAT TCCGCTGTGG
 961 CCCTGGTGGC CTTTGCTGGG TACGCACACG TCCTGACACC CTACATGAGC TCGGTGCCAG
1021 CCGTCATCGC CAAGGCCTCT GCAATCCACA ACCCCATCAT TTACGCCATC ACCCACCCCA
1081 AGTACAGGGT GGCCATTGCC CAGCACCTGC CCTGCCTAGG TGTGCTGCTG GGTGTATCAC
1141 GCCGGCACAG TCGCCCCTAC CCCAGCTACC GCTCCACCCA CCGCTCCACG CTGACCAGCC
1201 ACACCTCCAA CCTCAGCTGG ATCTCCATAC GGAGGCGCCA GGAGTCCCTG GGCTCGGAGA
1261 GTGAGGTGGG CTGGACACAC ATGGAGGCAG CAGCTGTGTG GGGAGCTGCC CAGCAAGCAA
1321 ATGGGCGGTC CCTCTACGGT CAGGGTCTGG AGGACTTGGA AGCCAAGGCA CCCCCCAGAC
1381 CCCAGGGACA CGAAGCAGAG ACTCCAGGGA AGACCAAGGG GCTGATCCCC AGCCAGGACC
1441 CGCGGATGGG CGGCGGCGAC TACAAGGACG ATGATGACAA GTAATAAGAA TTCAG
```

(SEQ ID NO:5)

*FIG. 4*

ChR2 (mammalian codon-optimized sequence fused with GFP)

```
   1  ATGGACTATG GCGGCGCTTT GTCTGCCGTC GGACGCGAAC TTTTGTTCGT TACTAATCCT
  61  GTGGTGGTGA ACGGGTCCGT CCTGGTCCCT GAGGATCAAT GTTACTGTGC CGGATGGATT
 121  GAATCTCGCG GCACGAACGG CGCTCAGACC GCGTCAAATG TCCTGCAGTG GCTTGCAGCA
 181  GGATTCAGCA TTTTGCTGCT GATGTTCTAT GCCTACCAAA CCTGGAAATC TACATGCGGC
 241  TGGGAGGAGA TCTATGTGTG CGCCATTGAA ATGGTTAAGG TGATTCTCGA GTTCTTTTTT
 301  GAGTTTAAGA ATCCCTCTAT GCTCTACCTT GCCACAGGAC ACCGGGTGCA GTGGCTGCGC
 361  TATGCAGAGT GGCTGCTCAC TTGTCCTGTC ATCCTTATCC ACCTGAGCAA CCTCACCGGC
 421  CTGAGCAACG ACTACAGCAG GAGAACCATG GGACTCCTTG TCTCAGACAT CGGGACTATC
 481  GTGTGGGGGG CTACCAGCGC CATGGCAACC GGCTATGTTA AGTCATCTT CTTTTGTCTT
 541  GGATTGTGCT ATGGCGCGAA CACATTTTTT CACGCCGCCA AGCATATAT CGAGGGTTAT
 601  CATACTGTGC CAAAGGGTCG GTGCCGCCAG GTCGTGACCG GCATGGCATG GCTGTTTTTC
 661  GTGAGCTGGG GTATGTTCCC AATTCTCTTC ATTTTGGGGC CGAAGGTTT TGGCGTCCTG
 721  AGCGTCTATG CTCCACCGT AGGTCACACG ATTATTGATC TGATGAGTAA AAATTGTTGG
 781  GGGTTGTTGG ACACTACCT GCGCGTCCTG ATCCACGAGC ACATATTGAT TCACGGAGAT
 841  ATCCGCAAAA CCACCAAACT GAACATCGGC GGAACGGAGA TCGAGGTCGA GACTCTCGTC
 901  GAAGACGAAG CCGAGGCCGG AGCCGTGCCA GCGGCACCGG TAGTAGCAGT GAGCAAGGGC
 961  GAGGAGCTGT TCACCGGGGT GGTGCCCATC CTGGTCGAGC TGGACGGCGA CGTAAACGGC
1021  CACAAGTTCA GCGTGTCCGG CGAGGGCGAG GGCGATGCCA CCTACGGCAA GCTGACCCTG
1081  AAGTTCATTT GCACCACCGG CAAGCTGCCC GTGCCCTGGC CACCCTCGT GACCACCCTG
1141  ACCTACGGCG TGCAGTGCTT CAGCCGCTAC CCCGACCACA TGAAGCAGCA CGACTTCTTC
1201  AAGTCCGCCA TGCCCGAAGG CTACGTCCAG GAGCGCACCA TCTTCTTCAA GGACGACGGC
1261  AACTACAAGA CCCGCGCCGA GGTGAAGTTC GAGGGCGACA CCCTGGTGAA CCGCATCGAG
1321  CTGAAGGGCA TCGACTTCAA GGAGGACGGC AACATCCTGG GCACAAGCT GGAGTACAAC
1381  TACAACAGCC ACAACGTCTA TATCATGGCC GACAAGCAGA AGAACGGCAT CAAGGTGAAC
1441  TTCAAGATCC GCCACAACAT CGAGGACGGC AGCGTGCAGC TCGCCGACCA CTACCAGCAG
1501  AACACCCCCA TCGGCGACGG CCCCGTGCTG CTGCCCGACA ACCACTACCT GAGCACCCAG
1561  TCCGCCCTGA GCAAAGACCC CAACGAGAAG CGCGATCACA TGGTCCTGCT GGAGTTCGTG
1621  ACCGCCGCCG GGATCACTCT CGGCATGGAC GAGCTGTACA AGTAA
```

(SEQ ID NO:6)

FIG. 5

GRM60

```
  1 ATCTCCAGAT GGCTAAACTT TTAAATCATG AATGAAGTAG ATATTACCAA ATTGCTTTTT
 61 CAGCATCCAT TTAGATAATC ATGTTTTTTG CCTTTAATCT GTTAATGTAG TGAATTACAG
121 AAATACATTT CCTAAATCAT TACATCCCCC AAATCGTTAA TCTGCTAAAG TACATCTCTG
181 GCTCAAACAA GACTGGTTG
```

(SEQ ID NO:7)

*FIG. 6*

*smCBA*

```
  1 AATTCGGTAC CCTAGTTATT AATAGTAATC AATTACGGGG TCATTAGTTC ATAGCCCATA
 61 TATGGAGTTC CGCGTTACAT AACTTACGGT AAATGGCCCG CCTGGCTGAC CGCCCAACGA
121 CCCCCGCCCA TTGACGTCAA TAATGACGTA TGTTCCCATA GTAACGCCAA TAGGGACTTT
181 CCATTGACGT CAATGGGTGG ACTATTTACG GTAAACTGCC CACTTGGCAG TACATCAAGT
241 GTATCATATG CCAAGTACGC CCCCTATTGA CGTCAATGAC GGTAAATGGC CCGCCTGGCA
301 TTATGCCCAG TACATGACCT TATGGGACTT TCCTACTTGG CAGTACATCT ACGTATTAGT
361 CATCGCTATT ACCATGGTCG AGGTGAGCCC CACGTTTGCT TCACTCTCCC CATCTCCCCC
421 CCCTCCCCAC CCCCAATTTT GTATTTATTT ATTTTTAAT TATTTGTGC AGCGATGGGG
481 GCGGGGGGGG GGGGGGGGCG CGCGCCAGGC GGGGCGGGGC GGGGCGAGGG GCGGGGCGGG
541 GCGAGGCGGA GAGGTGCGGC GGCAGCCAAT CAGAGCGGCG CGCTCCGAAA GTTTCCTTTT
601 ATGGCGAGGC GGCGGCGGCG GCGGCCCTAT AAAAAGCGAA GCGCGCGGCG GGCGGGAGTC
661 GCTGCGACGC TGCCTTCGCC CCGTGCCCCG CTCCGCCGCC GCCTCGCGCC GCCCGCCCCG
721 GCTCTGACTG ACCGCGTTAC TCCCACAGGT GAGCGGGCGG GACGGCCCTT CTCCTCCGGG
781 CTGTAATTAG CGCTTGGTTT AATGACGGCT TGTTTCTTTT CTGTGGCTGC GTGAAAGCCT
841 TGAGGGGCTC CGGGAGCTAG AGCCTCTGCT AACCATGTTC ATGCCTTCTT CTTTTTCCTA
901 CAGCTCCTGG GCAACGTGCT GGTTATTGTG CTGTCTCATC ATTTTGGCAA AG
```

(SEQ ID NO:8)

*FIG. 7*

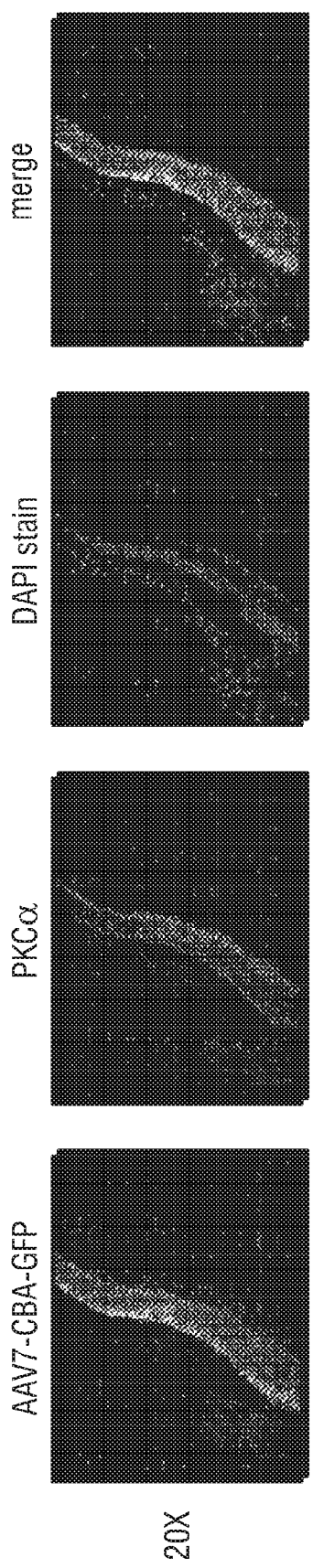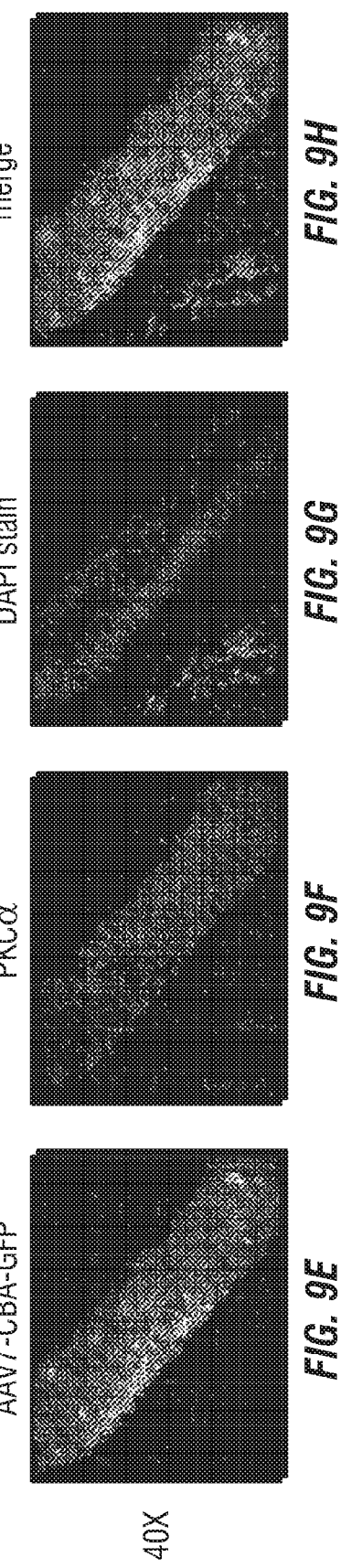

CAPSID-MUTATED RAAV VECTORS AND METHODS OF USE

CROSS-REFERENCE TO RELATED APPLICATIONS

The present application is a continuation of U.S. patent application Ser. No. 14/298,533, filed Jun. 6, 2014 (pending), which is a continuation-in-part of U.S. patent application Ser. No. 12/993,092, filed Jun. 10, 2011 (now abandoned), which was the U.S. national-stage filing of PCT Intl. Pat. Appl. No. PCT/US2009/044753, filed May 20, 2009 (now abandoned); which claims priority to U.S. Prov. Pat. Appl. No. 61/054,571, filed May 20, 2008; U.S. Prov. Pat. Appl. No. 61/199,241, filed Nov. 14, 2008; and U.S. Prov. Pat. Appl. No. 61/200,430, filed Nov. 26, 2008; the contents of each of which is specifically incorporated herein in its entirety by express reference thereto.

STATEMENT REGARDING FEDERALLY SPONSORED RESEARCH OR DEVELOPMENT

This invention was made with government support under Grant Nos. DK-058327 GM-082946, HL-076901, and HL-097088 awarded by the National Institutes of Health. The government has certain rights in the invention.

NAMES OF THE PARTIES TO A JOINT RESEARCH AGREEMENT

Not Applicable.

BACKGROUND OF THE INVENTION

Field of the Invention

The present disclosure relates to the fields of molecular biology, ophthalmology, and gene therapy. In particular embodiments, capsid-mutated rAAV vectors and methods for their use in gene therapy are disclosed. In exemplary embodiments, capsid proteins comprising a modification of one or more of the surface-exposed tyrosine residues are disclosed, including VP3 capsid proteins that include tyrosine-to-phenylalanine mutations at positions corresponding to Y444F, Y500F, and Y730F of the wild-type AAV2 sequence. Also provided are rAAV virions and viral particles that comprise such a mutated AAV capsid protein and a nucleic acid molecule that expresses one or more selected therapeutic or reporter transgenes in one or more mammalian cells of interest.

Description of Related Art

A gene-delivery therapy to treat a disease or disorder independent of treating an underlying mutation could have potential value. Methods capable of controlling, regulating, and/or driving specific neural circuits so as to mediate naturalistic neural responses and high resolution perception and control could also be of enormous potential therapeutic value. Neurons are an example of a type of cell that uses the electrical currents created by depolarization to generate communication signals (e.g., nerve impulses). Other electrically excitable cells include skeletal muscle, cardiac muscle, and endocrine cells. Neurons use rapid depolarization to transmit signals throughout the body and for various purposes, such as motor control (e.g., muscle contractions), sensory responses (e.g., touch, hearing, and other senses) and computational functions (e.g., brain functions). By facilitating or inhibiting the flow of positive or negative ions through cell membranes, the cell can be briefly depolarized, depolarized and maintained in that state, or hyperpolarized. Thus, the control of the depolarization of cells can be beneficial for a number of different purposes, including visual, muscular and sensory control. Light-sensitive protein channels, pumps, and receptors can permit millisecond-precision optical control of cells. Although light-sensitive proteins in combination with light can be used to control the flow of ions through cell membranes, targeting and delivery remain to be addressed for specific diseases, disorders, and circuits.

BRIEF SUMMARY OF THE INVENTION

In one aspect, the invention provides a recombinant nucleic acid comprising a nucleic acid encoding a light-sensitive protein operatively linked to a metabotropic glutamate receptor 6 (mGluR6) regulatory sequence or fragment thereof. In one embodiment, the light-sensitive protein can be selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof. In another embodiment the light-sensitive protein is ChR2 or a light-sensitive protein that is at least about 70%, at least about 80%, at least about 90% or at least about 95% identical to ChR2. In another embodiment the mGluR6 regulatory sequence fragment comprises less than about 1000, less than about 750, less than about 500, less than about 250, or less than about 100 base pairs. In a related embodiment, the mGluR6 regulatory sequence or fragment thereof is a mGluR6 promoter or enhancer. In a specific related embodiment, the nucleic acid further comprises a sequence that encodes a green fluorescent protein. In another embodiment, the nucleic acid is encapsidated within a recombinant adeno-associated virus (AAV). In certain embodiments, the recombinant AAV is of a combinatorial hybrid of 2, 3, 4, 5, 6, 7, 8, 9, 10, 11, 12, 13, 14, 15 or more serotypes or mutants thereof. In certain embodiments, the recombinant adeno-associated virus is of a serotype selected from the group consisting of AAV1, AAV2, AAV3, AAV4, AAV5, AAV6, AAV7, AAV8, AAV9, AAV10, AAV11, AAV12, and hybrids thereof. In a related embodiment, the nucleic acid is encapsidated within a recombinant virus selected from the group consisting of recombinant adeno-associated virus (AAV), recombinant retrovirus, recombinant lentivirus, and recombinant poxvirus.

In another aspect, the invention provides a vector comprising a nucleic acid encoding a light-sensitive protein, wherein the nucleic acid is operatively linked to a metabotropic glutamate receptor 6 (mGluR6) regulatory sequence or fragment thereof. In one embodiment, the light-sensitive protein is selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof. In a related embodiment the light-sensitive protein is ChR2 or a light-sensitive protein that is at least about 70%, at least about 80%, at least about 90% or at least about 95% identical to ChR2. In another embodiment, the mGluR6 regulatory sequence fragment is less than about 1000, less than about 750, less than about 500, less than about 250, or less than about 100 base pairs. In a related embodiment, the mGluR6 regulatory sequence fragment is represented by the sequence in FIG. 6. In another embodiment the vector comprises an adeno-associated virus (AAV). In a related embodiment the vector comprises a recombinant virus selected from the group consisting of a recombinant adeno-associated virus (rAAV), a recombinant retrovirus, a recombinant lentivirus, and a recombinant poxvirus. In a specific embodiment, the AAV is of a serotype selected from the group consisting of AAV1, AAV2, AAV3, AAV4, AAV5, AAV6, AAV7, AAV8, AAV9, AAV10, AAV11, AAV12, and hybrids thereof. In other specific embodiments, the recombinant AAV is of a combinatorial hybrid of 2, 3, 4, 5, 6, 7, 8, 9, 10, 11, 12, 13, 14, 15 or more serotypes or mutants thereof. In a related embodiment, the AAV comprises mutated capsid protein. In one specific embodiment, the capsid protein comprises at least one mutated tyrosine residue. The mutated tyrosine residue can be selected from the group consisting of Y252F, Y272F, Y444F, Y500F, Y700F, Y704F, Y730F, Y275F, Y281F, Y508F, Y576F, Y612G, Y673F, and Y720F. In a specific embodiment, the mutated capsid protein comprises one or more tyrosine residues, each mutated to a phenylalanine residue.

In another aspect the present invention provides a method of treating a subject suffering from a disease or disorder of the eye comprising introducing into an affected eye a rAAV vector comprising a light-sensitive protein operatively linked to a metabotropic glutamate receptor 6 regulatory sequence (mGluR6) or fragment thereof. In one embodiment, the disease or disorder of the eye is caused by photoreceptor cell degeneration. In another embodiment, the light-sensitive protein is selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof. In a related embodiment, the light-sensitive protein is ChR2 or a light-sensitive protein that is at least about 70%, at least about 80%, at least about 90% or at least about 95% identical to ChR2. In another embodiment, the mGluR6 promoter fragment is less than about 1000, less than about 750, less than about 500, less than about 250, or less than about 100 base pairs. In a related embodiment, the mGluR6 promoter fragment is represented by the sequence in FIG. 6.

In another embodiment, the AAV is of a serotype selected from the group consisting of AAV1, AAV2, AAV3, AAV4, AAV5, AAV6, AAV7, AAV8, AAV9, AAV10, AAV11, AAV12, and hybrids thereof. In other embodiments, the recombinant AAV is of a combinatorial hybrid of 2, 3, 4, 5, 6, 7, 8, 9, 10, 11, 12, 13, 14, 15 or more serotypes or mutants thereof. In a related embodiment, the AAV comprises a mutated capsid protein. In another related embodiment, the capsid protein comprises a mutated tyrosine residue. In a specific embodiment, the mutated tyrosine residue is selected from the group consisting of Y252F, Y272F, Y444F, Y500F, Y700F, Y704F, Y730F, Y275F, Y281F, Y508F, Y576F, Y612G, Y673F and Y720F. In a related embodiment, the mutated capsid protein comprises a tyrosine residue mutated to a phenylalanine. In another embodiment, the AAV is introduced using intravitreal injection, subretinal injection and/or ILM peel. In a specific embodiment, the AAV is introduced into a retinal bipolar cell (e.g., ON or OFF retinal bipolar cells; rod and cone bipolar cells). In another embodiment, the method further comprises using a light-generating device external to the eye.

In another aspect the present invention provides a method of expressing an exogenous nucleic acid in a retinal bipolar cell (e.g., ON or OFF retinal bipolar cells; rod and cone bipolar cells) comprising introducing into a retina a vector comprising the exogenous nucleic operatively linked to a retinal bipolar (e.g., ON or OFF retinal bipolar cells; rod and cone bipolar cells) cell-specific regulatory sequence wherein the method results in at least about a 25-30% transduction efficiency. In other embodiment, such method results in at least about a 10% transduction efficiency. In one embodiment, the method results in at least about 20%, 30%, 40%, 50%, 60%, 70%, 80%, or 90% transduction efficiency.

In a related embodiment, the transduction efficiency is measured by quantifying the total number of retinal bipolar cells (e.g., ON or OFF retinal bipolar cells; rod and cone bipolar cells) infected. In another embodiment, the exogenous nucleic acid comprises a light-sensitive protein. In a related embodiment, the light-sensitive protein is selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof. In a specific embodiment, the light-sensitive protein is ChR2 or a light-sensitive protein that is at least about 70%, at least about 80%, at least about 90% or at least about 95% identical to ChR2.

In another embodiment, the regulatory sequence comprises a metabotropic glutamate receptor 6 regulatory sequence (mGluR6) or a fragment thereof. In a related embodiment, the mGluR6 regulatory sequence fragment is less than about 1000, less than about 750, less than about 500, less than about 250, or less than about 100 base pairs. In a specific embodiment, the mGluR6 regulatory sequence fragment is represented by the sequence in FIG. 6. In another embodiment, the exogenous nucleic acid is introduced using a recombinant adeno-associated viral vector (AAV). In a related embodiment the AAV comprises a mutated capsid protein. In a specific embodiment, the capsid protein comprises a mutated tyrosine residue. In a related embodiment, the mutated tyrosine residue is selected from the group consisting of Y252F, Y272F, Y444F, Y500F, Y700F, Y704F, Y730F, Y275F, Y281F, Y508F, Y576F, Y612G, Y673F and Y720F. In another embodiment the mutated capsid protein comprises a tyrosine residue mutated to a phenylalanine.

In another embodiment, the exogenous nucleic acid is introduced using intravitreal injection, subretinal injection, and/or ILM peel. In another embodiment, the AAV is of a serotype is selected from the group consisting of AAV1, AAV2, AAV3, AAV4, AAV5, AAV6, AAV7, AAV8, AAV9, AAV10, AAV11, AAV12, and hybrids thereof. In yet another embodiments, the recombinant AAV is of a combinatorial hybrid of 2, 3, 4, 5, 6, 7, 8, 9, 10, 11, 12, 13, 14, 15, or more serotypes, or mutants thereof.

In yet another aspect, the present invention provides a method of introducing an exogenous nucleic acid into the nucleus of a retinal cell comprising introducing a vector comprising an exogenous nucleic acid operatively linked to a retinal cell-specific regulatory sequence into a retinal cell, wherein the vector is specifically designed to avoid ubiquitin-mediated protein degradation. In one embodiment, the degradation is proteasome-mediated. In another embodiment, the exogenous nucleic acid comprises a light-sensitive protein. In a related embodiment, the light-sensitive protein is selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof. In another related embodiment, the light-sensitive protein is ChR2 or a light-sensitive protein that is at least about 70%, at least about 80%, at least about 90% or at least about 95% identical to ChR2. In another embodiment, the retinal cell is a retinal bipolar cell (e.g., ON or OFF retinal bipolar cells; rod and cone bipolar cells).

In a related embodiment, the regulatory sequence comprises a metabotropic glutamate receptor 6 promoter (mGluR6 promoter) or fragment thereof. In another embodiment, the mGluR6 fragment is less than 1000, 750, 500, 250, or 100 base pairs. In another embodiment, the mGluR6 promoter fragment is represented by the sequence in FIG. 6. In another embodiment, the vector is selected from the group consisting of recombinant adeno-associated virus (AAV), recombinant retrovirus, recombinant lentivirus, and recombinant poxvirus. In a related embodiment, the vector is a recombinant adeno-associated viral vector (AAV). In another embodiment, the AAV is of a serotype selected from the group consisting of AAV1, AAV2, AAV3, AAV4, AAV5, AAV6, AAV7, AAV8, AAV9, AAV10, AAV11, AAV12, and hybrids thereof. In other embodiments, the recombinant AAV is of a combinatorial hybrid of 2, 3, 4, 5, 6, 7, 8, 9, 10, 11, 12, 13, 14, 15, or more serotypes, or mutants thereof.

In another embodiment, the AAV comprises a mutated capsid protein. In another embodiment, the capsid protein comprises a mutated tyrosine residue. In another embodiment, the mutated tyrosine residue is selected from the group consisting of Y252F, Y272F, Y444F, Y500F, Y700F, Y704F, Y730F, Y275F, Y281F, Y508F, Y576F, Y612G, Y673F and Y720F. In another embodiment, the mutated capsid protein comprises a tyrosine residue mutated to a phenylalanine. In another embodiment, the vector is introduced using intravitreal injection, subretinal injection, and/or ILM peel.

In another aspect the present invention provides a method of transducing a retinal bipolar cell (e.g., ON or OFF retinal bipolar cells; rod and cone bipolar cells) comprising introducing into a retina a vector comprising an exogenous nucleic acid operatively linked to a regulatory sequence. In one embodiment, the regulatory sequence is a non-cell type specific promoter. In another embodiment, the regulatory sequence is a guanine nucleotide binding protein alpha activating activity polypeptide O (GNAO1) promoter or a fusion of the cytomegalovirus (CMV) immediate early enhancer and the bovine β-actin promoter plus intronl-exon1 junction (CBA, smCBA). In another embodiment, the exogenous nucleic acid comprises a light-sensitive protein. In a related embodiment, the light-sensitive protein is selected from the group consisting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof. In another related embodiment, the light-sensitive protein is ChR2 or a light-sensitive protein that is at least about 70%, at least about 80%, at least about 90% or at least about 95% identical to ChR2.

In another embodiment, the vector is selected from the group consisting of recombinant adeno-associated virus (AAV), recombinant retrovirus, recombinant lentivirus, and recombinant poxvirus. In a related embodiment, the vector is a recombinant adeno-associated viral vector (AAV). In another embodiment, the AAV is of a serotype selected from the group consisting of AAV1, AAV2, AAV3, AAV4, AAV5, AAV6, AAV7, AAV8, AAV9, AAV10, AAV11, AAV12, and hybrids thereof. In certain embodiments, the recombinant AAV is of a combinatorial hybrid of 2, 3, 4, 5, 6, 7, 8, 9, 10, 11, 12, 13, 14, 15 or more serotypes or mutants thereof. In a related embodiment, the AAV comprises a mutated capsid protein. In another embodiment, the capsid protein comprises a mutated tyrosine residue. In another embodiment, the mutated tyrosine residue is selected from the group consisting of Y252F, Y272F, Y444F, Y500F, Y700F, Y704F, Y730F, Y275F, Y281F, Y508F, Y576F, Y612G, Y673F and Y720F. In another embodiment, the mutated capsid protein comprises a tyrosine residue mutated to a phenylalanine. In another embodiment, the vector is introduced using intravitreal injection, subretinal injection, and/or ILM peel.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts the ChR1 nucleic acid sequence (SEQ ID NO:2);

FIG. 2 depicts the ChR2 nucleic acid sequence (SEQ ID NO:3);

FIG. 3 depicts the NpHR nucleic acid sequence (SEQ ID NO:4);

FIG. 4 depicts the melanopsin nucleic acid sequence (SEQ ID NO:5);

FIG. 5 depicts the ChR2 nucleic acid sequence that is mammalian codon-optimized and that encodes a ChR2 fused with Green Fluorescent Protein (GFP) (SEQ ID NO:6);

FIG. 6 depicts a fragment of the GRM6 (metabotropic glutamate receptor 6) regulatory nucleic acid sequence capable of regulating expression in a bipolar cell specific manner (SEQ ID NO:7);

FIG. 7 depicts a smCBA regulatory nucleic acid sequence (SEQ ID NO:8);

(FIG. 8A) Neurons expressing ChR2 with light stimulation; (FIG. 8B) Neurons firing in response to fast trains of blue light pulses;

FIG. 9A, FIG. 9B, FIG. 9C, FIG. 9D, FIG. 9E, FIG. 9F, FIG. 9G, and FIG. 9H depict AAV delivery to retinal bipolar cells. Column 1 shows GFP expression in retinal bipolar cells after a subretinal injection with the AAV7-CBA-GFP vector after 8 weeks of age. Column 2 shows PKCα staining (an antibody that is specific to bipolar cells). Column 3 shows DAPI staining for cell nuclei. Column 4 shows merged images of GFP expression, PKCα and DAPI stains. The first row is 20× magnification and the second row is 40× magnification;

FIG. 12A-1, FIG. 12A-2, FIG. 12B, and FIG. 12C depict training mice on a water maze task. (FIG. 12A-1 and FIG. 12A-2) A schematic (FIG. 12A-1) of the water maze (FIG. 12A-2) used to measure scotopic threshold (Hayes and Balkema, 1993). (FIG. 12B) Time it took each mouse group (retinal degenerated—treated, retinal degenerated—untreated, and wild type) to find the target (black platform+ LED array) as a function of training sessions. (FIG. 12C) Time it took each mouse group (treated rd1, treated rd16, treated rho$^{-/-}$, untreated retinal degenerated, and wild type) to find the target (black platform+LED array) as a function of different light intensities.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Light-Sensitive Proteins:

The present invention provides recombinant nucleic acids encoding light-sensitive proteins, viral and non-viral vectors for the delivery of recombinant nucleic acids encoding light-sensitive proteins, and methods for delivery of light-sensitive proteins.

Light-sensitive proteins are proteins that belong to the opsin family and include vertebrate (animal) and invertebrate rhodopsins. The animal opsins, rhodopsins, are G-protein coupled receptors (GPCRs) with seven transmembrane helices that can regulate the activity of ion channels. Invertebrate rhodopsins are usually not GPCRs, but instead are light-sensitive, or light-activated, ion pumps or ion channels.

An algal opsin such as channelrhodopsin (ChR2) from *Chlamydomonas reinhardtii* allows blue light-induced action potentials to be triggered with millisecond-precision in cells due to depolarizing cation flux through a light-gated pore. An archaeal opsin, such as halorhodopsin from *Natronomonas pharaonis*, allows for light-activated chloride pumping; the pump can be hyperpolarized and inhibited from firing action potentials when exposed to yellow light. Use of such light-sensitive opsins allows for temporal and spatial regulation of neuronal firing activity.

As referred to herein, a "light-sensitive" protein includes channelrhodopsins (ChR1, ChR2), halorhodopsins (NpHR), melanopsins, pineal opsins, bacteriorhodopsin, and variants thereof. A light-sensitive protein of this invention can occur naturally in plant, animal, archaebacterial, algal, or bacterial cells, or can alternatively be created through laboratory techniques.

Figures 1, 12A:
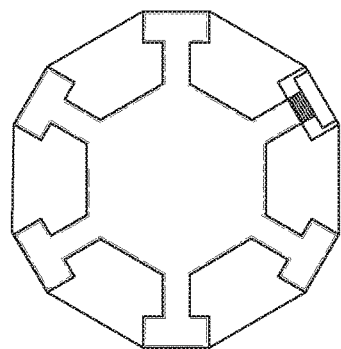
Figures 2, 12A:
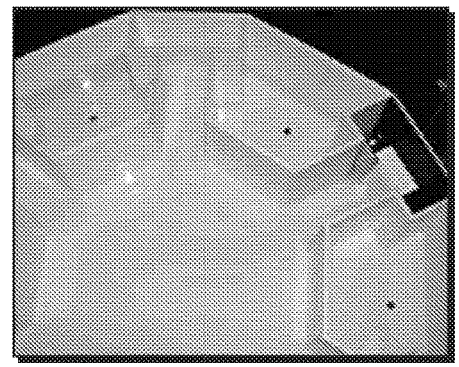

Channelrhodopsins ChR1 (GenBank accession number AB058890/AF385748; FIG. 1) (SEQ ID NO:2) and ChR2 (GenBank accession number AB058891/AF461397; FIG. 2) (SEQ ID NO:3) are two rhodopsins from the green alga, *Chlamydomonas reinhardtii* (Nagel, 2002; Nagel, 2003). Both are light-sensitive channels that, when expressed and activated in neural tissue, allow a cell to be depolarized when stimulated with light (Boyden, 2005).

In some embodiments, hybrid or chimeric channelrhodopsins can be created and used by combining different portions of the ChR1 and ChR2 proteins.

In one embodiment, a hybrid or chimeric channelrhodopsin can be created and used by replacing the N-terminal segments of ChR2 with the homologous counterparts of ChR1 (and vice-versa). In some embodiments, the hybrid channelrhodopsins result in a shift of sensitivity into a different wavelength spectrum (for example, into the red wavelength spectrum) with negligible desensitization and slowed turning-on and turning-off kinetics.

In another embodiment, a ChR1 (amino acids 1-345) and ChR2 (amino acids 1-315) hybrid/chimera can be created and used.

In yet another embodiment, ChR1-ChR2 hybrids/chimeras retaining the N-terminal portion of ChR1 and replacing the C-terminal portion with the corresponding ChR2 segment can be created and used. In specific embodiments, hybrids/chimeras of ChR1 and ChR2 can be constructed and utilized including mutant residues around the retinal binding pockets of the chimeras. In exemplary embodiments, the following chimeras can be created and used:

(a). ChD: a hybrid/chimera of a ChR1 N-terminal portion and a ChR2 C-terminal portion where the crossover site is at a point of homology at helixD of the two channelrhodopsins;

(b). ChEF: a hybrid/chimera of a ChR1 N-terminal portion and a ChR2 C-terminal portion where the crossover site is at the loop between helices E and F of the two channelrhodopsins;

(c). ChIEF: a variant of the ChEF chimera with isoleucine 170 mutated to valine; or (d). ChF: a hybrid/chimera of a ChR1 N-terminal portion and a ChR2 C-terminal portion where the crossover site is at the end of helix F of the two channelrhodopsins.

In some embodiments, the chimeras retain the reduced inactivation of ChR1 in the presence of persistent light, but can allow the permeation of sodium and potassium ions in addition to protons. In other embodiments, the chimeras can improve the kinetics of the channel by enhancing the rate of the channel closure after stimulation.

In some embodiments, other ChR1 and ChR2 variants can be engineered. In specific embodiments, single or multiple point mutations to the ChR2 protein can result in ChR2 variants. In exemplary embodiments, mutations at the C128 location of ChR2 can result in altered channel properties. In related embodiments, C128A, C128S, and C128T ChR2 mutations can result in greater overall mean open times (Berndt, 2009). In other related embodiments, ChR2 variants can result in altered kinetics.

In another embodiment, a VChR1 can be used (GenBank accession number EU622855).

In specific embodiments, a mammalian codon-optimized version of ChR2 is utilized (FIG. 5) (SEQ ID NO:6).

NpHR (Halorhodopsin) (GenBank accession number EF474018; FIG. 3) (SEQ ID NO:4) is from the haloalkaliphilic archaeon, *Natronomonas pharaonis*. In certain embodiments, variants of NpHR can be created. In specific embodiments single or multiple point mutations to the NpHR protein can result in NpHR variants. In specific embodiments, a mammalian codon optimized version of NpHR can be utilized.

In one embodiment, NpHR variants are utilized. In one specific embodiment, eNpHR (enhanced NpHR) is utilized. Addition of the amino acids FCYENEV (SEQ ID NO:1) to the NpHR C-terminus along with the signal peptide from the β-subunit of the nicotinic acetylcholine receptor to the NpHR N-terminus results in the construction of eNpHR.

Melanopsin (GenBank accession number 6693702; FIG. 4) (SEQ ID NO:5) is a photopigment found in specialized photosensitive ganglion cells of the retina that are involved in the regulation of circadian rhythms, pupillary light reflex, and other non-visual responses to light. In structure, melanopsin is an opsin, a retinylidene protein variety of G-protein-coupled receptor. Melanopsin resembles invertebrate opsins in many respects, including its amino acid sequence, and downstream signaling cascade. Like invertebrate opsins, melanopsin appears to be a bi-stable photopigment, with intrinsic photoisomerase activity. In certain embodiments, variants of melanopsin can be created. In specific embodiments, single or multiple point mutations in the melanopsin protein can result in melanopsin variants.

Light-sensitive proteins may also include proteins that are at least about 10%, at least about 20%, at least about 25%, at least about 30%, at least about 35%, at least about 40%, at least about 45%, at least about 50%, at least about 55%, at least about 60%, at least about 70%, at least about 80%, at least about 90%, at least about 95%, or at least about 99% identical to the light-sensitive proteins ChR1, ChR2, NpHR, and melanopsin. For example, the ChR2 protein may include proteins that are at least about 60%, at least about 70%, at least about 80%, at least about 90% or at least about 95% identical to ChR2. In addition, these proteins may include ChR2 that is photosensitive and can be activated by specific wavelengths of high intensity light.

In some embodiments, light-sensitive proteins can modulate signaling within neural circuits and bidirectionally control behavior of ionic conductance at the level of a single neuron. In some embodiments, the neuron is a retinal neuron, a retinal bipolar cell (e.g., ON or OFF retinal bipolar cells; rod and cone bipolar cells), a retinal ganglion cell, a photoreceptor cell, or a retinal amacrine cell.

Adeno-Associated Viral Vectors:

The present invention provides viral vectors comprising nucleic acids encoding a light-sensitive proteins and methods of use, as described herein.

Adeno-associated virus (AAV) is a small (25-nm), non-enveloped virus that packages a linear single-stranded DNA genome of 4.7 Kb. The small size of the AAV genome and concerns about potential effects of Rep on the expression of cellular genes led to the construction of AAV vectors that do not encode Rep and that lack the cis-active IEE, which is required for frequent site-specific integration. The ITRs are kept because they are the cis signals required for packaging. Thus, current recombinant AAV (rAAV) vectors persist primarily as extrachromosomal elements.

A variety of recombinant adeno-associated viral vectors (rAAV) may be used to deliver genes of interest to a cell and to effect the expression of a gene of interest, e.g., a gene encoding a light-sensitive protein. For example, rAAV can be used to express light-sensitive proteins, e.g., ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof or any light-sensitive protein described herein, in a target cell. At times herein, "transgene" is used to refer to a polynucleotide encoding a polypeptide of interest, wherein the polynucleotide is encapsidated in a viral vector (e.g., rAAV).

Adeno-associated viruses are small, single-stranded DNA viruses, which require helper virus to facilitate efficient replication. The 4.7-kb genome of AAV is characterized by two inverted terminal repeats (ITR) and two open reading frames, which encode the Rep proteins and Cap proteins, respectively. The Rep reading frame encodes four proteins of molecular weight 78 kDa, 68 kDa, 52 kDa, and 40 kDa. These proteins function mainly in regulating AAV replication, and rescue and integration of the AAV into a host cell's chromosomes. The Cap reading frame encodes three structural proteins of molecular weight 85 kDa (VP1), 72 kDa (VP2), and 61 kDa (VP3) (Berns), which form the virion capsid. More than 80% of total proteins in AAV virion comprise VP3.

The genome of rAAV is generally comprised of: (1) a 5' adeno-associated virus ITR, (2) a coding sequence (e.g., transgene) for the desired gene product (e.g., a light-sensitive protein) operatively linked to a sequence that regulates its expression in a cell (e.g., a promoter sequence such as a mGluR6 or fragment thereof), and (3) a 3' adeno-associated virus inverted terminal repeat. In addition, the rAAV vector may preferably contain a polyadenylation sequence.

Generally, rAAV vectors have one copy of the AAV ITR at each end of the transgene or gene of interest, in order to allow replication, packaging, and efficient integration into cell chromosomes. The ITR consists of nucleotides 1 to 145 at the 5'-end of the AAV DNA genome, and nucleotides 4681 to 4536 (i.e., the same sequence) at the 3'-end of the AAV DNA genome. The rAAV vector may also include at least 10 nucleotides following the end of the ITR (i.e., a portion of the "D region").

The transgene sequence (e.g., the polynucleotide encoding a light-sensitive protein) can be of about 2- to 5-kb in length (or alternatively, the transgene may additionally contain a "stuffer" or "filler" sequence to bring the total size of the nucleic acid sequence between the two ITRs to between 2 and 5 kb). Alternatively, the transgene may be composed of repeated copies of the same or similar heterologous sequence several times (e.g., two nucleic acid molecules which encode one or more light-sensitive proteins separated by a ribosome readthrough, or alternatively, by an Internal Ribosome Entry Site or "IRES"), or several different heterologous sequences (e.g., ChR2 and NpHR separated by a ribosome readthrough or an IRES; or any two or more of the light-sensitive proteins described herein including, but not limited to, ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof).

Recombinant AAV vectors of the present invention may be generated from a variety of adeno-associated viruses, including for example, any of serotypes 1 through 12, as described herein. For example, ITRs from any AAV serotype are expected to have similar structures and functions with regard to replication, integration, excision and transcriptional mechanisms.

In some embodiments, a cell-type specific promoter (or other regulatory sequence such as an enhancer) is employed to drive expression of a gene of interest, e.g., a light-sensitive protein, ChR2, etc., in one or more specific cell types. In other cases, within certain embodiments of the invention, expression of the light-sensitive transgene may be accomplished by a separate promoter (e.g., a viral, eukaryotic, or other promoter that facilitates expression of an operatively linked sequence in a eukaryotic cell, particularly a mammalian cell). Representative examples of suitable promoters in this regard include a mGluR6 promoter, a GNA01 promoter, a CBA/smCBA (fusion of the CMV immediate early enhancer and bovine beta actin promoter plus intro1-exon1 junction) promoter, CBA promoter (chicken β-actin), CMV promoter, RSV promoter, SV40 promoter, MoMLV promoter, or derivatives, mutants and/or fragments thereof. Promoters and other regulatory sequences are further described herein.

Other promoters that may similarly be utilized within the context of the present invention include cell or tissue specific promoters (e.g., a rod, cone, or ganglia derived promoter), or inducible promoters. Representative examples of suitable inducible promoters include inducible promoters sensitive to an antibiotic, e.g., tetracycline-responsive promoters such as "tet-on" and/or "tet-off" promoters. Inducible promoters may also include promoters sensitive to chemicals other than antibiotics.

The rAAV vector may also contain additional sequences, for example from an adenovirus, which assist in effecting a desired function for the vector. Such sequences include, for example, those that assist in packaging the rAAV vector into virus particles.

Packaging cell lines suitable for producing adeno-associated viral vectors may be accomplished given available techniques (see e.g., U.S. Pat. No. 5,872,005). Methods for constructing and packaging rAA7I vectors are described in, for example, PCT Intl. Pat. Appl. Publ. No. WO 00/54813.

Flanking the rep and cap open reading frames at the 5' and 3' ends are 145-bp inverted terminal repeats (ITRs), the first 125 bp of which are capable of forming Y- or T-shaped duplex structures. The two ITRs are the only cis elements essential for AAV replication, rescue, packaging and integration of the AAV genome. There are two conformations of AAV ITRs called "flip" and "flop." These differences in conformation originated from the replication model of adeno-associated virus, which uses the ITR to initiate and reinitiate the replication (R. O. Snyder et al., *J. Viral.*, 67:6096-6104; 1993; K. I. Berns, *Microbiol. Rev.*, 54:316-329; 1990). The entire rep and cap domains can be excised and replaced with a therapeutic or reporter transgene.

In some embodiments, self-complementary AAV vectors are used. Self-complementary vectors have been developed to circumvent rate-limiting second-strand synthesis in single-stranded AAV vector genomes and to facilitate robust transgene expression at a minimal dose. In specific embodiments, a self-complementary AAV of any serotype or hybrid serotype or mutant serotype, or mutant hybrid serotype increases expression of a light-sensitive protein such as ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 125%, at least 150%, at least 175%, at least 200%, or more than 200%, when compared to a non-self-complementary rAAV of the same serotype.

Adeno-Associated Viral Serotypes:

In one embodiment, the vector comprises a recombinant AAV of a particular serotype, either naturally occurring or engineered.

AAVs have been found in many animal species, including primates, canine, fowl and human.

Viral serotypes are strains of microorganisms having a set of recognizable antigens in common. There are several known serotypes of AAV, and the efficacy of transfection or transduction within the retina may vary as a function of the specific serotype and the nature of the target cells. rAAV, or a specific serotype of rAAV or AAV, may provide tissue-specific or cell-type specific tropism for gene delivery to retinal bipolar cells (e.g., ON or OFF retinal bipolar cells; rod and cone bipolar cells). While rAAV and/or AAV are relatively-safe vectors for delivering a transgene to a target tissue, the efficacy of delivery, and possibly the safety of delivery, may depend on the coat proteins of the AAV. The protein coat, or capsid, determines which cells can take up the viral payload. Different AAV serotypes, i.e., viruses that differ in their protein coats or capsids, may differ in their tissue tropism, and/or their ability to transduce targeted cells. Transgenes can be packaged within AAV particles with many functionally different coat proteins, or capsids. These different capsids are what define the serotype and may contribute (either entirely or in part) to its ability to transduce particular cell types. The entry of the viral vector begins with the interaction of the capsid and the target cell surface proteins. Without wishing to be bound by theory, it is at this point in the transduction pathway that different serotypes may significantly influence the efficiency of transgene delivery.

In certain embodiments, the AAV vector is of a serotype or variant/mutant thereof including, but not limited to: AAV1 (GenBank accession number AY724675), AAV2 (GenBank accession number AF043303), AAV3, AAV4, AAV5 (GenBank accession number M61166), AAV6, AAV7 (GenBank accession number AF513851), AAV8 (GenBank accession number AF513852), AAV9 (GenBank accession number AX753250), AAV10, AAV11 (GenBank accession number AY631966), or AAV12 (GenBank accession number DQ813647), or mutants, hybrids, or fragments thereof. In certain embodiments the AAV vector comprises one or more, two or more, three or more, four or more, or five or more of the following serotypes: AAV1 (GenBank accession number AY724675), AAV2 (GenBank accession number AF043303), AAV3, AAV4, AAV5 (GenBank accession number M61166), AAV6, AAV7 (GenBank accession number AF513851), AAV8 (GenBank accession number AF513852), AAV9 (GenBank accession number AX753250), AAV10, AAV11 (GenBank accession number AY631966), or AAV12 (GenBank accession number DQ813647), or mutants, hybrids, or fragments thereof. In other embodiments, the AAV vector is of a natural serotype or variant/mutant thereof, heretofore yet undiscovered and uncharacterized.

In certain embodiments, the recombinant AAV is of a combinatorial hybrid of 2, 3, 4, 5, 6, 7, 8, 9, 10, 11, 12, 13, 14, 15 or more serotypes or mutants thereof.

In some embodiments, the AAV vector may be used to specifically transduce a specific cell type, e.g., retinal cells or retinal bipolar cells (e.g., ON or OFF retinal bipolar cells; rod and cone bipolar cells). In some cases, a specific serotype, e.g., AAV2, AAV5, AAV7 or AAV8, may be better than other serotypes at transducing a particular cell type [e.g., retinal bipolar cells (e.g., ON or OFF retinal bipolar cells; rod and cone bipolar cells), neurons] or tissue. For example, a specific AAV serotype such as AAV2, AAV5, AAV7 or AAV8 may transduce a specific cell type, e.g., retinal bipolar cells (e.g., ON or OFF retinal bipolar cells; rod and cone bipolar cells), with an increased transduction efficiency of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 125%, at least 150%, at least 175%, at least 200%, or more than 200%, when compared to a different AAV serotype. In some cases, a specific serotype e.g., AAV2, AAV5, AAV7 or AAV8, may permit transduction of at least 2%, 5%, 10%, 20%, 30%, 40%, 50%, 60%, 70%, 80%, or 90% of cells of a particular cell type, e.g., retinal bipolar cells (e.g., ON or OFF retinal bipolar cells; rod and cone bipolar cells), or of cells within a particular tissue, e.g., retinal tissue.

There is a need in the art for AAV serotypes that can effectively transduce retinal bipolar cells (e.g., ON or OFF retinal bipolar cells; rod and cone bipolar cells), particularly when such transduction enables the delivery and expression of a light-sensitive protein, e.g., ChR2. An important therapy to treat eye disorders or diseases (e.g., visual impairment, blindness), may involve using a particular AAV serotype to express light-sensitive proteins such as ChR2 in retinal bipolar cells (e.g., ON or OFF retinal bipolar cells; rod and cone bipolar cells). For example, in a preferred embodiment, AAV5 or AAV7 serotypes are used to target expression of a gene of interest (e.g., a light-sensitive protein, ChR2, etc.) in retinal cells, e.g., retinal bipolar cells (e.g., ON or OFF retinal bipolar cells; rod and cone bipolar cells). In some cases, AAV5 and/or AAV7 may more efficiently transduce retinal cells, e.g., retinal bipolar cells (e.g., ON or OFF retinal bipolar cells; rod and cone bipolar cells), than other AAV serotypes. For example, in some embodiments, the AAV5 and/or AAV7 serotypes, but not AAV1 serotype, are used to transduce retinal bipolar cells (e.g., ON or OFF retinal bipolar cells; rod and cone bipolar cells). In other cases, AAV2 and/or AAV8 serotypes are used to transduce retinal bipolar cells (e.g., ON or OFF retinal bipolar cells; rod and cone bipolar cells). In some cases, a specific serotype, e.g., AAV2, AAV5, AAV7 or AAV8, may be generally applied to a tissue, e.g., retinal tissue, but then preferentially transduces a specific cell-type over another cell type.

In some cases, an AAV, e.g., AAV2, AAV5, AAV7, or AAV8 that is introduced to the retina may preferentially transduce retinal bipolar cells (e.g., ON or OFF retinal bipolar cells; rod and cone bipolar cells) so that the transgene is expressed more highly in retinal bipolar cells compared to other retinal cells. In some cases, the particular serotype e.g., AAV2, AAV5, AAV7 or AAV8, of the AAV may be the cause or contribute to the cause of such preferential transduction. In some cases, only a small subset of the bipolar cells is transduced.

In some embodiments, a specific serotype of AAV, e.g., AAV5 and/or AAV7 (or any other AAV serotype or mutant described herein) comprising a non-cell-type-specific promoter is used to drive expression of a light-sensitive protein in a particular cell type. In some cases, a specific serotype of AAV that has been demonstrated to preferentially transduce a particular cell type is used along with a cell-type specific promoter to drive expression of a protein of interest, e.g., a light-sensitive protein, in a specific cell-type.

The AAV ITR sequences and other AAV sequences employed in generating the minigenes, vectors, and capsids, and other constructs used in certain embodiments may be obtained from a variety of sources. For example, the sequences may be provided by presently-identified human AAV types or by AAV serotypes as-yet-to-be-identified. Similarly, AAVs known to infect other animals may also provide the ITRs employed in the molecules or constructs of this invention. Similarly, the capsids from a variety of serotypes of AAV may be "mixed-and-matched" with the other vector components (see, e.g., PCT Intl. Pat. Appl. Publ. No. WO2001/83692; published Nov. 8, 2001, and incorporated herein by reference). A variety of these viral serotypes and strains are available from the American TypeCulture Collection (Manassas, Va., USA), or are available from a variety of academic or commercial sources. Alternatively, it may be desirable to synthesize sequences used in preparing the vectors and viruses of the invention using known techniques, which may utilize AAV sequences that are published and/or available from a variety of databases.

Adeno-Associated Viruses & Mutations of Surface-Exposed Residues

Recombinant adeno-associated virus (rAAV) vectors are in use in several clinical trials, but relatively large vector doses are needed to achieve therapeutic benefits. Large vector doses may also trigger an immune response as a significant fraction of the vectors may fail to traffic efficiently to the nucleus and may be targeted for degradation by the host cell proteasome machinery. It has been reported that epidermal growth factor receptor protein tyrosine kinase (EGFR-PTK) signaling negatively affects transduction by AAV serotype 2 vectors by impairing nuclear transport of the vectors (Zhong, 2007). Tyrosine-phosphorylated AAV2 vectors enter, but do not transduce effectively, in part because of the ubiquitination of AAV capsids followed by proteasome-mediated degradation. Point mutations in tyrosine residues in AAV2 lead to high-efficiency transduction at lower virus titers (Zhong, 2008).

In one embodiment, tyrosine-mutated AAVs (e.g., AAV2 or AAV8) are used in order to improve the efficiency of transduction of retinal cells, e.g., retinal bipolar cells (FIG. 9A through FIG. 12C). In one embodiment, mutations of the surface-exposed tyrosine residues of the rAAV capsid allow the vectors to evade phosphorylation and subsequent ubiquitination and, thus, prevent proteasome-mediated degradation, leading to greater transduction and subsequent gene expression of light-sensitive proteins.

In a related embodiment, any one or more surface exposed residues other than tyrosine may be mutated to improve the transduction efficiency, tissue/cell-type tropism, expression characteristics, and titers needed for effective infection.

As described herein, modification and changes to the structure of the polynucleotides and polypeptides of wild-type rAAV vectors may result in improved rAAV virions possessing desirable characteristics. For example, mutated rAAV vectors may improve delivery of light-sensitive gene constructs to selected mammalian cell, tissues, and organs for the treatment, prevention, and prophylaxis of various diseases and disorders. Such approach may also provide a means for the amelioration of symptoms of such diseases, and to facilitate the expression of exogenous therapeutic and/or prophylactic polypeptides of interest via rAAV vector-mediated gene therapy. The mutated rAAV vectors may encode one or more proteins, e.g., the light-sensitive proteins, e.g., ChR2, described herein. The creation (or insertion) of one or more mutations into specific polynucleotide sequences that encode one or more of the light-sensitive proteins encoded by the disclosed rAAV constructs are provided herein. In certain circumstances, the resulting light-sensitive polypeptide sequence is altered by these mutations, or in other cases, the sequence of the polypeptide is unchanged by one or more mutations in the encoding polynucleotide to produce modified vectors with improved properties for effecting gene therapy in mammalian systems. As described herein, codon-optimization of the polynucleotide encoding the light-sensitive protein may also improve transduction efficiency.

The ubiquitin-proteasome pathway plays a role in AAV-intracellular trafficking. Substitution of surface exposed tyrosine residues on, for example, AAV2 or AAV8 capsids permits the vectors to either have limited ubiquitination or to escape ubiquitination altogether. The reduction in, or absence of, ubiquitination may help prevent the capsid from undergoing proteasome-mediated degradation. AAV or rAAV capsids can be phosphorylated at tyrosine residues by EGFR-PTK in an in vitro phosphorylation assay, and the phosphorylated AAV capsids retain their structural integrity. Although phosphorylated AAV vectors may enter cells as efficiently as their unphosphorylated counterparts, their transduction efficiency may be significantly impaired.

In some cases, a recombinant adeno-associated viral (rAAV) vector comprises a capsid protein with a mutated tyrosine residue which enables to the vector to have improved transduction efficiency of a target cell, e.g., a retinal bipolar cell (e.g., ON or OFF retinal bipolar cells; rod and cone bipolar cells). In some cases, the rAAV vector further comprises a promoter (e.g., mGluR6, or a fragment thereof) capable of driving the expression of a protein of interest in the target cell.

In some cases, expression in a specific cell type is further achieved by including a cell-type specific promoter described herein within the rAAV vector.

In one embodiment, a recombinant adeno-associated viral (rAAV) vector comprises at least a first capsid protein comprising at least a first phosphorylated tyrosine amino acid residue, and at least a first nucleic acid segment that encodes a light-sensitive protein operably linked to a promoter capable of expressing the segment in a host cell.

In one embodiment, a mutation may be made in any one or more of tyrosine residues of the capsid protein of AAV1 to AAV12, or in one or more hybrid AAVs. In specific embodiments, these are surface-exposed tyrosine residues. In a related embodiment, the tyrosine residues are part of the VP1, VP2, or VP3 capsid protein. In exemplary embodiments, the mutation may be made at one or more of the following amino acid residues of an AAV-VP3 capsid protein: Tyr252, Tyr272, Tyr444, Tyr500, Tyr700, Tyr704, Tyr730; Tyr275, Tyr281, Tyr508, Tyr576, Tyr612, Tyr673 or Tyr720. Exemplary mutations are tyrosine-to-phenylalanine mutations including, but not limited to, Y252F, Y272F, Y444F, Y500F, Y700F, Y704F, Y730F, Y275F, Y281F, Y508F, Y576F, Y612G, Y673F and Y720F. In a specific embodiment, these mutations are made in the AAV2 serotype. In some cases, an AAV2 serotype comprises a Y444F mutation and/or an AAV8 serotype comprises a Y733F mutation, wherein 444 and 733 indicate the location of a point tyrosine mutation of the viral capsid. In further embodiments, such mutated AAV2 and AAV8 serotypes encode a light-sensitive protein, e.g., ChR2, and may also comprise a regulatory sequence (e.g., mGluR6) to drive expression of such light-sensitive protein.

In a related embodiment, 1, 2, 3, 4, 5, 6, or 7 mutations are made to the tyrosine residue on an AAV1, 2, 3, 4, 5, 6, 7, 8, 9, 10, 11, 12, or hybrid serotype. In one exemplary embodiment, 3 tyrosines are mutated to create an AAV serotype with a triple-mutation consisting of: Y444F, Y500F, and Y730F.

The rAAV vectors of the present invention may be comprised within an adeno-associated viral particle or infectious rAAV virion, including for example, virions selected from the group consisting of an AAV serotype 1, an AAV serotype 2, an AAV serotype 3, an AAV serotype 4, an AAV serotype 5 and an AAV serotype 6, an AAV serotype 7, an AAV serotype 8, an AAV serotype 9, an AAV serotype 10, an AAV serotype 11, an AAV serotype 12, or a hybrid AAV serotype.

The rAAV vectors of the present invention may also be comprised within an isolated mammalian host cell, including for example, human, primate, murine, feline, canine, porcine, ovine, bovine, equine, epine, caprine, and lupine host cells. The rAAV vectors may be comprised within an isolated mammalian host cell such as a human endothelial, epithelial, vascular, liver, lung, heart, pancreas, intestinal, kidney, muscle, bone, neural, blood, or brain cell.

In certain embodiments, the transduction efficiency of an AAV comprising a mutated capsid protein (e.g., a mutation of a tyrosine residue described herein) expressing a light-sensitive protein such as ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof is increased by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 125%, at least 150%, at least 175%, at least 200%, or more than 200%, when compared to a wild-type AAV expressing a light-sensitive protein. This disclosure also provides mutated rAAV vectors (e.g., the AAV2 Y444F vector or the AAV8 Y733F vector) capable of transducing at least 2%, 5%, 10%, 20%, 30%, 40%, 50%, 60%, 70%, 80%, or 90% of (ON or OFF retinal bipolar cells; rod and cone bipolar cells) bipolar cells. The improvement in transduction created by the mutated capsid may permit transduction of bipolar cells by intravitreal injection. For example, in some embodiments, a mutated rAAV vector or a rAAV combinatorial serotype hybrid vector or a mutated combinatorial serotype hybrid rAAV vector may be capable of transducing at least 2%, 5%, 10%, 20%, 30%, 40%, 50%, 60%, 70%, 80%, or 90% of retinal bipolar cells (e.g., ON or OFF retinal bipolar cells; rod and cone bipolar cells) is introduced to the retina by intravitreal injection. In a specific embodiment, only a subset of the retinal bipolar cells is transduced. In another specific embodiment, only the highly sensitive bipolar cells are transduced.

In certain embodiments the ubiquitin or proteasome-mediated degradation of an AAV comprising a capsid protein with a mutation expressing a light-sensitive protein, such as ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof, is decreased by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%, when compared to a wild-type AAV expressing a light-sensitive protein.

Other Gene Delivery Vectors:

Any of a variety of other vectors adapted for expression of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof or any light-sensitive protein in a cell of the eye, particularly within a retinal cell, more particularly within a non-photoreceptor cell [e.g., amacrine cells, retinal ganglion cells, retinal bipolar cells, (ON or OFF retinal bipolar cells; rod and cone bipolar cells)], are within the scope of the present invention. Gene delivery vectors can be viral (e.g., derived from or containing sequences of viral DNA or RNA, preferably packaged within a viral particle), or non-viral (e.g., not packaged within a viral particle, including "naked" polynucleotides, nucleic acid associated with a carrier particle such as a liposome or targeting molecule, and the like). Other exemplary gene delivery vectors are described below.

Recombinant Adenoviral Vectors (AD):

In other embodiments, the gene delivery vector is a recombinant adenoviral vector. U.S. Pat. No. 6,245,330 describes recombinant adenoviruses, which may be suitable for use in the invention. Ad vectors do not integrate into the host cell genome, particularly preferred when short-term gene is required, typically about 14 days. Thus, use of Ad vectors can require repeated intraocular injections to treat a retinal disease, which continues over decades in the average patient.

The viral tropism of Ad and AAV in the retina is can be different. The subset of cells that are transduced by the vector is usually a receptor-mediated event. Ad vectors have been shown to primarily transduce retinal Muller cells and Retinal pigment epithelial cells following injection. AAV vectors are very efficient at transferring their genetic payload to retinal photoreceptor and non-photoreceptor cells when injected into the eye.

Retroviral Gene Delivery Vectors:

The gene delivery vectors of the invention can be a retroviral gene delivery vector adapted to express a selected gene (s) or sequence (s) of interest (e.g., ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof). Retroviral gene delivery vectors of the present invention may be readily constructed from a wide variety of retroviruses, including for example, B, C, and D type retroviruses as well as spumaviruses and lentiviruses. For example, in some cases, a retrovirus, e.g., a lentivirus, is pseudotyped with an envelope protein or other viral protein to facilitate entry into target cells. In some cases, a lentivirus is pseudotyped with vesicular-stomatitis virus g protein. (see, e.g., *RNA Tumor Viruses*, Second Edition, Cold Spring Harbor Laboratory Press, Cold Spring Harbor, N.Y., USA; 1985). Such retroviruses may be readily obtained from depositories or collections such as the American TypeCulture Collection ("ATCC"), or isolated from known provided herein, and standard recombinant techniques (e.g., Sambrook et al., *Molecular Cloning: A Laboratory Manual* $2^{nd}$ ed., Cold Spring Harbor Laboratory Press, 1989; Kunkel, *Proc. Natl. Acad. Sci. USA*, 82(2):488-492; 1985).

In addition, within certain embodiments of the invention, portions of the retroviral gene delivery vectors may be derived from different retroviruses. For example, within one embodiment of the invention, retroviral LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

Within one aspect of the present invention, retroviral vector constructs are provided comprising a 5'-LTR, a tRNA binding site, a packaging signal, one or more heterologous sequences, an origin of second strand DNA synthesis and a 3'-LTR, wherein the vector construct lacks gag, pol, or env coding sequences.

Other retroviral gene delivery vectors may likewise be utilized within the context of the present invention, and are well known in the art. Packaging cell lines suitable for use with the above-described retroviral vector constructs can be readily prepared according to methods well known in the art, and utilized to create producer cell lines for the production of recombinant vector particles.

Alphavirus Delivery Vectors:

Gene delivery vectors suitable for use in the invention can also be based upon alphavirus vectors. For example, the Sindbis virus is the prototype member of the alphavirus genus of the togavirus family. The unsegmented genomic RNA (49S RNA) of Sindbis virus is approximately 11,703 nucleotides in length, contains a 5' cap and a 3' polyadenylated tail, and displays positive polarity. Infectious enveloped Sindbis virus is produced by assembly of the viral nucleocapsid proteins onto the viral genomic RNA in the cytoplasm and budding through the cell membrane embedded with viral encoded glycoproteins. Entry of virus into cells is by endocytosis through clatharin-coated pits, fusion of the viral membrane with the endosome, release of the nucleocapsid, and uncoating of the viral genome. During viral replication, the genomic 49S RNA serves as template for synthesis of the complementary negative strand. This negative strand in turn serves as template for genomic RNA and an internally initiated 26S subgenomic RNA.

The Sindbis viral nonstructural proteins are translated from the genomic RNA while structural proteins are translated from the subgenomic 26S RNA. All viral genes are expressed as a polyprotein and processed into individual proteins by post-translational proteolytic cleavage. The packaging sequence resides within the nonstructural coding region, therefore only the genomic 49S RNA is packaged into virions.

Several different Sindbis vector systems may be constructed and utilized within the present invention. Representative examples of such systems include those described within U.S. Pat. Nos. 5,091,309 and 5,217,879, and PCT Intl. Pat. Appl. Publ. No. WO 95/07994.

Other viral gene delivery vectors. In addition to retroviral vectors and alphavirus vectors, numerous other viral vectors systems may also be utilized as a gene delivery vector. Representative examples of such gene delivery vectors include viruses such as pox viruses, such as canary pox virus or vaccinia virus.

Non-Viral Gene Delivery Vectors:

In addition to the above viral-based vectors, numerous non-viral gene delivery vectors may likewise be utilized within the context of the present invention. Representative examples of such gene delivery vectors include direct delivery of nucleic acid expression vectors, naked DNA (e.g., DNA not contained in a viral vector) (PCT Intl. Pat. Appl. Publ. No. WO 90/11092), polycation condensed DNA linked or unlined to killed adenovirus (Curiel et al., *Hum. Gene Ther.*, 3:147-154; 1992), DNA ligand linked to a ligand with or without one of the high affinity pairs described above (Wu et al., *J. Biol. Chem.*, 264:16985-16987; 1989), nucleic acid containing liposomes (e.g., PCT Intl. Pat. Appl. Publ. Nos. WO 95/24929 and WO 95/12387), and certain eukaryotic cells.

Regulatory Sequences:

In some embodiments, regulatory sequences or elements are utilized to allow for cell-type or tissue-type specific targeting of ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof. In related embodiments, regulatory elements are used to specifically target retinal neurons, or retinal bipolar cells (e.g., ON or OFF retinal bipolar cells; rod and cone bipolar cells), or retinal ganglion cells, or photoreceptor cells, or amacrine cells. Examples of regulatory sequences or elements include, but are not limited to promoter, silencer, enhancer, and insulator sequences.

In some embodiments, regulatory sequences such as promoters suitable for use in the present invention include constitutive promoters, strong promoters (e.g., CMV promoters), inducible promoters, and tissue-specific or cell-specific promoters (e.g., promoters that preferentially facilitate expression in a limited number of tissues or cell types (e.g., eye tissues, retina, retinal cells, photoreceptor cells, and the like).

Any of a variety of regulatory sequences can be used in the gene delivery vectors of the invention to provide for a suitable level or pattern of expression of the light-sensitive protein of interest. The regulatory sequences are generally derived from eukaryotic regulatory sequences.

In some embodiments, non-cell specific regulatory elements are used. In one embodiment, the promoter comprises (from 5'-to-3') a viral enhancer (a CMV immediate early enhancer), and a β-actin promoter (a bovine or chicken β-actin promoter-exon 1-intron 1 element). In a specific embodiment, the promoter comprises (from 5'-to-3') CMV immediate early enhancer (381 bp)/bovine or chicken β-actin (CBA) promoter-exon 1-intron 1 (1352 bp) element, which together are termed herein the "CBA promoter" (FIG. 7). In some embodiments a nucleic acid encoding a light-sensitive protein is delivered to a cell using a viral vector such as AAV carrying a selected light-sensitive transgene-encoding DNA regulated by a non-cell-specific promoter and/or other regulatory sequences that expresses the product of the DNA. In some related embodiments, the non-cell-specific promoter is general promoter such as a ubiquitin-based promoter, for e.g., a ubiquitin C promoter.

In other embodiments, a light-sensitive protein is delivered to a cell type or tissue type of interest using a viral vector such as AAV carrying a selected light-sensitive transgene-encoding DNA regulated by a promoter and/or other regulatory sequences that expresses the product of the DNA in selected retinal cells of a subject. In specific embodiments, expression is targeted to particular types of cells within the retina through the use of a specific promoter nucleotide sequence and/or other regulatory regions such as silencer, enhancer, or insulator sequences which are engineered into the vector. In some embodiments, different regulatory sequences are used to drive expression of different engineered genes in different populations of cells.

In other embodiments, retinal bipolar cell-specific regulatory sequences such as promoter, enhancer, silencer, and insulator sequences are used. In specific embodiments, the ON bipolar cells are targeted. In other embodiments, the OFF bipolar cells are targeted. In other embodiments, the rode bipolar cells are targeted. In other embodiments, the cone bipolar cells are targeted.

In one embodiment, specific expression of a light sensitive proteins in ON bipolar cells is targeted using a light-sensitive protein such as ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof operatively linked to a GRM6 (metabotropic glutamate receptor 6, mGluR6) regulatory sequence or a fragment thereof. In one embodiment, the full-length mGluR6 regulatory sequence is utilized.

In another embodiment, specific expression of a light sensitive proteins in ON bipolar cells is targeted using a light-sensitive protein such as ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof operatively linked to a mGluR6 regulatory sequence fragment. In a specific embodiment, the mGluR6 regulatory sequence fragment is the sequence presented in FIG. 6. In a related embodiment, the mGluR6 regulatory sequence fragment is substantially the same as the sequence presented in FIG. 6, or is about 60% identical, or is about 70% identical, or is about 80% identical, or is about 90% identical, or is about 95% identical to the sequence presented in FIG. 6.

Many known promoters are too large to fit into the genome of the AAV. Indeed, the original cell-specific regulatory sequence for mGluR6 (Dhingra, 2008) was far too large (approximately 10.5 Kb) to be used in AAV. In a preferred embodiment of the current invention, a mGluR6 regulatory sequence fragment is used, one that is small enough to be used in AAV-mediated delivery. In related embodiments the mGluR6 regulatory sequence fragment is less than about 2000 base pairs, less than about 1000 base pairs, less than about 750 base pairs, less than about 500 base pairs, less than about 250 base pairs, or less than about 100 base pairs in length. In another related embodiment, the mGluR6 regulatory sequence fragment is a variant of the sequence presented in FIG. 6.

In another embodiment, specific expression of a light sensitive proteins in ON bipolar cells is targeted using a light-sensitive protein such as ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof operatively linked to a GNA01 (guanine nucleotide binding protein (G protein), alpha activating activity polypeptide 0) regulatory sequence. In a related embodiment the regulatory sequence is substantially the same as GNA01 sequence, or is about 60% identical, or is about 70% identical, or is about 80% identical, or is about 90% identical, or is about 95% identical to the GNA01 sequence.

Retinal Bipolar Cells and Targeting

Although only a fraction of the human visual system, the retina is a complex system that filters, amplifies, and modulates the visual signal before it is sent to the rest of the visual system (Wassle, 2004). The vast majority of this processing happens within the inner plexiform layer (IPL) where a system of bipolar and amacrine cells refine the visual signal into its primary components (e.g., motion, contrast, resolution) (Mills, 1999; Roska, 2001). Some groups are currently targeting ChR2 to the ganglion cell layer, which bypasses the processing power of the IPL and system of amacrine cells (Bi, 2006; Greenberg, 2007; Tomita, 2007). These groups have reported very few behavioral changes.

The majority of retinal cells are either ON-center (increased firing rate as a result of a step increase in contrast within the center of the receptive field) or OFF center type (increased firing rate as a result of a step decrease in contrast in the center of the receptive field), working in a push-pull inhibitory fashion (Wassle, 2004). In order to maintain this relationship between the two pathways, these two pathways can be driven independently. ON and OFF channels of information traveling from bipolar to ganglion cells are partially modulated through a network of inhibitory amacrine cells within the inner nuclear layer (Roska, 2001). This bipolar-amacrine network produces temporally-distinct parallel channels of information: sustained-activity neurons, for example, maintain activity throughout the light step, whereas transient-activity neurons have activity only at the onset or offset. These distinct patterns of response code for visual information luminance, shape, edges, and motion (Wassle, 2004). In some embodiments, cells that are pre-synaptic to the retinal ganglion cells are genetically targeted to maintain the naturalism of these pathways and elicit naturalistic ganglion cell spiking.

In some embodiments, retinal bipolar cells (e.g., ON or OFF retinal bipolar cells; rod and cone bipolar cells) are genetically targeted. Targeting retinal bipolar cells may allow the retina to respond to external light and, more importantly, convey meaningful image information to the brain even in the absence of natural photoreceptors.

Conditions Amenable to Treatment

In some embodiments, the present invention provides methods of treating a subject suffering from a disease or disorder. The compositions and methods described herein can be utilized to treat central and peripheral nervous system diseases and disorders.

In one aspect, the compositions and methods of this invention are utilized to treat photoreceptor diseases. Photoreceptor diseases such as retinitis pigmentosa (RP) and age-related macular degeneration (ARMD) cause blindness (Congdon, 2004) in 15 million people worldwide (Chader, 2002), a number that is increasing with the age of the population. There have been attempts to restore basic visual function through gene replacement therapy or cellular transplantation (Acland, 2001, Acland, 2005, Batten, 2005, Pawlyk, 2005, Aguirre, 2007, MacLaren, 2006).

However, current approaches are fundamentally limited in scope and extent of potential impact, as they attempt to correct mechanistically distinct genetic pathways on a one-at-a-time basis (Punzo, 2007). Photoreceptor diseases are genetically diverse, with over 160 different mutations leading to degeneration (Punzo, 2007). There have also been efforts in utilizing electrical stimulation with implanted acute, semi-acute, and long-term retinal prostheses in human subjects (de Balthasar, 2008; Horsager, 2009). They have shown elementary progress, but are gene-nonspecific; electrical stimulation offers only gross specificity and indiscriminately drives visual information channels mediated by unique cell types. Activating retinal neurons requires large disc electrodes (at least 20 times the diameter of a retinal ganglion cell), leading to stimulation of broad areas of retina in a nonselective fashion, greatly limiting the achievable visual resolution (Winter, 2007). In this aspect, the compositions and methods of this invention consist of introducing a gene encoding a light-sensitive protein (e.g., ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof) to induce light sensitivity in $2^{nd}$ order neurons (e.g., bipolar cells) delivered using a viral vector such as an AAV8 with a single tyrosine to phenylalanine mutation, under the control of a regulatory element (e.g., GRM6). The activation of these light-sensitive proteins could be controlled by ambient light or through a light-delivery device such as the goggles described in FIG. 13.

The methods of the invention can be used to treat (e.g., prior to or after the onset of symptoms) in a susceptible subject or subject diagnosed with a variety of eye diseases. The eye disease may be a result of the environment (e.g., chemical insult, thermal insult, and the like), mechanical insult (e.g., injury due to accident or surgery), or genetic factors. The subject having the condition may have one or both eyes affected, and therapy may be administered according to the invention to the affected eye or to an eye at risk of photoreceptor degeneration due to the presence of such a condition in the subject's other, affected eye.

The present invention provides methods which generally comprise the step of intraocularly administering (e.g., by subretinal injection or by intravitreal injection) a gene delivery vector which directs the expression of a light-sensitive protein to the eye to treat, prevent, or inhibit the onset or progression of an eye disease. As utilized herein, it should be understood that the terms "treated, prevented, or, inhibited" refers to the alteration of a disease onset, course, or progress in a statistically significant manner.

Another condition amenable to treatment according to the invention is Age-related Macular Degeneration (AMD). The macula is a structure near the center of the retina that contains the fovea. This specialized portion of the retina is responsible for the high-resolution vision that permits activities such as reading. The loss of central vision in AMD is devastating. Degenerative changes to the macula (maculopathy) can occur at almost any time in life but are much more prevalent with advancing age. Conventional treatments are short-lived, due to recurrent choroidal neovascularization. AMD has two primary pathologic processes, choroidal neovascularization (CNV) and macular photoreceptor cell death.

Exemplary conditions of particular interest which are amenable to treatment according to the methods of the invention include, but are not necessarily limited to, retinitis pigmentosa (RP), diabetic retinopathy, and glaucoma, including open-angle glaucoma (e.g., primary open-angle glaucoma), angle-closure glaucoma, and secondary glaucomas (e.g., pigmentary glaucoma, pseudoexfoliative glaucoma, and glaucomas resulting from trauma and inflammatory diseases).

Further exemplary conditions amenable to treatment according to the invention include, but are not necessarily limited to, retinal detachment, age-related or other maculopathies, photic retinopathies, surgery-induced retinopathies, toxic retinopathies, retinopathy of prematurity, retinopathies due to trauma or penetrating lesions of the eye, inherited retinal degenerations, surgery-induced retinopathies, toxic retinopathies, retinopathies due to trauma or penetrating lesions of the eye.

Specific exemplary inherited conditions of interest for treatment according to the invention include, but are not necessarily limited to, Bardet-Biedl syndrome (autosomal recessive); congenital amaurosis (autosomal recessive); cone or cone-rod dystrophy (autosomal dominant and X-linked forms); congenital stationary night blindness (autosomal dominant, autosomal recessive and X-linked forms); macular degeneration (autosomal dominant and autosomal recessive forms); optic atrophy (autosomal dominant and X-linked forms); retinitis pigmentosa (autosomal dominant, autosomal recessive and X-linked forms); syndromic or systemic retinopathy (autosomal dominant, autosomal recessive and X-linked forms); and Usher syndrome (autosomal recessive).

In another aspect, the compositions and methods of this invention are utilized to treat peripheral injury, nociception, or chronic pain. Nociception (pain) for prolonged periods of time can give rise to chronic pain and may arise from injury or disease to visceral, somatic and neural structures in the body. Although the range of pharmacological treatments for neuropathic pain has improved over the past decade, many patients do not get effective analgesia, and even effective medications often produce undesirable side effects. Substance P (SP) is involved in nociception, transmitting information about tissue damage from peripheral receptors to the central nervous system to be converted to the sensation of pain. It has been theorized that it plays a part in fibromyalgia A role of substance P in nociception is suggested by the reduction in response thresholds to noxious stimuli by central administration of NK1 and NK2 agonists. Pain behaviors induced by mechanical, thermal and chemical stimulation of somatic and visceral tissues were reduced in the mutant mice lacking SP/NKA. In one embodiment, light-sensitive proteins can silence the activity of over-active neurons (i.e., substance P expressing peripheral neurons) due to peripheral injury or chronic pain using NpHR or eNpHR. NpHR/eNpHR can be genetically targeted to substance P expressing cells using the substance P promoter sequence. In another embodiment, light-sensitive proteins enhance the activity of neurons that are inactive due to peripheral injury or chronic pain.

In another aspect, the compositions and methods of this invention are utilized to treat spinal cord injury and/or motor neuron diseases. Spinal cord injury can cause myelopathy or damage to white matter and myelinated fiber tracts that carry sensation and motor signals to and from the brain. It can also damage gray matter in the central part of the spine, causing segmental losses of interneurons and motor neurons. Spinal cord injury can occur from many causes, including but not limited to trauma, tumors, ischemia, abnormal development, neurodevelopmental, neurodegenerative disorders or vascular malformations. In one embodiment, light-sensitive proteins activate damaged neural circuits to restore motor or sensory function. In one specific embodiment, the elements act to allow control of autonomic and visceral functions. In other embodiments, the elements act to allow control of somatic skeletal function. The neural control of storage and voiding of urine is complex and dysfunction can be difficult to treat. One treatment for people with refractory symptoms is continuous electrical nerve stimulation of the sacral nerve roots using implanted electrodes and an implanted pulse generator. However, stimulation of this nerve root can result in a number of different complications or side effects. Being able to directly control the sacral nerve through genetically-targeted tools would be highly beneficial. In one embodiment, both ChR2 and NpHR could be expressed in this nerve to control storage and voiding of the bladder.

In another aspect, the compositions and methods of this invention are utilized to treat Parkinson's disease. Parkinson's disease belongs to a group of conditions called movement disorders. They are characterized by muscle rigidity, tremor, a slowing of physical movement (bradykinesia) and, in extreme cases, a loss of physical movement (akinesia). The primary symptoms are the results of decreased stimulation of the motor cortex by the basal ganglia, normally caused by the insufficient formation and action of dopamine, which is produced in the dopaminergic neurons of the brain. Parkinson's disease is both chronic and progressive. Deep brain stimulation (DBS) is an effective surgical treatment for advanced Parkinson's disease (PD), with significant advantages in morbidity-mortality and quality of life when compared to lesion techniques such as thalamotomy and/or pallidotomy. The procedure is indicated in patients with severe resting tremor, unresponsive to conventional medical treatment or with motor complications. The most commonly reported complications in the intra- and post-surgical period are aborted procedure, misplaced leads, intracranial hemorrhage, seizures and hardware complications, whereas in the long-term period, symptoms may include high level cognitive dysfunction, psychiatric, and subtle language problems. Indeed, this method of therapy would be improved by being able to target specific cell types within a given region to avoid these side effects. In one embodiment, light-sensitive proteins specifically activate dopaminergic circuits.

In another specific aspect, the compositions and methods of this invention are utilized to treat epilepsy and seizures. Epilepsy is a neurological disorder that is often characterized by seizures. These seizures are transient signs and/or symptoms due to abnormal, excessive or asynchronous neuronal activity in the brain. Over 30% of people with epilepsy do not have seizure control even with the best available medications. Epilepsy is not a single disorder, but rather as a group of syndromes with vastly divergent symptoms but all involving episodic abnormal electrical activity in the brain. Acute deep brain stimulation (DBS) in various thalamic nuclei and medial temporal lobe structures has recently been shown to be efficacious in small pilot studies. There is little evidence-based information on rational targets and stimulation parameters. Amygdalohippocampal DBS has yielded a significant decrease of seizure counts and interictal EEG abnormalities during long-term follow-up. Data from pilot studies suggest that chronic DBS for epilepsy may be a feasible, effective, and safe procedure. Again, being able to genetically-target activation to specific subsets of cells would improve the quality of the therapy as well as minimize overall side effects. In specific embodiments, the light-sensitive proteins are utilized to alter the asynchronous electrical activity leading to seizures in these deep brain areas.

In another aspect, the compositions and methods of this invention are utilized to effect the light-stimulated release of implanted drug or vaccine stores for the prevention, treatment, and amelioration of diseases.

In another aspect, the compositions and methods of this invention are utilized to treat neurodegenerative disease selected from but not limited to alcoholism, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), chronic pain, Canavan disease, Cockayne syndrome, corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), multiple sclerosis, multiple system atrophy, narcolepsy, neuroborreliosis, Parkinson's disease, Pelizaeus-Merzbacher Disease, Pick's disease, primary lateral sclerosis, prion diseases, Refsum's disease, Sandhoffs disease, Schilder's disease, subacute combined degeneration of spinal cord secondary to pernicious anemia, schizophrenia, Spielmeyer-Vogt-Sjogren-Batten disease (also known as Batten disease), spinocerebellar ataxia (multiple types with varying characteristics), spinal muscular atrophy, Steele-Richardson-Olszewski disease, and Tables dorsalis.

In another aspect the compositions and methods of this invention are utilized to treat a neurodevelopmental disease selected from but not limited to attention deficit hyperactivity disorder (ADHD), attention deficit disorder (ADD), schizophrenia, obsessive-compulsive disorder (OCD), mental retardation, autistic spectrum disorders (ASD), cerebral palsy, Fragile-X Syndrome, Downs Syndrome, Rett's Syndrome, Asperger's syndrome, Williams-Beuren Syndrome, childhood disintegrative disorder, articulation disorder, learning disabilities (i.e., reading or arithmetic), dyslexia, expressive language disorder and mixed receptive-expressive language disorder, verbal or performance aptitude. Diseases that can result from aberrant neurodevelopmental processes can also include, but are not limited to bi-polar disorders, anorexia, general depression, seizures, obsessive compulsive disorder (OCD), anxiety, bruixism, Angleman's syndrome, aggression, explosive outburst, self-injury, post-traumatic stress, conduct disorders, Tourette's disorder, stereotypic movement disorder, mood disorder, sleep apnea, restless legs syndrome, dysomnias, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder, reactive attachment disorder; separation anxiety disorder; oppositional defiant disorder; dyspareunia, pyromania, kleptomania, trichotillomania, gambling, pica, neurotic disorders, alcohol-related disorders, amphetamine-related disorders, cocaine-related disorders, marijuana abuse, opioid-related disorders, phencyclidine abuse, tobacco use disorder, bulimia nervosa, delusional disorder, sexual disorders, phobias, somatization disorder, enuresis, encopresis, disorder of written expression, expressive language disorder, mental retardation, mathematics disorder, transient tic disorder, stuttering, selective mutism, Crohn's disease, ulcerative colitis, bacterial overgrowth syndrome, carbohydrate intolerance, celiac sprue, infection and infestation, intestinal lymphangiectasia, short bowel syndrome, tropical sprue, Whipple's disease, Alzheimer's disease, Parkinson's Disease, ALS, spinal muscular atrophies, and Huntington's Disease. Further examples, discussion, and information on neurodevelopmental disorders can be found, for example, through the Neurodevelopmental Disorders Branch of the National Institute of Mental Health. Additional information on neurodevelopmental disorders can also be found, for example, in Developmental Disabilities in Infancy and Childhood: Neurodevelopmental Diagnosis and Treatment, Capute and Accardo, eds. 1996, Paul H Brookes Pub Co.; Hagerman, *Neurodevelopmental Disorders: Diagnosis and Treatment*, 1999, Oxford Univ Press; *Handbook of Neurodevelopmental and Genetic Disorders in Children*, Goldstein and Reynolds, eds., 1999, Guilford Press; *Handbook of Neurodevelopmental and Genetic Disorders in Adults*, Reynolds and Goldstein, eds., 2005, Guilford Press; and *Neurodevelopmental Disorders*, Tager-Flusberg, ed., 1999, MIT Press.

Assessment of Therapy

The effects of therapy according to the invention as described herein can be assessed in a variety of ways, using methods known in the art. For example, the subject's vision can be tested according to conventional methods. Such conventional methods include, but are not necessarily limited to, electroretinogram (ERG), focal ERG, tests for visual fields, tests for visual acuity, ocular coherence tomography (OCT), Fundus photography, Visual Evoked Potentials (VEP) and Pupillometry. In other embodiments, the subject can be assessed behaviorally. In general, the invention provides for maintenance of a subject's vision (e.g., prevention or inhibition of vision loss of further vision loss due to photoreceptor degeneration), slows onset or progression of vision loss, or in some embodiments, provides for improved vision relative to the subject's vision prior to therapy.

Methods of Administration

The gene delivery vectors of the present invention can be delivered to the eye through a variety of routes. They may be delivered intraocularly, by topical application to the eye or by intraocular injection into, for example the vitreous (intravitreal injection) or subretinal (subretinal injection) inter-photoreceptor space. Alternatively, they may be delivered locally by insertion or injection into the tissue surrounding the eye. They may be delivered systemically through an oral route or by subcutaneous, intravenous or intramuscular injection. Alternatively, they may be delivered by means of a catheter or by means of an implant, wherein such an implant is made of a porous, non-porous or gelatinous material, including membranes such as silastic membranes or fibers, biodegradable polymers, or proteinaceous material. The gene delivery vector can be administered prior to the onset of the condition, to prevent its occurrence, for example, during surgery on the eye, or immediately after the onset of the pathological condition or during the occurrence of an acute or protracted condition.

In another embodiment the inner limiting membrane (ILM) is broken down to effect delivery. The ILM is the boundary between the retina and the vitreous body, formed by astrocytes and the end feet of Muller cells. In both nonhuman primates and humans, the ILM is thick and provides a substantial barrier to the retina. Indeed, using intravitreal injections, most viral particles are incapable of transducing retinal cells. In one embodiment, to improve transduction efficiency, an ILM peel is conducted comprising carrying out a surgical procedure that comprises peeling off a small part of the ILM. In another embodiment, to improve transduction efficiency, the ILM barrier can be partially, or wholly, broken down comprising using enzymatic techniques and one or more enzymes.

In one embodiment the ILM is maintained to limit the therapeutic effect of the light-sensitive protein to the macula. In another embodiment the ILM peel procedure and/or the ILM enzymatic digestion procedure, both described herein is used to achieve a broader distribution of the light-sensitive protein.

The gene delivery vector can be modified to enhance penetration of the blood-retinal barrier. Such modifications may include increasing the lipophilicity of the pharmaceutical formulation in which the gene delivery vector is provided.

The gene delivery vector can be delivered alone or in combination, and may be delivered along with a pharmaceutically acceptable vehicle. Ideally, such a vehicle would enhance the stability and/or delivery properties. The invention also provides for pharmaceutical compositions containing the active factor, or fragment, or derivative thereof, which can be administered using a suitable vehicle such as liposomes, microparticles or microcapsules. In various embodiments of the invention, it may be useful to use such compositions to achieve sustained release of the active component.

The amount of gene delivery vector (e.g., the number of viral particles), and the amount of light-sensitive protein expressed, effective in the treatment of a particular disorder or condition may depend of the nature of the disorder or condition and a variety of patient-specific factors, and can be determined by standard clinical techniques.

In one embodiment, the gene delivery vectors are administered to the eye, intraocularly to a variety of locations within the eye depending on the type of disease to be treated, prevented, or, inhibited, and the extent of disease. Examples of suitable locations include the retina (e.g., for retinal diseases), the vitreous, or other locations in or adjacent the retina or in or adjacent the eye.

The human retina is organized in a fairly exact mosaic. In the fovea, the mosaic is a hexagonal packing of cones.

Outside the fovea, the rods break up the close hexagonal packing of the cones but still allow an organized architecture with cones rather evenly spaced surrounded by rings of rods. Thus in terms of densities of the different photoreceptor populations in the human retina, it is clear that the cone density is highest in the foveal pit and falls rapidly outside the fovea to a fairly even density into the peripheral retina (see Osterberg, G., "Topography of the layer of rods and cones in the human retina," Acta Ophthal., (suppl.) 6:1-103, 1935; Curcio, C. A., Sloan, K. R., Packer, O., Hendrickson, A. E. and Kalina, R. E., "Distribution of cones in human and monkey retina: individual variability and radial asymmetry," Science, 236:579-582; 1987).

Access to desired portions of the retina, or to other parts of the eye may be readily accomplished by one of skill in the art (see, generally Medical and Surgical Retina: Advances, Controversies, and Management, Hilel Lewis, Stephen J. Ryan, Eds., medical-"illustrator, Timothy C. Hengst, St. Louis, Mosby, 1994. xix, 534; see also Retina, Stephen J. Ryan, editor in chief, 2nd ed., St. Louis, Mo.: Mosby, 1994. 3 v. (xxix, 2559).

In one embodiment, the amount of the specific viral vector applied to the retina is uniformly quite small as the eye is a relatively contained structure and the agent is injected directly into it. The amount of vector that needs to be injected is determined by the intraocular location of the chosen cells targeted for treatment. The cell type to be transduced may be determined by the particular disease entity that is to be treated.

For example, a single 20-microliter volume (e.g., containing about $10^{13}$ physical particle titer/mL rAAV) may be used in a subretinal injection to treat the macula and fovea of a human eye. A larger injection of 50 to 100 microliters may be used to deliver the rAAV to a substantial fraction of the retinal area, perhaps to the entire retina depending upon the extent of lateral spread of the particles.

A 100-microliter injection may provide several million active rAAV particles into the subretinal space. This calculation is based upon a titer of $10^{13}$ physical particles per milliliter. Of this titer, it is estimated that $\frac{1}{1000}$ to $\frac{1}{10,000}$ of the AAV particles are infectious. The retinal anatomy constrains the injection volume possible in the subretinal space (SRS). Assuming an injection maximum of 100 microliters, this could provide an infectious titer of $10^5$ to $10^9$ rAAV in the SRS. This would have the potential of infecting all of the approximately $150 \times 10^6$ photoreceptors in the entire human retina with a single injection.

Smaller injection volumes focally applied to the fovea or macula may adequately transfect the entire region affected by the disease in the case of macular degeneration or other regional retinopathies.

Depending on the application at least $10^3$, $10^4$, $10^5$, $10^6$, $10^7$, $10^8$, $10^9$, $10^{10}$, $10^{11}$, $10^{12}$, $10^{13}$, $10^{14}$, or more particles can be delivered into the tissue of interest.

Gene delivery vectors can alternately be delivered to the eye by intraocular injection into the vitreous, e.g., to treat glaucomatous loss of retinal ganglion cells through apoptosis. In the treatment of glaucoma, the primary target cells to be transduced are the retinal ganglion cells, the retinal cells primarily affected. In such an embodiment, the injection volume of the gene delivery vector could be substantially larger, as the volume is not constrained by the anatomy of the subretinal space. Acceptable dosages in this instance can range from about 25 microliters to 1000 microliters.

Pharmaceutical Compositions:

Gene delivery vectors can be prepared as a pharmaceutically acceptable composition suitable for administration. In general, such pharmaceutical compositions comprise an amount of a gene delivery vector suitable for delivery of light-sensitive protein-encoding polynucleotide to a cell of the eye for expression of a therapeutically effective amount of the light-sensitive protein, combined with a pharmaceutically acceptable carrier or excipient. Preferably, the pharmaceutically acceptable carrier is suitable for intraocular administration. Exemplary pharmaceutically acceptable carriers include, but are not necessarily limited to, saline or a buffered saline solution (e.g., phosphate-buffered saline).

Various pharmaceutically acceptable excipients are well known in the art. As used herein, "pharmaceutically-acceptable excipient" includes any material, which, when combined with an active ingredient of a composition, allows the ingredient to retain biological activity, preferably without causing disruptive reactions with the subject's immune system or adversely affecting the tissues surrounding the site of administration (e.g., within the eye).

Exemplary pharmaceutically carriers include sterile aqueous of non-aqueous solutions, suspensions, and emulsions. Examples include, but are not limited to, any of the standard pharmaceutical excipients such as a saline, buffered saline (e.g., phosphate buffered saline), water, emulsions such as oil/water emulsion, and various types of wetting agents.

Examples of non-aqueous solvents are propylene glycol, polyethylene glycol, hyaluronic acid, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles can include fluid and nutrient replenishers, electrolyte replenishers (such as those based on Ringer's dextrose), and the like.

A composition of gene delivery vector of the invention may also be lyophilized using means well known in the art, for subsequent reconstitution and use according to the invention. Where the vector is to be delivered without being encapsulated in a viral particle (e.g., as "naked" polynucleotide), formulations for liposomal delivery, and formulations comprising microencapsulated polynucleotides, may also be of interest.

Compositions comprising excipients are formulated by well-known conventional methods (see, for example, *Remington's Pharmaceutical Sciences*, Chapter 43, 14$^{th}$ Ed., Mack Publishing Co., Easton, Pa., USA).

In general, the pharmaceutical compositions can be prepared in various forms, preferably a form compatible with intraocular administration. Stabilizing agents, wetting and emulsifying agents, salts for varying the osmotic pressure or buffers for securing an adequate pH value may also optionally be present in the pharmaceutical composition.

The amount of gene delivery vector in the pharmaceutical formulations can vary widely, i.e., from less than about 0.1%, usually at or at least about 2% to as much as 20% to 50% or more by weight, and may be selected primarily by fluid volumes, viscosities, etc., in accordance with the particular mode of administration selected.

The pharmaceutical composition can comprise other agents suitable for administration, which agents may have similar to additional pharmacological activities to the light-sensitive protein to be delivered (e.g., ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof).

Kits:

The invention also provides kits comprising various materials for carrying out the methods of the invention. In one embodiment, the kit comprises a vector encoding a light-sensitive protein polypeptide (e.g., ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof), which vector is adapted for delivery to a subject, particularly an eye of the subject, and adapted to provide for expression of the light-sensitive polypeptide in a cell of an eye, particularly a mammalian cell. The kit can comprise the vector in a sterile vial, which may be labeled for use. The vector can be provided in a pharmaceutical composition. In one embodiment, the vector is packaged in a virus. The kit can further comprise a needle and/or syringe suitable for use with the vial or, alternatively, containing the vector, which needle and/or syringe are preferably sterile. In another embodiment, the kit comprises a catheter suitable for delivery of a vector to the eye, which catheter may be optionally attached to a syringe for delivery of the vector. The kits can further comprise instructions for use, e.g., instructions regarding route of administration, dose, dosage regimen, site of administration, and the like.

Figure 12B:
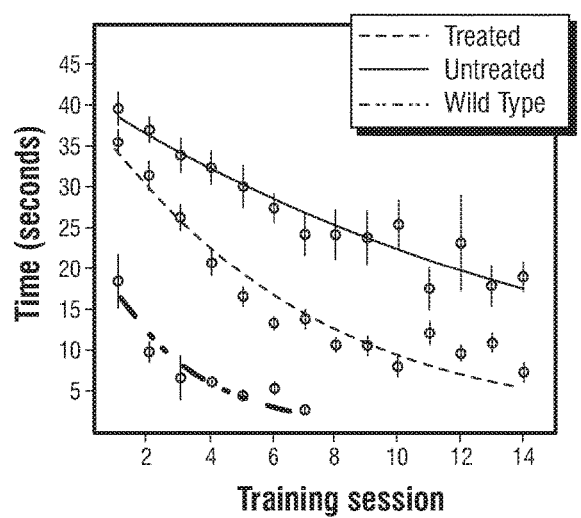
Figure 12C:
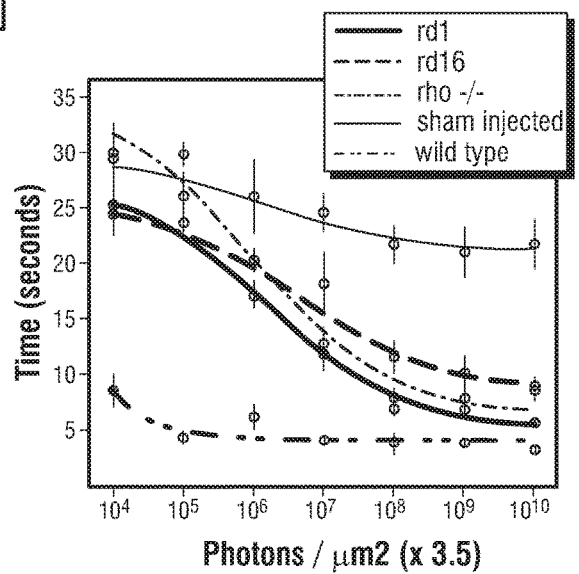

Devices:

The data in FIG. 12C demonstrate that the delivery of light-sensitive proteins can work in the range of normal vision. In some embodiments, for greater efficacy, an internal or external device may be used. In one embodiment, an external device, such as a goggle, can be used for generation and/or amplification of light. In embodiments where a subject having partial vision is being treated, i.e. a treatment of a subject whose photoreceptors are only partially damaged and a light-sensitive protein such as ChR1, ChR2, VChR1, ChR2 C128A, ChR2 C128S, ChR2 C128T, ChR1-ChR2 hybrids/chimeras, ChD, ChEF, ChF, ChIEF, NpHR, eNpHR, melanopsin, and variants thereof is being delivered, the stimulation may be adjusted so that the surviving and/or healthy photoreceptors are not overdriven by the light generation/amplification device. In various embodiments, limiting overdriving by the light generation/amplification device can be achieved by i) stimulating evenly, but shielding the surviving or healthy photoreceptor cells from bright light through an implanted or external contact-lens type partial sunglass (tinting over photoreceptors, clear over light-sensitive protein transduction area); ii) adjustment of the stimulation intensity to match the cell types being stimulated; or iii) adjustment of the stimulation to the be near the top of the visual dynamic range.

In one embodiment, an internal light-generating device is implanted.

In another embodiment, a protective optic, or a contact lens-type barrier is implanted either in conjunction with or independent of the device. In a specific embodiment, such an optic or contact lens protects photoreceptors from light stimulation. In a specific embodiment, the lens comprises tinting over photoreceptors, and clear over light-sensitive protein transduction area.

Figure 13:
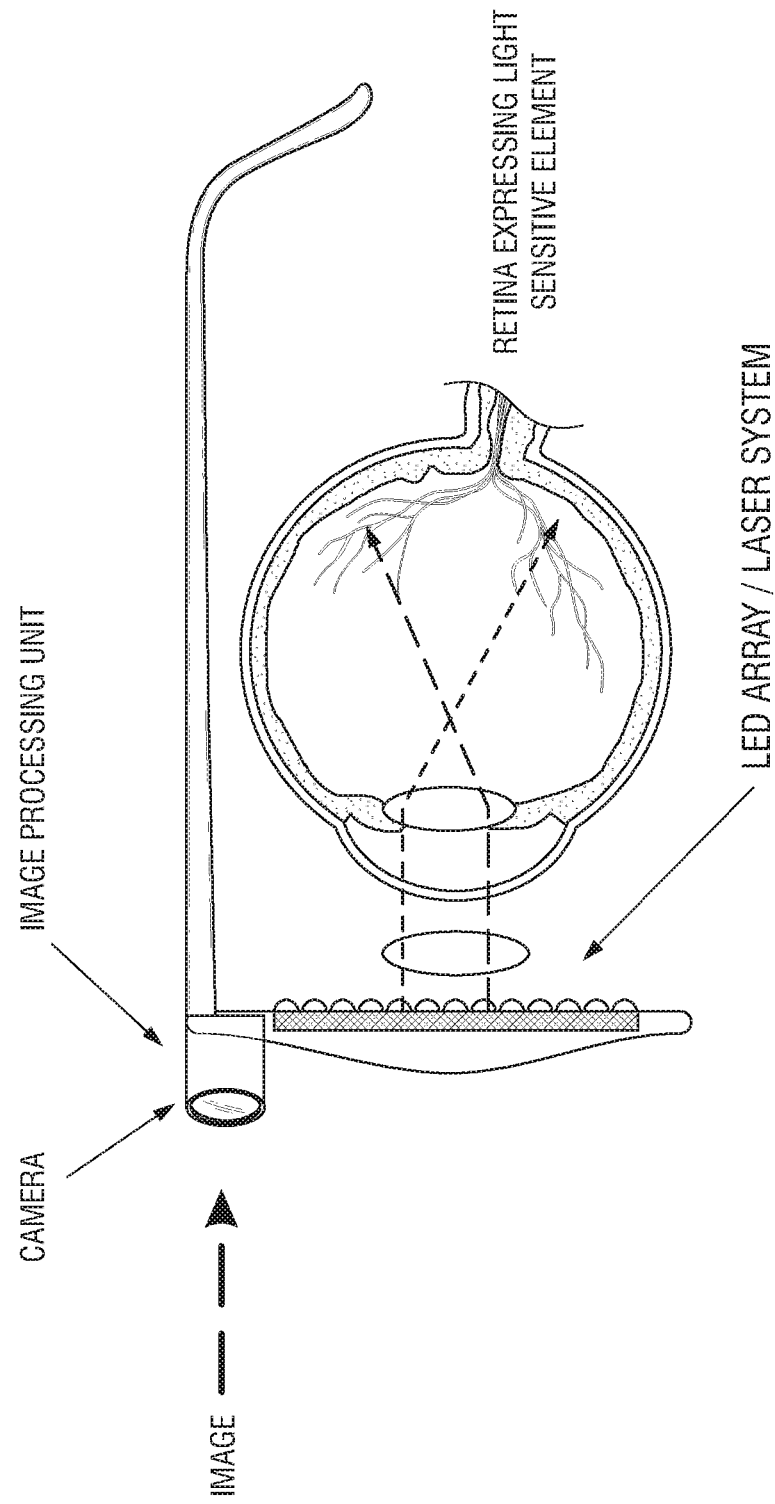
FIG. 13 depicts a goggle-like device with an associated light generation/production element (LED array/laser system) that can trigger expression of light-sensitive proteins.

In some embodiments, a head-mounted, external device or eyewear is utilized. In certain embodiments where the light-sensitive element is not triggered to the extent desired by natural or ambient light, an additional light production or generation source such as a LED array/laser system is provided. In certain embodiments, the external eyewear can additionally include a camera and an image processing unit for the filtering, enhancement, processing, and resolution of the presented images. FIG. 13 depicts a goggle-like device with an associated light production element (LED array/laser system) that may trigger expression of light-sensitive proteins.

In one embodiment, an exemplary camera system would comprise at least three main components: 1) A small camera built into the glasses, 2) an imaging processing unit, and 3) a light delivery system that includes either or both LEDs or a laser system. The camera could either be a single lens camera or a dual camera system that could potentially provide binocular imaging and depth information. The camera could capture either visual light or infrared light. The camera could either be adaptive to various lighting conditions or could be fixed. The image processing unit (IPU) could provide any number of signal transformations including amplification, increased or decreased contrast, structure from motion, edge enhancement, or temporal filtering (i.e., integration). Additionally, saliency algorithms could be employed such that only certain objects within the field of view are enhanced (e.g., moving cars, doorways) and less important objects (e.g., clouds), are filtered out. The LED and/or laser lighting array system could contain a high-density LED array or a scanning laser system that consists of either one (1) or more lasers. The position of the lights could be either fixed or could move. For example, the orientation of the lights relative to the eye could move as a function of eye movements, using an eye movement tracking device as an input. This is depicted in FIG. 13.

In another related exemplary embodiment, an image intensifying device, such as those provided by Telesensory, may be combined with a retinal scanning device (RSD) as developed by Microvision, to provide a head-worn apparatus capable of delivering a bright, intensified image directly to the retina of a patient with impaired vision. Briefly, a RSD projects images onto the retina such that an individual can view a large, full-motion image without the need for additional screens or monitors. Thus, by projecting an intensified image directly onto the retina of an individual with impaired vision, it may be possible to improve vision in those considered to be blind or near-blind.

While some embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure, appreciate that many changes can be made in the specific embodiments that are disclosed, and still obtain a like or similar result without departing from the spirit and scope of the invention.

Example 1: Injection Methods

All procedures in animals were handled according to the statement for the use of animals in Ophthalmic and Vision Research of the Association of Research in Vision and Ophthalmology and the guidelines of the Institutional Animal Care and Use Committee at the University of Florida.

For intrvitreal injections, mice were anesthetized with ketamine (72 mg/kg)/xylazine (4 mg/kg) by intraperitoneal injection. Following anesthetization, a Hamilton syringe fitted with a 33-gauge beveled needle was used. The needle was passed through the sclera, at the equator, next to the limbus, into the vitreous cavity. Injection occurred with direct observation of the needle in the center of the vitreous cavity. The total volume delivered was 1.5 containing different concentrations of the AAV vectors tested.

For subretinal injections, one hour before the anesthesia, eyes of mice were dilated with eye drops of 1% atropine, followed by topical administration of 2.5% phenylephrine. Mice were then anesthetized with ketamine (72 mg/kg)/xylazine (4 mg/kg) by intraperitoneal injection An aperture within the pupil was made through the cornea with a 301/2-gauge disposable needle and a 33-gauge unbeveled blunt needle in a Hamilton syringe was introduced through the corneal opening into the subretinal space and 1.5 µL of AAV was delivered.

Typical titers of the AAV vectors were between $1.3 \times 10^{12}$ and $3.0 \times 10^{13}$.

Example 2: Screening for AAV Serotypes 1, 2, 5, 7, 8, and 9 for Transduction of Retinal Bipolar Cells Screening of known and characterized viral vectors for optimal transduction of retina bipolar cells was carried out. AAV serotypes 1, 2, 5, 7, 8 and 9 carrying green fluorescent protein (GFP) were individually subretinally injected in 4-week old rd1 mice. Rd1 homozygous mice carry a rd1 mutation and rod photoreceptor degeneration in these mice begins around postnatal day (P)10 and is almost completed by P21. GFP was placed under control of the strong, non-cell type specific promoter CBA (fusion of the CMV immediate early enhancer and the bovine β-actin promoter plus intronl-exon1 junction). 1 month later, mice were tested for expression of GFP. Double labeling with the PKCα antibody of mice injected with AAV7 demonstrated that the transduced cells were most likely residual (no outer segment) photoreceptors rather than bipolar cells. Subretinal injections with AAV7 were then performed in 8-week old mice, where there is less of a chance of residual photoreceptors. It was found that AAV7 was highly effective at transducing retinal bipolar cells, leading to GFP expression in at least 75% of all bipolar cells after a single injection (depicted in FIG. 9A through FIG. 9H). These images were obtained 16 weeks after injection, which additionally show that GFP expression using an AAV7 delivery mechanism is stable for at least 4 months. AA7 is a serotype that can be utilized to transduce bipolar cells in an effective and stable manner.

Example 3: Transduction of Retinal Bipolar Cells with Serotypes AAV5, AAV2 Y444F Mutant, and AAV8 Y733F Mutant As depicted in FIG. 10A-FIG. 10E, mice were subretinally (right eye) and intravitreally (left eye) injected with 1.5 µL of adeno-associated viruses (AAV) of different serotypes. The serotypes tested included AAV2, AAV5, and AAV8, all of which are traditional wild type serotypes. Additionally, single tyrosine to phenylalanine mutated serotypes AAV2 Y444F mutant and AAV8 Y733F mutant, where 444 and 733 indicate the location of the point tyrosine mutation of the viral capsid, respectively. The virus contained the self-complementary DNA construct GRM6-ChR2-GFP, where GRM6 is the metabotropic glutamate receptor 6 regulatory sequence driving cell-specific expression in the ON bipolar cells (including rod bipolar), ChR2 is the therapeutic, light-sensitive protein gene, and GFP is the reporter gene.

The images depicted in FIG. 10A through FIG. 10E show the overall expression of GFP (the reporter gene). This expression is shown as white in the black and white images. This is indicative of the overall expression of ChR2 as the ChR2-GFP complex is a fused protein. Note the ringlets of GFP expression in the INL, showing expression of the ChR2-GFP protein complex is membrane bound. These data show that delivery of the construct with an adeno-associated virus leads to robust expression of ChR2-GFP in all 3 mouse models of blindness (rd1, rd16, and rho-/-). This is conducted with 3 different serotypes using a subretinal injection (column 1). When using a tyrosine to phenylalanine mutant serotype, it is possible to get good expression in bipolar cells (INL) using either a subretinal or intravitreal injection. However, wild type serotypes require a subretinal injection to get reasonable transduction of bipolar cells; intravitreal injections using wild type serotypes do not effectively transduce bipolar cells (column 2).

Example 4: Creation of AAV7-GRM6-ChR2 to Establish Light Sensitivity in Retinal ON-Bipolar Cells mGluR6 is a G-protein coupled metabotropic glutamate receptor that is, in the retina, specifically expressed in ON bipolar cells (Tian, 2006). The adeno-associated virus, serotype 7 (AAV7), an mGluR6 regulatory sequence fragment gene sequence (presented in FIG. 6), GRM6, and channel-rhodopsin-2, ChR2 was constructed to form the AAV7-GRM6-ChR2 construct. The cDNA encoding ChR2 with eGFP was cloned downstream (i.e., 3') of the mGluR6 regulatory sequence fragment-SV40 minimal promoter. No IRES was used; ChR2 and GFP were fused. This viral vector construct once delivered using a viral delivery mechanism, and expressed, can establish photosensitivity in retinal ON bipolar cells with high-spatial and temporal resolution. This method can restore retinal responsiveness to optical information, using the ChR2 class of light-activated molecules to directly sensitize spared retinal neurons to light.

Figure 8B:
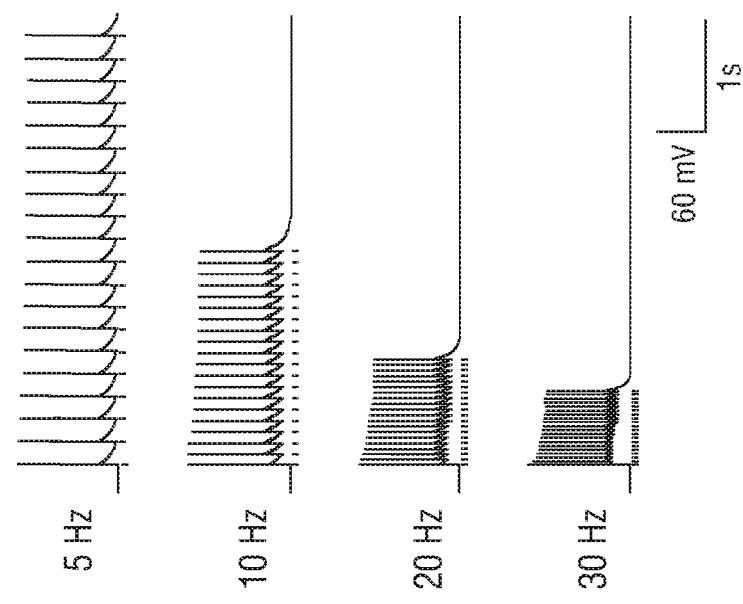
FIG. 8A and FIG. 8B depict neurons expressing ChR2 and firing.
Figure 8A:
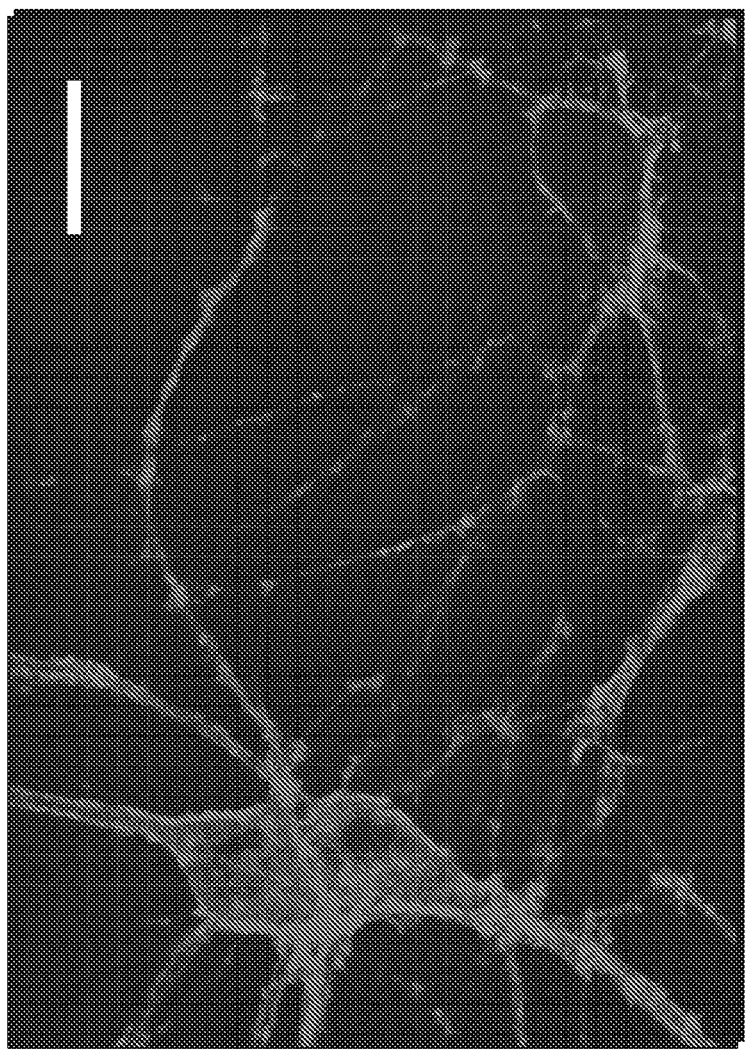
Figure 10A:
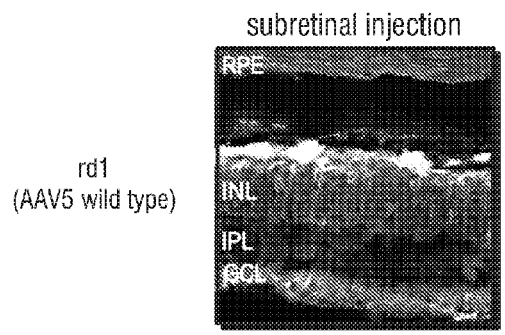
FIG. 10A, FIG. 10B, FIG. 10C, FIG. 10D, and FIG. 10E depict expression of the ChR2-GFP fused protein in rd1, rho−/−, and rd16 in retinal bipolar cells. In each image, the retinal pigment epithelium (RPE), bipolar cells or inner nuclear layer (INL), inner plexiform layer (IPL), and ganglion cell layer (GCL) are noted. The brighter white areas show GFP expression. There are ringlets of expression in the bipolar cells of the INL (except for the AAV5 intravitreal injection)
Figure 10B:
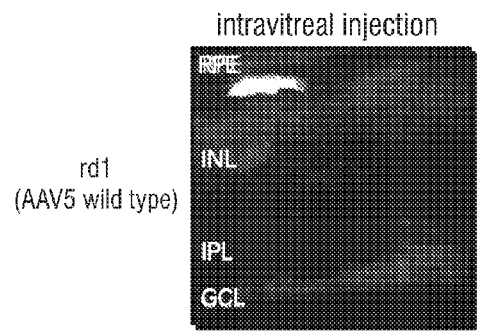
Figure 10C:
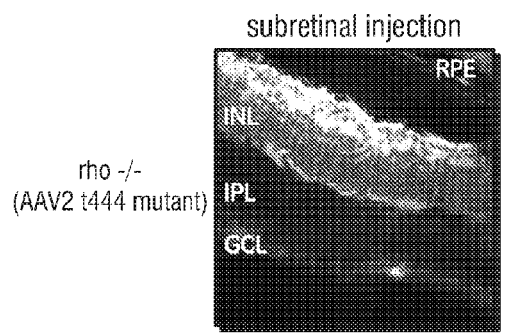
Figure 10D:
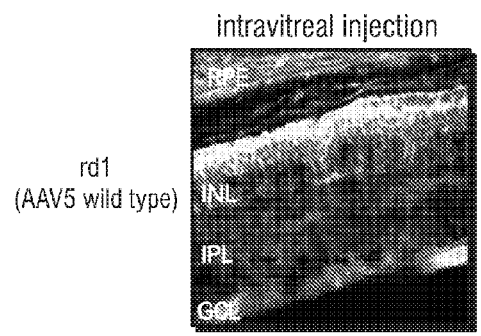
Figure 10E:
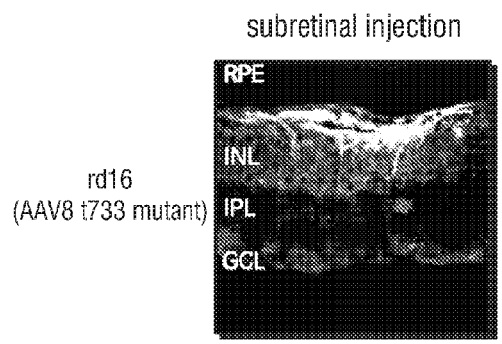
Figure 11A:
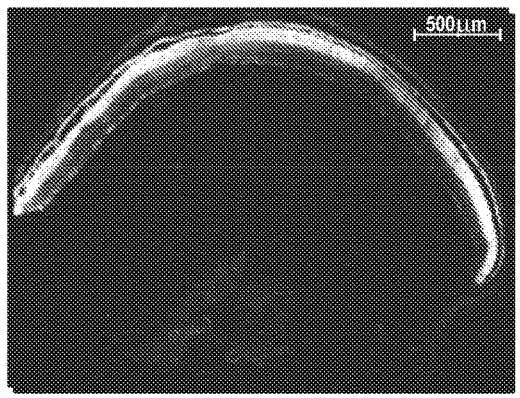
FIG. 11A, FIG. 11B, FIG. 11C, FIG. 11D, FIG. 11E, and FIG. 11F depict analysis of EGFP expression in frozen retinal sections by immunohistochemistry at 1 month, following subretinal injections with the Tyrosine-mutant AAV vectors. Example sections depicting spread and intensity of EGFP fluorescence throughout the retina after transduction with serotype 2 Y444 (FIG. 11A) or serotype 8 Y733 (FIG. 11B). The images are oriented with the vitreous toward the bottom and the photoreceptor layer toward the top. EGFP fluorescence in photoreceptors, RPE and ganglion cells from mouse eyes injected subretinally with serotype 2 Y444 (FIG. 11C) EGFP fluorescence in photoreceptors, RPE and Muller cells after serotype 8 Y733 delivery (FIG. 11D) Detection of Muller cells processes (red) by immunostaining with a glutamine-synthetase (GS) antibody (FIG. 11E) Merged image showing colocalization of EGFP fluorescence (green) and GS staining (red) in retinal sections from eyes treated with serotype 8 Y733 (FIG. 11F) Calibration bar 100 gcl, ganglion cell layer; ipl, inner plexiform layer; inl, inner nuclear layer; onl, outer nuclear; os, outer segment; rpe, retinal pigment epithelium.
Figure 11B:
Figure 11C:
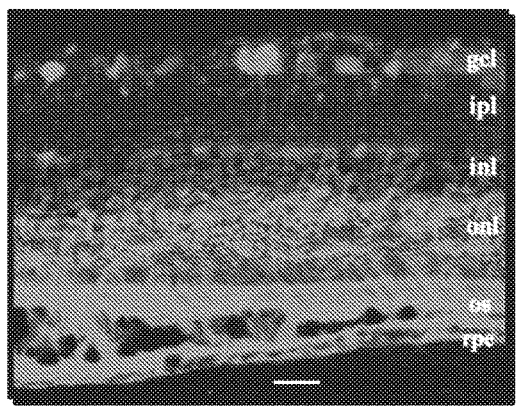
Figure 11D:
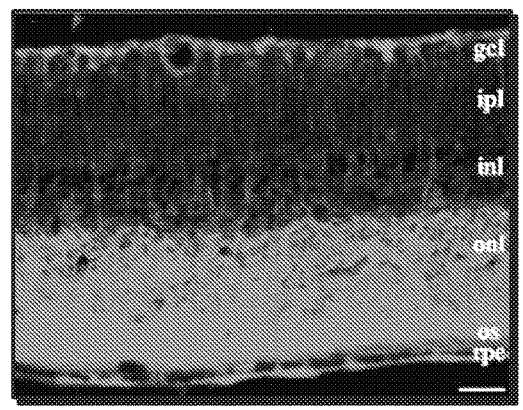
Figure 11E:
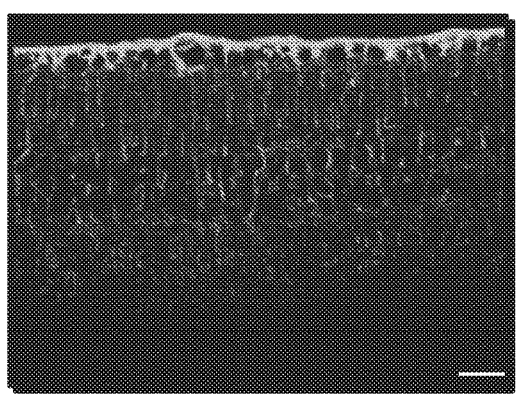
Figure 11F:
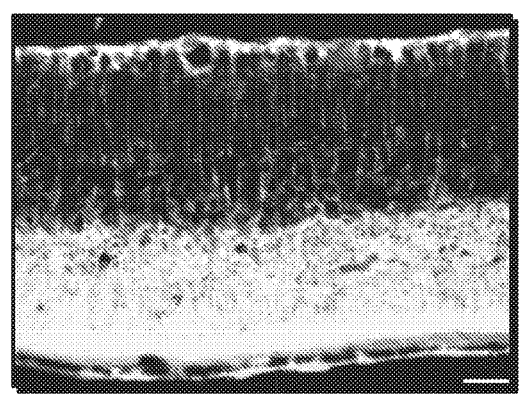

Example 5: AAV8 Mutant Y733F-GRM6-ChR2 and AAV8 Mutant Y446F-CBA-ChR2 to Establish Light Sensitivity in Retinal ON-Bipolar Cells Using a tyrosine-mutated version of AAV8 (at the 733 location), under the control of bipolar cell specific promoter GRM6, in the self-complementary configuration, it was possible to restore visual behavioral efficacy in rd1 mice, as depicted in FIG. 11A through FIG. 11F and FIG. 12A-1 through FIG. 12C. For example, FIG. 11A through FIG. 11F depict the analysis of EGFP expression in frozen retinal sections by immunohistochemistry at 1 month following subretinal injections with the tyrosine-mutated AAV vectors. Exemplary sections depicting spread and intensity of EGFP fluorescence throughout the retina after transduction with serotype 2 Y444 or serotype 8 Y733 are shown in FIG. 11A and FIG. 11B, respectively. The images are oriented with the vitreous toward the bottom and the photoreceptor layer toward the top. EGFP fluorescence in photoreceptors, RPE and ganglion cells from mouse eyes injected subretinally with serotype 2 Y444 (FIG. 11C) EGFP fluorescence in photoreceptors, RPE and Muller cells after serotype 8 Y733 delivery (FIG. 11D) Detection of Muller cells processes (red) by immunostaining with a glutamine-synthetase (GS) antibody (FIG. 11E) Merged image showing colocalization of EGFP fluorescence (green) and GS staining (red) in retinal sections from eyes treated with serotype 8 Y733 (FIG. 11F) Calibration bar 100 μM. gcl, ganglion cell layer; ipl, inner plexiform layer; inl, inner nuclear layer; onl, outer nuclear; os, outer segment; rpe, retinal pigment epithelium.

Using a tyrosine-mutated version of AAV8 (at the 446 location), under the control of the non-cell specific promoter CBA (fusion of the CMV immediate early enhancer and the bovine β-actin promoter plus intronl-exon1 junction, and ChR2), in the self-complementary configuration, most or all bipolar cells can be targeted and visual function is restored as depicted in FIG. 12A, FIG. 12B, and FIG. 12C.

Example 6: AAV5-CBA-ChR2 to Establish Light Sensitivity in Retinal on Bipolar Cells Using the AAV5, non-cell type specific promoter CBA (fusion of the CMV immediate early enhancer and the bovine β-actin promoter plus intronl-exon1 junction, and ChR2, in the self-complementary configuration, all bipolar cells can be targeted and visual function and behavior is restored (FIG. 12A, FIG. 12B, and FIG. 12C). Treated mice were subretinally (right eye) and intravitreally (left eye) injected with 1.5 μL of adeno-associated viruses (AAV) of different serotypes. The serotypes tested included AAV2, AAV5, and AAV7, all of which are traditional wild type serotypes. Additionally, the single tyrosine to phenylalanine mutated serotypes AAV2 Y444F mutant and AAV8 Y733F mutant, where 444 and 733 indicate the location of the point tyrosine mutation of the viral capsid, respectively. The virus contained the self-complementary DNA construct GRM6-ChR2-GFP, where GRM6 is the regulatory sequence driving cell-specific expression in the ON bipolar cells (including rod bipolar), ChR2 is the therapeutic, light-sensitive protein gene, and GFP is the reporter gene.

These mice were then trained on a water maze task FIG. 12A for 14 days (7 days for the wild type mice) and the time to find the target (a black platform with a 4×6 LED light source) was recorded. FIG. 12B shows the average time it took for the treated, untreated, and wild type mice to find the target, as a function of the training session. Both the untreated and treated groups contained samples from the rd1, rd16, and rho-/-(different mouse models of blindness that have different types of gene mutations that lead to photoreceptor disease) groups. These data demonstrate that mice treated with ChR2 are able to learn a behavior task by using visual information, suggesting that a light sensitive protein such as ChR2 has the ability to restore at least some visual function.

The animals' performance on the task was then evaluated at different light levels. FIG. 12C shows the average time it took for the rd1, rd16, and rho-/- treated, sham injected (sham injected mice represent an average of rd1, rd16, and rho-/- untreated), and wild type mice to find the target, as a function of the light intensity. These data show that the treated mice can perform the task at multiple light levels and their performance is dependent on the amount of light presented.

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising", "having", "including," or "containing," with reference to an element or elements is intended to provide support for a similar aspect or embodiment of the invention that "consists of," "consists essentially of" or "substantially comprises," that particular element or elements, unless otherwise stated or clearly contradicted by context (e.g., a composition described herein as comprising a particular element should be understood as also describing a composition that contains and/or that includes that particular element, unless otherwise explicated stated, or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A recombinant adeno-associated virus (rAAV) particle, comprising:
   (a) a mutated AAV2 VP3 capsid protein comprising phenylalanines at each of the positions corresponding to Y444, Y500 and Y730 in a wild type AAV2 VP3 capsid protein; and
   (b) a rAAV nucleic acid vector comprising a 5' inverted terminal repeat (ITR), a transgene, and a 3' ITR.

2. The rAAV particle of claim 1, wherein the transgene is operatively linked to a sequence that regulates expression of the transgene in a cell.

3. The rAAV particle of claim 2, wherein the sequence that regulates expression of the transgene in a cell is a promoter.

4. The rAAV particle of claim 1, wherein the transgene is about 2- to 5-kb in length.

5. The rAAV particle of claim 1, wherein the nucleic acid vector is a self-complementary (sc) vector.

6. The rAAV particle of claim 1, wherein the transgene is a reporter transgene.

7. A composition comprising:
   (a) a recombinant adeno-associated virus (rAAV) particle that comprises:
      (i) a mutated AAV2 VP3 capsid protein comprising phenylalanines at each of the positions corresponding to Y444, Y500 and Y730 in a wild type AAV2 VP3 capsid protein; and
      (ii) a rAAV nucleic acid vector comprising a 5' inverted terminal repeat (ITR), a transgene, and a 3' ITR; and
   (b) a carrier or an excipient.

8. The composition of claim 7, formulated for injection or topical application to a mammalian eye.

9. The rAAV particle of claim 1 further comprising a phenylalanine at the position corresponding to Y272 in a wild type AAV2 VP3 capsid.

10. A recombinant adeno-associated virus (rAAV) particle, comprising:
   (a) a mutated AAV2 VP3 capsid protein consisting of phenylalanines at each of the positions corresponding to Y444, Y500 and Y730 in a wild type AAV2 VP3 capsid protein; and
   (b) a rAAV nucleic acid vector comprising a 5' inverted terminal repeat (ITR), a transgene, and a 3' ITR.

* * * * *

SEQUENCE LISTING

<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Phe Cys Tyr Glu Asn Glu Val
1               5

<210> SEQ ID NO 2
<211> LENGTH: 2236
<212> TYPE: DNA
<213> ORGANISM: Chlamydomonas reinhardtii

<400> SEQUENCE: 2

| | | | | | | |
|---|---|---|---|---|---|---|
| gcgttgcttg | actacgcttc | gctgtaataa | tagcagcgcc | acaagtagtg | tcgccaaaca | 60 |
| actctcactt | tgagcttgag | cacaccgctg | agccccgatg | tcgcggaggc | catggcttct | 120 |
| tgccctagcg | ctggcagtgg | cgctggcggc | cggcagcgca | ggagcctcga | ctggcagtga | 180 |
| cgcgacggtg | ccggtcgcga | ctcaggatgg | ccccgactac | gttttccacc | gtgcccacga | 240 |
| gcgcatgctc | ttccaaacct | catacactct | tgagaacaat | ggttctgtta | tttgcatccc | 300 |
| gaacaacggc | cagtgcttct | gcttggcttg | gcttaaatcc | aacggaacaa | atgccgagaa | 360 |
| gttggctgcc | aacattctgc | agtggattac | ttttgcgctt | tcagcgctct | gcctgatgtt | 420 |
| ctacggctac | cagacctgga | agtctacttg | cggctgggag | gagatttacg | tggccacgat | 480 |
| cgagatgatc | aagttcatca | tcgagtattt | ccatgagttt | gacgaacctg | cggtgatcta | 540 |
| ctcatccaac | ggcaacaaga | ccgtgtggct | tcgttacgcg | gagtggctgc | tgacctgccc | 600 |
| tgtcattctt | atccatctga | gcaaccttac | gggtctggcg | aacgactata | caagcgtac | 660 |
| catgggtctg | ctggtgtcag | atatcggcac | gatcgtgtgg | ggcaccacgg | ccgcgctgtc | 720 |
| caagggatac | gtccgtgtca | ttttcttcct | gatgggcctg | tgctacggca | tctacacatt | 780 |
| cttcaacgca | gccaaggtct | acattgaggc | gtaccacacc | gtgcccaagg | catttgccg | 840 |
| cgacctggtc | cgctacccttg | cctggctcta | cttctgttca | tgggctatgt | tcccggtgct | 900 |
| gttcctgctg | ggccccgagg | gctttggcca | catcaaccaa | ttcaactctg | ccatcgccca | 960 |
| cgccatcctg | gaccttgcct | ccaagaacgc | ttggagtatg | atgggtcact | ttctgcgtgt | 1020 |
| caagatccac | gagcacatcc | tgctgtacgg | cgacatccgc | aagaagcaga | aggtcaacgt | 1080 |
| ggctggccag | gagatggagg | tggagaccat | ggtgcacgag | gaggacgacg | agacgcagaa | 1140 |
| ggtgcccacg | gcaaagtacg | ccaaccgcga | ctcgttcatc | atcatgcgcg | accgcctcaa | 1200 |
| ggagaagggc | ttcgagaccc | cgcctcgct | ggacggcgac | ccgaacgcg | acgccgaggc | 1260 |
| caacgctgca | gccggcggca | agcccggaat | ggagatgggc | aagatgaccg | gcatgggcat | 1320 |
| gggcatgggt | gccggcatgg | gcatggcgac | catcgattcg | ggccgcgtca | tcctcgccgt | 1380 |
| gccggacatc | tccatggtgg | acttttttccg | cgagcagttc | gcgcggctgc | ccgtgcccta | 1440 |
| cgaactggtg | cccgcgctgg | gcgcggagaa | caccctccag | ctggtgcagc | aggcgcagtc | 1500 |
| actgggaggc | tgcgacttcg | tcctcatgca | ccccgagttc | ctgcgcgacc | gcagtccccac | 1560 |
| gggtctgctg | ccccgcctca | agatgggcgg | gcagcgcgcc | gcggccttcg | gctgggcggc | 1620 |
| aatcggcccc | atgcgggact | tgatcgaggg | ttcgggcgtt | gacggctggc | tggagggccc | 1680 |
| cagcttttggc | gccggcatca | accagcaggc | gctggtggcg | ctgatcaacc | gcatgcagca | 1740 |
| ggccaagaag | atgggcatga | tgggcggtat | gggtatgggc | atgggcggcg | gcatgggtat | 1800 |
| gggcatgggt | atgggcatgg | gcatggcccc | cagcatgaac | gccggcatga | ctggcggcat | 1860 |
| gggcggcgcc | tccatggggcg | gtgccgtgat | gggcatgggc | atgggcatgc | agcccatgca | 1920 |
| gcaggctatg | ccgccatgt | cgccatgat | gactcagcag | cccagcatga | tgagtcagcc | 1980 |
| ctccgccatg | agcgccggcg | gcgccatgca | ggccatgggt | ggcgtcatgc | ccagccccgc | 2040 |

```
cccccggcggc cgcgtgggca ccaacccgct gtttggctct gcgccctctc cgctgagctc    2100
gcagcccggc atcagccctg gcatggcgac gccgcccgcc gccaccgccg cacccgccgc    2160
tggcggcagc gaggccgaga tgctgcagca gctgatgagc gagatcaacc gcctgaagaa    2220
cgagctgggc gagtaa                                                    2236
```

<210> SEQ ID NO 3
<211> LENGTH: 2241
<212> TYPE: DNA
<213> ORGANISM: Chlamydomonas reinhardtii

<400> SEQUENCE: 3

```
gcatctgtcg ccaagcaagc attaaacatg gattatggag gcgccctgag tgccgttggg     60
cgcgagctgc tatttgtaac gaacccagta gtcgtcaatg gctctgtact tgtgcctgag    120
gaccagtgtt actgcgcggg ctggattgag tcgcgtggca caaacggtgc ccaaacggcg    180
tcgaacgtgc tgcaatggct tgctgctggc ttctccatcc tactgcttat gttttacgcc    240
taccaaacat ggaagtcaac ctgcggctgg gaggagatct atgtgtgcgc tatcgagatg    300
gtcaaggtga ttctcgagtt cttcttcgag tttaagaacc cgtccatgct gtatctagcc    360
acaggccacc gcgtccagtg gttgcgttac gccgagtggc ttctcacctg cccggtcatt    420
ctcattcacc tgtcaaacct gacgggcttg tccaacgact acagcaggcg caccatgggt    480
ctgcttgtgt ctgatattgg cacaattgtg tggggcgcca cttccgccat ggccaccgga    540
tacgtcaagg tcatcttctt ctgcctgggt ctgtgttatg gtgctaacac gttctttcac    600
gctgccaagg cctacatcga gggttaccac accgtgccga agggccggtg tcgccaggtg    660
gtgactggca tggcttggct cttcttcgta tcatggggta tgttccccat cctgttcatc    720
ctcggccccg agggcttcgg cgtcctgagc gtgtacggct ccaccgtcgg ccacaccatc    780
attgacctga tgtcgaagaa ctgctggggt ctgctcggcc actacctgcg cgtgctgatc    840
cacgagcata tcctcatcca cggcgacatt cgcaagacca ccaaattgaa cattggtggc    900
actgagattg aggtcgagac gctggtggag gacgaggccg aggctggcgc ggtcaacaag    960
ggcaccggca agtacgcctc ccgcgagtcc ttcctggtca tgcgcgacaa gatgaaggag   1020
aagggcattg acgtgcgcgc ctctctggac aacagcaagg aggtggagca ggagcaggcc   1080
gccagggctg ccatgatgat gatgaacggc aatggcatgg gtatgggaat gggaatgaac   1140
ggcatgaacg gaatgggcgg tatgaacggg atggctggcg gcgccaagcc cggcctggag   1200
ctcactccgc agctacagcc cggccgcgtc atcctggcgg tgccggacat cagcatggtt   1260
gacttcttcc gcgagcagtt tgctcagcta tcggtgacgt acgagctggt gccggccctg   1320
ggcgctgaca cacactggc gctggttacg caggcgcaga acctgggcgg cgtggacttt   1380
gtgttgattc accccgagtt cctgcgcgac cgctctagca ccagcatcct gagccgcctg   1440
cgcggcgcgg ccagcgtgt ggctgcgttc ggctgggcgc agctgggcc catgcgtgac   1500 ctgatcgagt ccgcaaacct ggacggctgg ctggagggcc cctcgttcgg acagggcatc   1560
ctgccggccc acatcgttgc cctggtggcc aagatgcagc agatgcgcaa gatgcagcag   1620
atgcagcaga ttggcatgat gaccggcggc atgaacggca tggcggcgg tatgggcggc   1680 ggcatgaacg gcatgggcgg cggcaacggc atgaacaaca tgggcaacgg catgggcggc   1740
ggcatgggca acggcatggg cggcaatggc atgaacggaa tgggtggcgg caacggcatg   1800
aacaacatgg gcggcaacgg aatggccggc aacggaatgg gcggcggcat gggcggcaac   1860
```

```
ggtatgggtg gctccatgaa cggcatgagc tccggcgtgg tggccaacgt gacgccctcc    1920
gccgccggcg gcatgggcgg catgatgaac ggcggcatgg ctgcgcccca gtcgcccggc    1980
atgaacggcg gccgcctggg taccaacccg ctcttcaacg ccgcgccctc accgctcagc    2040
tcgcagctcg gtgccgaggc aggcatgggc agcatgggag gcatgggcgg aatgagcgga    2100
atgggaggca tgggtggaat gggggggcatg ggcggcgccg gcgccgccac gacgcaggct   2160 gcggcggca acgcggaggc ggagatgctg cagaatctca tgaacgagat caatcgcctg     2220
aagcgcgagc ttggcgagta a                                              2241

<210> SEQ ID NO 4
<211> LENGTH: 869
<212> TYPE: DNA
<213> ORGANISM: Natronomonas pharaonis

<400> SEQUENCE: 4
atgactgaga ccctcccacc cgtgactgaa agcgccgtcg ctctgcaagc agaggttacc      60
cagcgggagc tgttcgagtt cgtcctcaac gacccccctcc tggcttctag cctctacatc    120
aacatgctct ggcaggcctg tctatactgc tgttcgtctt catgaccagg ggactcgatg     180
accctagggc taaactgatt gcagtgagca caattctggt tcccgtggtc tctatcgctt     240
cctacactgg ctggcatctg gtctcacaat cagtgtcctg gaaatgccag ctggccactt     300
tgccgaaggg agttctgtca tgctgggagg cgaagaggtc gatggggttg tcacaatgtg     360
gggtcgctac ccacctgggc tctcagtacc ccatgatcc tgctggcact cggactcctg      420
gccggaagta acgccaccaa actcttcact gctattacat cgatatcgc catgtgcgtg      480 accgggctcg cagctccctc accaccagca gccatctgat gagatggttt tggtatgcca     540
tctcttgtgc ctgctttctg gtggtgctgt atatcctgct ggtggagtgg gctcaggatg     600
ccaaggctgc agggacagcg acatgtttaa tacactgaag ctgctcactg tggtgatgtg     660
gctgggttac cctatcgttt gggcactcgg cgtggaggga atcgcagttc tgcctgttgg     720
tgtgacaagc tggggctact cctcctggac attgtggcca agtatatttt tgcctttctg     780
ctgctgaatt atctgacttc caatgagtcc gtggtgtccg gctccatact ggacgtgcca     840
tccgccagcg gcacacctgc cgatgctga                                       869

<210> SEQ ID NO 5
<211> LENGTH: 1495
<212> TYPE: DNA
<213> ORGANISM: Mus musculus

<400> SEQUENCE: 5
gaggatccgc caccatgaac cctccttcgg gccctagagt cctgcccagc ccaacccaag      60
agcccagctg catggccacc ccagcaccac ccagctggtg ggacagctcc cagagcagca    120
tctccagcct gggccggctt ccatccatca gtcccacagc acctgggact tgggctgctg    180
cctgggtccc cctccccacg gttgatgttc cagaccatgc ccactatacc ctgggcacag    240
tgatcttgct ggtgggactc acgggcatgc ttggcaacct gacggtcatc tataccttct    300
gcaggagcag aagcctccgg acacctgcca acatgttcat tatcaacctc gcggtcagcg    360
acttcctcat gagtttcacc caggccctg tcttcttcac cagtagcctc tataagcagt    420 ggctcttttgg ggagacaggc tgcgagttct atgccttctg tggagctctc tttggcattt    480
cctccatgat caccctgacg gccatcgccc tggaccgcta cctggtaatc acacgcccgc    540
tggccacctt tggtgtggcg tccaagaggc gtgcggcatt tgtcctgctg ggcgtttggc    600
```

```
tctatgcgct agcttggagt ctgccaccct tcttcggctg gagcgcctac gtgcccgagg      660
ggttgctgac atcctgctcc tgggactaca tgagcttcac gccggccgtg cgtgcctaca      720
ccatgcttct ctgctgcttc gtgttcttcc tccctttatt aattatcatc tactgctaca      780
tcttcatctt cagggccatc cgggagacag gacgggctct ccagaccttc ggggcctgca      840
agggcaatgg cgagtccctg tggcagcggc agcggctgca gagcgagtgc aagatggcca      900
agatcatgct gctggtcatc ctcctcttcg tgctctcctg gctccctat tccgctgtgg       960 ccctggtggc ctttgctggg tacgcacacg tcctgacacc ctacatgagc tcggtgccag      1020
ccgtcatcgc caaggcctct gcaatccaca accccatcat ttacgccatc acccacccca     1080
agtacagggt ggccattgcc cagcacctgc cctgcctagg tgtgctgctg ggtgtatcac      1140
gccggcacag tcgcccctac cccagctacc gctccaccca ccgctccacg ctgaccagcc      1200
acacctccaa cctcagctgg atctccatac ggaggcgcca ggagtccctg gctcggaga      1260 gtgaggtggg ctggacacac atggaggcag cagctgtgtg gggagctgcc cagcaagcaa      1320
atgggcggtc cctctacggt cagggtctgg aggacttgga agccaaggca ccccccagac      1380
cccagggaca cgaagcagag actccaggga agaccaaggg gctgatcccc agccaggacc      1440
cgcggatggg cggcggcgac tacaaggacg atgatgacaa gtaataagaa ttcag          1495

<210> SEQ ID NO 6
<211> LENGTH: 1665
<212> TYPE: DNA
<213> ORGANISM: Artificial Sequence
<220> FEATURE:
<223> OTHER INFORMATION: Synthetic Polynucleotide

<400> SEQUENCE: 6
atggactatg gcggcgcttt gtctgccgtc ggacgcgaac ttttgttcgt tactaatcct       60
gtggtggtga acgggtccgt cctggtccct gaggatcaat gttactgtgc cggatggatt      120
gaatctcgcg gcacgaacgg cgctcagacc gcgtcaaatg tcctgcagtg gcttgcagca      180
ggattcagca tttttgctgct gatgttctat gcctaccaaa cctggaaatc tacatgcggc      240
tgggaggaga tctatgtgtg cgccattgaa atggttaagg tgattctcga gttcttttt      300 gagtttaaga tccctctat gctctacctt gccacaggac accgggtgca gtggctgcgc      360
tatgcagagt ggctgctcac ttgtcctgtc atccttatcc acctgagcaa cctcaccggc      420
ctgagcaacg actacagcag gagaaccatg ggactccttg tctcagacat cgggactatc      480 gtgtggggg ctaccagcgc catggcaacc ggctatgtta agtcatctt cttttgtctt      540 ggattgtgct atggcgcgaa acatttttt cacgccgcca agcatatat cgagggttat      600 catactgtgc caagggtcg gtgccgccag gtcgtgaccg gcatggcatg ctgttttc      660 gtgagctggg gtatgttccc aattctcttc attttgggc ccgaaggttt tggcgtcctg      720
agcgtctatg ctccaccgt aggtcacacg attattgatc tgatgagtaa aaattgttgg      780 ggttgttgg gacactacct gcgcgtcctg atccacgagc acatattgat tcacggagat      840
atccgcaaaa ccaccaaact gaacatcggc ggaacggaga tcgaggtcga gactctcgtc      900
gaagacgaag ccgaggccgg agccgtgcca gcggcaccgg tagtagcagt gagcaagggc      960
gaggagctgt tcaccggggt ggtgcccatc ctggtcgagc tggacggcga cgtaaacggc     1020
cacaagttca gcgtgtccgg cgagggcgag ggcgatgcca cctacggcaa gctgaccctg     1080
aagttcattt gcaccaccgg caagctgccc gtgccctggc ccaccctcgt gaccaccctg     1140
```

```
acctacggcg tgcagtgctt cagccgctac cccgaccaca tgaagcagca cgacttcttc    1200
aagtccgcca tgcccgaagg ctacgtccag gagcgcacca tcttcttcaa ggacgacggc    1260
aactacaaga cccgcgccga ggtgaagttc gagggcgaca ccctggtgaa ccgcatcgag    1320
ctgaagggca tcgacttcaa ggaggacggc aacatcctgg ggcacaagct ggagtacaac    1380
tacaacagcc acaacgtcta tatcatggcc gacaagcaga agaacggcat caaggtgaac    1440
ttcaagatcc gccacaacat cgaggacggc agcgtgcagc tcgccgacca ctaccagcag    1500 aacacccca tcggcgacgg ccccgtgctg ctgcccgaca accactacct gagcacccag    1560
tccgccctga gcaaagaccc caacgagaag cgcgatcaca tggtcctgct ggagttcgtg    1620
accgccgccg ggatcactct cggcatggac gagctgtaca agtaa                   1665

<210> SEQ ID NO 7
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 7
atctccagat ggctaaactt ttaaatcatg aatgaagtag atattaccaa attgcttttt      60
cagcatccat ttagataatc atgtttttg cctttaatct gttaatgtag tgaattacag     120
aaatacattt cctaaatcat tacatccccc aaatcgttaa tctgctaaag tacatctctg     180
gctcaaacaa gactggttg                                                 199

<210> SEQ ID NO 8
<211> LENGTH: 952
<212> TYPE: DNA
<213> ORGANISM: Artificial Sequence
<220> FEATURE:
<223> OTHER INFORMATION: Synthetic Polynucleotide

<400> SEQUENCE: 8
aattcggtac cctagttatt aatagtaatc aattacgggg tcattagttc atagcccata      60
tatggagttc cgcgttacat aacttacggt aaatggcccg cctggctgac cgcccaacga    120
cccccgccca ttgacgtcaa taatgacgta tgttcccata gtaacgccaa tagggacttt    180
ccattgacgt caatgggtgg actatttacg gtaaactgcc cacttggcag tacatcaagt    240
gtatcatatg ccaagtacgc cccctattga cgtcaatgac ggtaaatggc ccgcctggca    300
ttatgcccag tacatgacct tatgggactt tcctacttgg cagtacatct acgtattagt    360
catcgctatt accatggtcg aggtgagccc cacgtttgct tcactctccc catctccccc    420
ccctccccac cccaattttt gtatttattt attttttaat tattttgtgc agcgatgggg    480 gcggggggg gggggggcg cgcgccaggc ggggcgggc ggggcgaggg gcggggcggg    540
gcgaggcgga gaggtgcggc ggcagccaat cagagcggcg cgctccgaaa gtttcctttt    600
atggcgaggc ggcggcggcg gcggccctat aaaaagcgaa gcgcgcggcg gcgggagtc    660 gctgcgacgc tgccttcgcc ccgtgccccg ctccgccgcc gcctcgcgcc gcccgccccg    720
gctctgactg accgcgttac tcccacaggt gagcgggcgg gacggccctt ctcctccggg    780
ctgtaattag cgcttggttt aatgacggct tgtttctttt ctgtggctgc gtgaaagcct    840 tgagggctc cggagctag agcctctgct aaccatgttc atgccttctt cttttttccta    900 cagctcctgg gcaacgtgct ggttattgtg ctgtctcatc attttggcaa ag           952
```